US007439058B2

(12) United States Patent
Selby et al.

(10) Patent No.: US 7,439,058 B2
(45) Date of Patent: Oct. 21, 2008

(54) HBV/HCV VIRUS-LIKE PARTICLE

(75) Inventors: Mark Selby, San Francisco, CA (US);
Edward Glazer, Oakland, CA (US);
Michael Houghton, Berkeley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 10/715,665

(22) Filed: Nov. 17, 2003

(65) Prior Publication Data

US 2004/0146529 A1    Jul. 29, 2004

Related U.S. Application Data

(62) Division of application No. 09/721,480, filed on Nov. 22, 2000, now Pat. No. 6,740,323.

(60) Provisional application No. 60/167,224, filed on Nov. 24, 1999.

(51) Int. Cl.
*C07H 21/00* (2006.01)
*C12N 7/00* (2006.01)
*C12N 7/02* (2006.01)
*C12N 7/04* (2006.01)
*C12N 5/10* (2006.01)
*C12N 15/00* (2006.01)

(52) U.S. Cl. .................. 435/320.1; 536/23.1; 536/23.4; 536/23.72; 435/235.1; 435/236; 435/239; 435/325

(58) Field of Classification Search .............. 424/184.1, 424/186.1, 189.1, 192.1, 202.1, 204.1, 227.1, 424/228.1; 435/69.1, 69.3, 69.7, 71.1, 471, 435/476, 252.3, 254.11, 254.2, 320.1; 514/44; 536/23.1, 23.4, 23.7, 23.72
See application file for complete search history.

(56) References Cited

U.S. PATENT DOCUMENTS

| | | | |
|---|---|---|---|
| 4,722,840 A | | 2/1988 | Valenzuela et al. |
| 5,098,704 A | | 3/1992 | Valenzuela et al. |
| 5,292,646 A | * | 3/1994 | McCoy et al. .............. 435/69.7 |
| 5,324,513 A | | 6/1994 | Sobczak et al. |
| 5,792,463 A | | 8/1998 | Valenzuela et al. |
| 5,928,902 A | * | 7/1999 | De Wilde et al. ........... 435/69.3 |
| 5,942,234 A | * | 8/1999 | Ralston et al. ............ 424/228.1 |
| 6,096,505 A | * | 8/2000 | Selby et al. ..................... 435/6 |
| 6,306,625 B1 | * | 10/2001 | Jacobs et al. ............... 435/69.9 |
| 6,890,737 B1 | * | 5/2005 | Maertens et al. ........... 435/69.3 |
| 2003/0211996 A1 | * | 11/2003 | Gowans et al. ................ 514/12 |
| 2005/0220858 A1 | * | 10/2005 | Bacon et al. ................ 424/450 |
| 2005/0272097 A1 | * | 12/2005 | Calenoff ...................... 435/7.2 |

FOREIGN PATENT DOCUMENTS

| | | |
|---|---|---|
| EP | 0 201 416 A1 | 11/1986 |
| WO | WO 93/06126 | 4/1993 |
| WO | WO 96/04301 | 2/1996 |

OTHER PUBLICATIONS

Michalak et al., Journal of General Virology, vol. 78 No. 9, pp. 2299-2306 (Sep. 1997).*
NCBI printour, GenBank Accession X02763, Hepatitis B Virus genome, (Sep. 1992).*
NCBI printout, GenBank Accession M62321, Hepatitis V Virus polyprotein precursor (HCV-1) mRNA (Aug. 1993).*
NCBI printout, GenBank Accession E01163, cDNA encoding human tissue plasminogen activator (Sep. 1997).*
Chapman et al., Nucleic Acids Research, vol. 19 No. 14, pp. 3979-3986 (Jul. 1991).*
Hartikka et al., Human Gene Therapy, vol. 7 No. 10, pp. 1205-1217 (Jun. 1996).*
Simmonds et al., Journal of Clinical Microbiology, vol. 31 No. 6,pp. 1493-1503 (Jun. 1993).*
Jackson et al., Journal of Medical Virology, vol. 51 No. 1, pp. 67-79 (Jan. 1997).*
Choo et al., Proceedings of the National Academy of Sciences, U.S. A., colume 88 No. 6, pp. 2451-2455 (Mar. 1991).*
Bowie et al., Deciphering the message in protein sequences: tolerance to amino acid substitutions, Science, vol. 247 No. 4948, pp. 1306-1310 (Mar. 1990).*
Green et al., Potent T cell response to a class I-binding 13-mer viral epitope and the influence of HLA micropolymorphism in controlling epitope length, European Journal of Immunology, vol. 34 No. 9, pp. 2510-2519 (Sep. 2004).*
Riffkin et al., A single amino-acid change between the antigenically different extracellular serine proteases V2 and B2 from Dichelobacter nodosus, Gene, vol. 167 Nos. 1-2, pp. 279-283 (Dec. 1995).*
Martínez-Salas, Internal ribosome entry site biology and its use in expression vectors, Current Opinion in Biotechnology, vol. 10 No. 5, pp. 458-464 (Oct. 1999).*
Mountford et al., Dicistronic targeting constructs: REporters and modifiers of mammalian gene expression, Proceedings of the National Academy of Sciences, vol. 91 No. 10, pp. 4303-4307 (May 1994).*

(Continued)

*Primary Examiner*—Zachariah Lucas
(74) *Attorney, Agent, or Firm*—Mark Seka; Roberta L. Robins

(57) ABSTRACT

Chimeric antigens derived from hepatitis B virus (HBV) and hepatitis C virus (HCV) are described which form virus-like particles when co-expressed with an excess of hepatitis B virus surface antigen (HBsAg). The chimeric antigens are fusion proteins containing an immunogenic peptide derived from an HCV protein coupled to the amino terminus of HBsAg. Also described are nucleic acid constructs and vectors for transfection of cells and expression of the chimeric antigens. The invention further provides methods for producing HBV/HCV virus-like particles containing the chimeric antigens, cell lines for producing the virus-like particles, combination vaccines containing the virus-like particles, and DNA vaccines that express the virus-like particles.

7 Claims, 44 Drawing Sheets

OTHER PUBLICATIONS

Pizzato et al., Production and characterization of a bicistronic Moloney-based retroviral vector expressing human interleukin 2 and herpes simplex virus thymidine kinase for gene therapy of cancer, Gene Therapy, vol. 5 No. 7, pp. 1003-1007 (Jul. 1998).*

Cardoso et al., "Isolation and characterization of human monoclonal antibodies against hepatitis C virus envelope glycoproteins," Journal of Medical Virology, vol. 55 No. 1, pp. 28-34 (May 1998).*

Esumi et al., "Murine Antibodies against E2 and Hypervariable Region 1 Cross-Reactively Capture Hepatitis C Virus," Virology, vol. 251 No. 1, pp. 158-164 (Nov. 1998).*

Esumi et al., "Experimental vaccine activities of recombinant E1 and E2 glycoproteins and hypervariable region 1 peptides of hepatitis C virus in chimpanzees," Archives of Virology, vol. 144 No. 5, pp. 973-980 (May 1999).*

Fournillier et al., "Expression of Noncovalent Hepatitis C Virus Envelope E1-E2 Complexes Is Not Required for the Induction of Antibodies with Neutralizing Properties following DNA Immunization," Journal of Virology, vol. 73 Np. 9, pp. 7497-7504 (Sep. 1999).*

Golden et al., Protein Expression and Purification, vol. 14 No. 1, pp. 8-12 (Oct. 1998).*

Flint et al., Journal of Virology, col. 73 No. 8, pp. 6782-6790 (Aug. 1999).*

Ono et al., Nucleic Acids REsearch, vol. 11 No. 6, pp. 1747-1757 (1983).*

Delpeyroux et al., "Structural Factors Modulate the Activity of Antigenic Poliovirus Sequences Expressed on Hybrid Hepatitis B surface Antigen Particles," *J. Virol. 64*(12):6090-6100 (1990).

Delpeyroux et al., "Presentation and immunogenicity of the hepatitis B surface antigen and a poliovirus neutralization antigen on mixed emplt ebvelope particles", *J. Virol. 62*(5):1836-1839 (1998).

Inchauspé et al., "DNA Vaccination for the Induction of Immune Responses Against Hepatitis C Virus Proteins," *Vaccine 15*(8):853-856 (1997).

Inchauspé et al., "Immune Responses Against Hepatitis C Virus Structural Proteins Following Genetic Immunization," *Dev. Biol. Stand. 92*:163-168 (1998).

Lee et al., "Presentation of the hydrophilic domains of hepatitis C viral E2 envelope glycoprotein on hepatitis B surface antigen particles," *Journal of Medical Virology 50*:145-151 (1996).

Lee et al., "Characterization of a New Genotype II Hepatitis Delta Virus from Taiwan," *Journal of Medical Virology 49*:145-154 (1996).

Major et al., "DNA-based immunization with chimeric vectors for the induction of immune responses against the hepatitis C virus nucleocapsid," *Journal of Virology 69*(9):5798-5805 (1995).

Nakano et al., "Immunization with Plasmid DNA Encoding Hepatitis C Virus Envelope E2 Antigenic Domains Induces Antibodies Whose Immune Reactivity is Linked to the Injection Mode," *Journal of Virology 71*(9):7101-7109 (1997).

Valenzuela et al., "Antigen Engineering in Yeast: Synthesis and Assembly of Hybrid Hepatitis B Surface Antigen-Herpes Simplex 1 gD Particles," *Bio/Technology 3*:323-326 (1985).

* cited by examiner

SEQ ID NO: 1                                                          PCMVII

→ 1    TCGCGCGTTT CGGTGATGAC GGTGAAAACC TCTGACACAT GCAGCTCCCG
       AGCGCGCAAA GCCACTACTG CCACTTTTGG AGACTGTGTA CGTCGAGGGC

51   GAGACGGTCA CAGCTTGTCT GTAAGCGGAT GCCGGGAGCA GACAAGCCCG
       CTCTGCCAGT GTCGAACAGA CATTCGCCTA CGGCCCTCGT CTGTTCGGGC

101   TCAGGGCGCG TCAGCGGGTG TTGGCGGGTG TCGGGGCTGG CTTAACTATG
       AGTCCCGCGC AGTCGCCCAC AACCGCCCAC AGCCCCGACC GAATTGATAC

HindIII
                                                     -------
 151   CGGCATCAGA GCAGATTGTA CTGAGAGTGC ACCATATGAA GCTTTTTGCA
       GCCGTAGTCT CGTCTAACAT GACTCTCACG TGGTATACTT CGAAAAACGT 201   AAAGCCTAGG CCTCCAAAAA AGCCTCCTCA CTACTTCTGG AATAGCTCAG
       TTTCGGATCC GGAGGTTTTT TCGGAGGAGT GATGAAGACC TTATCGAGTC 251   AGGCCGAGGC GGCCTCGGCC TCTGCATAAA TAAAAAAAAT TAGTCAGCCA
       TCCGGCTCCG CCGGAGCCGG AGACGTATTT ATTTTTTTTA ATCAGTCGGT 301   TGGGGCGGAG AATGGGCGGA ACTGGGCGGG GAGGGAATTA TTGGCTATTG
       ACCCCGCCTC TTACCCGCCT TGACCCGCCC CTCCCTTAAT AACCGATAAC 351   GCCATTGCAT ACGTTGTATC TATATCATAA TATGTACATT TATATTGGCT
       CGGTAACGTA TGCAACATAG ATATAGTATT ATACATGTAA ATATAACCGA 401   CATGTCCAAT ATGACCGCCA TGTTGACATT GATTATTGAC TAGTTATTAA
       GTACAGGTTA TACTGGCGGT ACAACTGTAA CTAATAACTG ATCAATAATT 451   TAGTAATCAA TTACGGGGTC ATTAGTTCAT AGCCCATATA TGGAGTTCCG
       ATCATTAGTT AATGCCCCAG TAATCAAGTA TCGGGTATAT ACCTCAAGGC 501   CGTTACATAA CTTACGGTAA ATGGCCCGCC TGGCTGACCG CCCAACGACC
       GCAATGTATT GAATGCCATT TACCGGGCGG ACCGACTGGC GGGTTGCTGG 551   CCCGCCCATT GACGTCAATA ATGACGTATG TTCCCATAGT AACGCCAATA
       GGGCGGGTAA CTGCAGTTAT TACTGCATAC AAGGGTATCA TTGCGGTTAT 601   GGGACTTTCC ATTGACGTCA ATGGGTGGAG TATTTACGGT AAACTGCCCA
       CCCTGAAAGG TAACTGCAGT TACCCACCTC ATAAATGCCA TTTGACGGGT 651   CTTGGCAGTA CATCAAGTGT ATCATATGCC AAGTCCGCCC CCTATTGACG
       GAACCGTCAT GTAGTTCACA TAGTATACGG TTCAGGCGGG GGATAACTGC 701   TCAATGACGG TAAATGGCCC GCCTGGCATT ATGCCCAGTA CATGACCTTA
       AGTTACTGCC ATTTACCGGG CGGACCGTAA TACGGGTCAT GTACTGGAAT 751   CGGGACTTTC CTACTTGGCA GTACATCTAC GTATTAGTCA TCGCTATTAC
       GCCCTGAAAG GATGAACCGT CATGTAGATG CATAATCAGT AGCGATAATG 801   CATGGTGATG CGGTTTTGGC AGTACACCAA TGGGCGTGGA TAGCGGTTTG
       GTACCACTAC GCCAAAACCG TCATGTGGTT ACCCGCACCT ATCGCCAAAC 851   ACTCACGGGG ATTTCCAAGT CTCCACCCCA TTGACGTCAA TGGGAGTTTG
       TGAGTGCCCC TAAAGGTTCA GAGGTGGGGT AACTGCAGTT ACCCTCAAAC

FIG. 1B

```
 901  TTTTGGCACC AAAATCAACG GGACTTTCCA AAATGTCGTA ATAACCCCGC
      AAAACCGTGG TTTTAGTTGC CCTGAAAGGT TTTACAGCAT TATTGGGCG

951  CCCGTTGACG CAAATGGGCG GTAGGCGTGT ACGGTGGGAG GTCTATATAA
      GGGCAACTGC GTTTACCCGC CATCCGCACA TGCCACCCTC CAGATATATT

1001  GCAGAGCTCG TTTAGTGAAC CGTCAGATCG CCTGGAGACG CCATCCACGC
      CGTCTCGAGC AAATCACTTG GCAGTCTAGC GGACCTCTGC GGTAGGTGCG

1051  TGTTTTGACC TCCATAGAAG ACACCGGGAC CGATCCAGCC TCCGCGGCCG
      ACAAAACTGG AGGTATCTTC TGTGGCCCTG GCTAGGTCGG AGGCGCCGGC

1101  GGAACGGTGC ATTGGAACGC GGATTCCCCG TGCCAAGAGT GACGTAAGTA
      CCTTGCCACG TAACCTTGCG CCTAAGGGGC ACGGTTCTCA CTGCATTCAT

1151  CCGCCTATAG ACTCTATAGG CACACCCCTT TGGCTCTTAT GCATGCTATA
      GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGTGA
      GACAAAAACC GAACCCCGGA TATGTGGGGG CGAGGAATAC GATATCCACT

1251  TGGTATAGCT TAGCCTATAG GTGTGGGTTA TTGACCATTA TTGACCACTC
      ACCATATCGA ATCGGATATC CACACCCAAT AACTGGTAAT AACTGGTGAG

1301  CCCTATTGGT GACGATACTT TCCATTACTA ATCCATAACA TGGCTCTTTG
      GGGATAACCA CTGCTATGAA AGGTAATGAT TAGGTATTGT ACCGAGAAAC

1351  CCACAACTAT CTCTATTGGC TATATGCCAA TACTCTGTCC TTCAGAGACT
      GGTGTTGATA GAGATAACCG ATATACGGTT ATGAGACAGG AAGTCTCTGA

1401  GACACGGACT CTGTATTTTT ACAGGATGGG GTCCATTTAT TATTTACAAA
      CTGTGCCTGA GACATAAAAA TGTCCTACCC CAGGTAAATA ATAAATGTTT

1451  TTCACATATA CAACAACGCC GTCCCCCGTG CCCGCAGTTT TTATTAAACA
      AAGTGTATAT GTTGTTGCGG CAGGGGGCAC GGGCGTCAAA AATAATTTGT

1501  TAGCGTGGGA TCTCCGACAT CTCGGGTACG TGTTCCGGAC ATGGGCTCTT
      ATCGCACCCT AGAGGCTGTA GAGCCCATGC ACAAGGCCTG TACCCGAGAA

1551  CTCCGGTAGC GGCGGAGCTT CCACATCCGA GCCCTGGTCC CATCCGTCCA
      GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA
      CGCCGAGTAC CAGCGAGCCG TCGAGGAACG AGGATTGTCA CCTCCGGTCT

1651  CTTAGGCACA GCACAATGCC CACCACCACC AGTGTGCCGC ACAAGGCCGT
      GAATCCGTGT CGTGTTACGG GTGGTGGTGG TCACACGGCG TGTTCCGGCA

1701  GGCGGTAGGG TATGTGTCTG AAAATGAGCT CGGAGATTGG GCTCGCACCT
      CCGCCATCCC ATACACAGAC TTTTACTCGA GCCTCTAACC CGAGCGTGGA

1751  GGACGCAGAT GGAAGACTTA AGGCAGCGGC AGAAGAAGAT GCAGGCAGCT
      CCTGCGTCTA CCTTCTGAAT TCCGTCGCCG TCTTCTTCTA CGTCCGTCGA

1801  GAGTTGTTGT ATTCTGATAA GAGTCAGAGG TAACTCCCGT TGCGGTGCTG
      CTCAACAACA TAAGACTATT CTCAGTCTCC ATTGAGGGCA ACGCCACGAC
```

FIG. 1C

```
1851  TTAACGGTGG AGGGCAGTGT AGTCTGAGCA GTACTCGTTG CTGCCGCGCG
      AATTGCCACC TCCCGTCACA TCAGACTCGT CATGAGCAAC GACGGCGCGC

1901  CGCCACCAGA CATAATAGCT GACAGACTAA CAGACTGTTC CTTTCCATGG
      GCGGTGGTCT GTATTATCGA CTGTCTGATT GTCTGACAAG GAAAGGTACC

SalI        EcoRI      XhoI
                                ------      ------     ------
1951  GTCTTTTCTG CAGTCACCGT CGTCGACCTA AGAATTCAGA CTCGAGCAAG
      CAGAAAAGAC GTCAGTGGCA GCAGCTGGAT TCTTAAGTCT GAGCTCGTTC

XbaI        AscI        EcoRV     BamHI      MluI
       ------    --------    -------    ------    -------
2001  TCTAGAAAGG CGCGCCAAGA TATCAAGGAT CCACTACGCG TTAGAGCTCG
      AGATCTTTCC GCGCGGTTCT ATAGTTCCTA GGTGATGCGC AATCTCGAGC

2051  CTGATCAGCC TCGACTGTGC CTTCTAGTTG CCAGCCATCT GTTGTTTGCC
      GACTAGTCGG AGCTGACACG GAAGATCAAC GGTCGGTAGA CAACAAACGG

2101  CCTCCCCCGT GCCTTCCTTG ACCCTGGAAG GTGCCACTCC CACTGTCCTT
      GGAGGGGGCA CGGAAGGAAC TGGGACCTTC CACGGTGAGG GTGACAGGAA

2151  TCCTAATAAA ATGAGGAAAT TGCATCGCAT TGTCTGAGTA GGTGTCATTC
      AGGATTATTT TACTCCTTTA ACGTAGCGTA ACAGACTCAT CCACAGTAAG

2201  TATTCTGGGG GGTGGGGTGG GGCAGGACAG CAAGGGGGAG GATTGGGAAG
      ATAAGACCCC CCACCCCACC CCGTCCTGTC GTTCCCCCTC CTAACCCTTC

2251  ACAATAGCAG GCATGCTGGG GAGCTCTTCC GCTTCCTCGC TCAGTGACTC
      TGTTATCGTC CGTACGACCC CTCGAGAAGG CGAAGGAGCG AGTCACTGAG

2301  GCTGCGCTCG GTCGTTCGGC TGCGGCGAGC GGTATCAGCT CACTCAAAGG
      CGACGCGAGC CAGCAAGCCG ACGCCGCTCG CCATAGTCGA GTGAGTTTCC

2351  CGGTAATACG GTTATCCACA GAATCAGGGG ATAACGCAGG AAAGAACATG
      GCCATTATGC CAATAGGTGT CTTAGTCCCC TATTGCGTCC TTTCTTGTAC

2401  TGAGCAAAAG GCCAGCAAAA GGCCAGGAAC CGTAAAAAGG CCGCGTTGCT
      ACTCGTTTTC CGGTCGTTTT CCGGTCCTTG GCATTTTTCC GGCGCAACGA

2451  GGCGTTTTTC CATAGGCTCC GCCCCCCTGA CGAGCATCAC AAAAATCGAC
      CCGCAAAAAG GTATCCGAGG CGGGGGGACT GCTCGTAGTG TTTTTAGCTG

2501  GCTCAAGTCA GAGGTGGCGA AACCCGACAG GACTATAAAG ATACCAGGCG
      CGAGTTCAGT CTCCACCGCT TTGGGCTGTC CTGATATTTC TATGGTCCGC

2551  TTTCCCCCTG GAAGCTCCCT CGTGCGCTCT CCTGTTCCGA CCCTGCCGCT
      AAAGGGGGAC CTTCGAGGGA GCACGCGAGA GGACAAGGCT GGGACGGCGA

2601  TACCGGATAC CTGTCCGCCT TTCTCCCTTC GGGAAGCGTG GCGCTTTCTC
      ATGGCCTATG GACAGGCGGA AAGAGGGAAG CCCTTCGCAC CGCGAAAGAG

2651  AATGCTCACG CTGTAGGTAT CTCAGTTCGG TGTAGGTCGT TCGCTCCAAG
      TTACGAGTGC GACATCCATA GAGTCAAGCC ACATCCAGCA AGCGAGGTTC

2701  CTGGGCTGTG TGCACGAACC CCCCGTTCAG CCCGACCGCT GCGCCTTATC
      GACCCGACAC ACGTGCTTGG GGGGCAAGTC GGGCTGGCGA CGCGGAATAG
```

FIG. 1D

```
2751  CGGTAACTAT CGTCTTGAGT CCAACCCGGT AAGACACGAC TTATCGCCAC
      GCCATTGATA GCAGAACTCA GGTTGGGCCA TTCTGTGCTG AATAGCGGTG

2801  TGGCAGCAGC CACTGGTAAC AGGATTAGCA GAGCGAGGTA TGTAGGCGGT
      ACCGTCGTCG GTGACCATTG TCCTAATCGT CTCGCTCCAT ACATCCGCCA

2851  GCTACAGAGT TCTTGAAGTG GTGGCCTAAC TACGGCTACA CTAGAAGGAC
      CGATGTCTCA AGAACTTCAC CACCGGATTG ATGCCGATGT GATCTTCCTG

2901  AGTATTTGGT ATCTGCGCTC TGCTGAAGCC AGTTACCTTC GGAAAAAGAG
      TCATAAACCA TAGACGCGAG ACGACTTCGG TCAATGGAAG CCTTTTTCTC

2951  TTGGTAGCTC TTGATCCGGC AAACAAACCA CCGCTGGTAG CGGTGGTTTT
      AACCATCGAG AACTAGGCCG TTTGTTTGGT GGCGACCATC GCCACCAAAA

3001  TTTGTTTGCA AGCAGCAGAT TACGCGCAGA AAAAAAGGAT CTCAAGAAGA
      AAACAAACGT TCGTCGTCTA ATGCGCGTCT TTTTTTCCTA GAGTTCTTCT

3051  TCCTTTGATC TTTTCTACGG GGTCTGACGC TCAGTGGAAC GAAAACTCAC
      AGGAAACTAG AAAAGATGCC CCAGACTGCG AGTCACCTTG CTTTTGAGTG

3101  GTTAAGGGAT TTTGGTCATG AGATTATCAA AAAGGATCTT CACCTAGATC
      CAATTCCCTA AAACCAGTAC TCTAATAGTT TTTCCTAGAA GTGGATCTAG

3151  CTTTTAAATT AAAAATGAAG TTTTAAATCA ATCTAAAGTA TATATGAGTA
      GAAAATTTAA TTTTTACTTC AAAATTTAGT TAGATTTCAT ATATACTCAT

3201  AACTTGGTCT GACAGTTACC AATGCTTAAT CAGTGAGGCA CCTATCTCAG
      TTGAACCAGA CTGTCAATGG TTACGAATTA GTCACTCCGT GGATAGAGTC

3251  CGATCTGTCT ATTTCGTTCA TCCATAGTTG CCTGACTCCC CGTCGTGTAG
      GCTAGACAGA TAAAGCAAGT AGGTATCAAC GGACTGAGGG GCAGCACATC

3301  ATAACTACGA TACGGGAGGG CTTACCATCT GGCCCCAGTG CTGCAATGAT
      TATTGATGCT ATGCCCTCCC GAATGGTAGA CCGGGGTCAC GACGTTACTA

3351  ACCGCGAGAC CCACGCTCAC CGGCTCCAGA TTTATCAGCA ATAAACCAGC
      TGGCGCTCTG GGTGCGAGTG GCCGAGGTCT AAATAGTCGT TATTTGGTCG

3401  CAGCCGGAAG GGCCGAGCGC AGAAGTGGTC CTGCAACTTT ATCCGCCTCC
      GTCGGCCTTC CCGGCTCGCG TCTTCACCAG GACGTTGAAA TAGGCGGAGG

3451  ATCCAGTCTA TTAATTGTTG CCGGGAAGCT AGAGTAAGTA GTTCGCCAGT
      TAGGTCAGAT AATTAACAAC GGCCCTTCGA TCTCATTCAT CAAGCGGTCA

3501  TAATAGTTTG CGCAACGTTG TTGCCATTGC TACAGGCATC GTGGTGTCAC
      ATTATCAAAC GCGTTGCAAC AACGGTAACG ATGTCCGTAG CACCACAGTG

3551  GCTCGTCGTT TGGTATGGCT TCATTCAGCT CCGGTTCCCA ACGATCAAGG
      CGAGCAGCAA ACCATACCGA AGTAAGTCGA GGCCAAGGGT TGCTAGTTCC

3601  CGAGTTACAT GATCCCCCAT GTTGTGCAAA AAAGCGGTTA GCTCCTTCGG
      GCTCAATGTA CTAGGGGGTA CAACACGTTT TTTCGCCAAT CGAGGAAGCC

3651  TCCTCCGATC GTTGTCAGAA GTAAGTTGGC CGCAGTGTTA TCACTCATGG
      AGGAGGCTAG CAACAGTCTT CATTCAACCG GCGTCACAAT AGTGAGTACC
```

FIG. 1E

```
3701  TTATGGCAGC ACTGCATAAT TCTCTTACTG TCATGCCATC CGTAAGATGC
      AATACCGTCG TGACGTATTA AGAGAATGAC AGTACGGTAG GCATTCTACG

3751  TTTTCTGTGA CTGGTGAGTA CTCAACCAAG TCATTCTGAG AATAGTGTAT
      AAAAGACACT GACCACTCAT GAGTTGGTTC AGTAAGACTC TTATCACATA

3801  GCGGCGACCG AGTTGCTCTT GCCCGGCGTC AATACGGGAT AATACCGCGC
      CGCCGCTGGC TCAACGAGAA CGGGCCGCAG TTATGCCCTA TTATGGCGCG

3851  CACATAGCAG AACTTTAAAA GTGCTCATCA TTGGAAAACG TTCTTCGGGG
      GTGTATCGTC TTGAAATTTT CACGAGTAGT AACCTTTTGC AAGAAGCCCC

3901  CGAAAACTCT CAAGGATCTT ACCGCTGTTG AGATCCAGTT CGATGTAACC
      GCTTTTGAGA GTTCCTAGAA TGGCGACAAC TCTAGGTCAA GCTACATTGG

3951  CACTCGTGCA CCCAACTGAT CTTCAGCATC TTTTACTTTC ACCAGCGTTT
      GTGAGCACGT GGGTTGACTA GAAGTCGTAG AAAATGAAAG TGGTCGCAAA

4001  CTGGGTGAGC AAAAACAGGA AGGCAAAATG CCGCAAAAAA GGGAATAAGG
      GACCCACTCG TTTTTGTCCT TCCGTTTTAC GGCGTTTTTT CCCTTATTCC

4051  GCGACACGGA AATGTTGAAT ACTCATACTC TTCCTTTTTC AATATTATTG
      CGCTGTGCCT TTACAACTTA TGAGTATGAG AAGGAAAAAG TTATAATAAC

4101  AAGCATTTAT CAGGGTTATT GTCTCATGAG CGGATACATA TTTGAATGTA
      TTCGTAAATA GTCCCAATAA CAGAGTACTC GCCTATGTAT AAACTTACAT

4151  TTTAGAAAAA TAAACAAATA GGGGTTCCGC GCACATTTCC CCGAAAAGTG
      AAATCTTTTT ATTTGTTTAT CCCCAAGGCG CGTGTAAAGG GGCTTTTCAC

4201  CCACCTGACG TCTAAGAAAC CATTATTATC ATGACATTAA CCTATAAAAA
      GGTGGACTGC AGATTCTTTG GTAATAATAG TACTGTAATT GGATATTTTT

4251  TAGGCGTATC ACGAGGCCCT TTCGTC
      ATCCGCATAG TGCTCCGGGA AAGCAG
```

FIG. 1F

SEQ ID NO: 2

```
  →1  TCGCGCGTTT CGGTGATGAC GGTGAAAACC TCTGACACAT GCAGCTCCCG
      AGCGCGCAAA GCCACTACTG CCACTTTTGG AGACTGTGTA CGTCGAGGGC

51 GAGACGGTCA CAGCTTGTCT GTAAGCGGAT GCCGGGAGCA GACAAGCCCG
      CTCTGCCAGT GTCGAACAGA CATTCGCCTA CGGCCCTCGT CTGTTCGGGC

101 TCAGGGCGCG TCAGCGGGTG TTGGCGGGTG TCGGGGCTGG CTTAACTATG
      AGTCCCGCGC AGTCGCCCAC AACCGCCCAC AGCCCCGACC GAATTGATAC

HindIII
                                                  -------
  151 CGGCATCAGA GCAGATTGTA CTGAGAGTGC ACCATATGAA GCTTTTTGCA
      GCCGTAGTCT CGTCTAACAT GACTCTCACG TGGTATACTT CGAAAAACGT StuI
             -------
             AatI
             -------
  201 AAAGCCTAGG CCTCCAAAAA AGCCTCCTCA CTACTTCTGG AATAGCTCAG
      TTTCGGATCC GGAGGTTTTT TCGGAGGAGT GATGAAGACC TTATCGAGTC SfiI
            --------------
  251 AGGCCGAGGC GGCCTCGGCC TCTGCATAAA TAAAAAAAAT TAGTCAGCCA
      TCCGGCTCCG CCGGAGCCGG AGACGTATTT ATTTTTTTTA ATCAGTCGGT 301 TGGGGCGGAG AATGGGCGGA ACTGGGCGGG GAGGGAATTA TTGGCTATTG
      ACCCCGCCTC TTACCCGCCT TGACCCGCCC CTCCCTTAAT AACCGATAAC 351 GCCATTGCAT ACGTTGTATC TATATCATAA TATGTACATT TATATTGGCT
      CGGTAACGTA TGCAACATAG ATATAGTATT ATACATGTAA ATATAACCGA 401 CATGTCCAAT ATGACCGCCA TGTTGACATT GATTATTGAC TAGTTATTAA
      GTACAGGTTA TACTGGCGGT ACAACTGTAA CTAATAACTG ATCAATAATT 451 TAGTAATCAA TTACGGGGTC ATTAGTTCAT AGCCCATATA TGGAGTTCCG
      ATCATTAGTT AATGCCCCAG TAATCAAGTA TCGGGTATAT ACCTCAAGGC 501 CGTTACATAA CTTACGGTAA ATGGCCCGCC TGGCTGACCG CCCAACGACC
      GCAATGTATT GAATGCCATT TACCGGGCGG ACCGACTGGC GGGTTGCTGG 551 CCCGCCCATT GACGTCAATA ATGACGTATG TTCCCATAGT AACGCCAATA
      GGGCGGGTAA CTGCAGTTAT TACTGCATAC AAGGGTATCA TTGCGGTTAT 601 GGGACTTTCC ATTGACGTCA ATGGGTGGAG TATTTACGGT AAACTGCCCA
      CCCTGAAAGG TAACTGCAGT TACCCACCTC ATAAATGCCA TTTGACGGGT 651 CTTGGCAGTA CATCAAGTGT ATCATATGCC AAGTCCGCCC CCTATTGACG
      GAACCGTCAT GTAGTTCACA TAGTATACGG TTCAGGCGGG GGATAACTGC 701 TCAATGACGG TAAATGGCCC GCCTGGCATT ATGCCCAGTA CATGACCTTA
      AGTTACTGCC ATTTACCGGG CGGACCGTAA TACGGGTCAT GTACTGGAAT SnaBI
                                   -------
  751 CGGGACTTTC CTACTTGGCA GTACATCTAC GTATTAGTCA TCGCTATTAC
      GCCCTGAAAG GATGAACCGT CATGTAGATG CATAATCAGT AGCGATAATG
```

FIG. 2B

```
 801  CATGGTGATG CGGTTTTGGC AGTACACCAA TGGGCGTGGA TAGCGGTTTG
      GTACCACTAC GCCAAAACCG TCATGTGGTT ACCCGCACCT ATCGCCAAAC

851  ACTCACGGGG ATTTCCAAGT CTCCACCCCA TTGACGTCAA TGGGAGTTTG
      TGAGTGCCCC TAAAGGTTCA GAGGTGGGGT AACTGCAGTT ACCCTCAAAC

901  TTTTGGCACC AAAATCAACG GGACTTTCCA AAATGTCGTA ATAACCCCGC
      AAAACCGTGG TTTTAGTTGC CCTGAAAGGT TTTACAGCAT TATTGGGGCG

951  CCCGTTGACG CAAATGGGCG GTAGGCGTGT ACGGTGGGAG GTCTATATAA
      GGGCAACTGC GTTTACCCGC CATCCGCACA TGCCACCCTC CAGATATATT

1001  GCAGAGCTCG TTTAGTGAAC CGTCAGATCG CCTGGAGACG CCATCCACGC
      CGTCTCGAGC AAATCACTTG GCAGTCTAGC GGACCTCTGC GGTAGGTGCG
```
                                                        XmaIII
                                                        ------
                                                        SacII
                                                        -------
                                                        KspI
                                                        ------
                                                        EclXI
                                                        -------
                                                        EagI
                                                        ------
```
1051  TGTTTTGACC TCCATAGAAG ACACCGGGAC CGATCCAGCC TCCGCGGCCG
      ACAAAACTGG AGGTATCTTC TGTGGCCCTG GCTAGGTCGG AGGCGCCGGC

1101  GGAACGGTGC ATTGGAACGC GGATTCCCCG TGCCAAGAGT GACGTAAGTA
      CCTTGCCACG TAACCTTGCG CCTAAGGGGC ACGGTTCTCA CTGCATTCAT
```
                                              Ppl0I
                                              ------
                                              NsiI
                                              ------
```
1151  CCGCCTATAG ACTCTATAGG CACACCCCTT TGGCTCTTAT GCATGCTATA
      GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGTGA
      GACAAAAACC GAACCCCGGA TATGTGGGGG CGAGGAATAC GATATCCACT
```
        EspI
        --------
        CelII
        --------
        Bpu1102I
        --------
```
1251  TGGTATAGCT TAGCCTATAG GTGTGGGTTA TTGACCATTA TTGACCACTC
      ACCATATCGA ATCGGATATC CACACCCAAT AACTGGTAAT AACTGGTGAG

1301  CCCTATTGGT GACGATACTT TCCATTACTA ATCCATAACA TGGCTCTTTG
      GGGATAACCA CTGCTATGAA AGGTAATGAT TAGGTATTGT ACCGAGAAAC

1351  CCACAACTAT CTCTATTGGC TATATGCCAA TACTCTGTCC TTCAGAGACT
      GGTGTTGATA GAGATAACCG ATATACGGTT ATGAGACAGG AAGTCTCTGA

1401  GACACGGACT CTGTATTTTT ACAGGATGGG GTCCATTTAT TATTTACAAA
      CTGTGCCTGA GACATAAAAA TGTCCTACCC CAGGTAAATA ATAAATGTTT
```

FIG. 2C

```
1451  TTCACATATA CAACAACGCC GTCCCCCGTG CCCGCAGTTT TTATTAAACA
      AAGTGTATAT GTTGTTGCGG CAGGGGGCAC GGGCGTCAAA AATAATTTGT

MroI
                                                 ------
                                                 BspEI
                                                 ------
                                                 BseAI
                                                 ------
                                                 AccIII
                                                 ------
1501  TAGCGTGGGA TCTCCGACAT CTCGGGTACG TGTTCCGGAC ATGGGCTCTT
      ATCGCACCCT AGAGGCTGTA GAGCCCATGC ACAAGGCCTG TACCCGAGAA

1551  CTCCGGTAGC GGCGGAGCTT CCACATCCGA GCCCTGGTCC CATCCGTCCA
      GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA
      CGCCGAGTAC CAGCGAGCCG TCGAGGAACG AGGATTGTCA CCTCCGGTCT

1651  CTTAGGCACA GCACAATGCC CACCACCACC AGTGTGCCGC ACAAGGCCGT
      GAATCCGTGT CGTGTTACGG GTGGTGGTGG TCACACGGCG TGTTCCGGCA

1701  GGCGGTAGGG TATGTGTCTG AAAATGAGCT CGGAGATTGG GCTCGCACCT
      CCGCCATCCC ATACACAGAC TTTTACTCGA GCCTCTAACC CGAGCGTGGA

BfrI
                   --------
                   AflII                              PvuII
                   --------                           -----
1751  GGACGCAGAT GGAAGACTTA AGGCAGCGGC AGAAGAAGAT GCAGGCAGCT
      CCTGCGTCTA CCTTCTGAAT TCCGTCGCCG TCTTCTTCTA CGTCCGTCGA

PvuII                                           HpaI
      -                                               -
1801  GAGTTGTTGT ATTCTGATAA GAGTCAGAGG TAACTCCCGT TGCGGTGCTG
      CTCAACAACA TAAGACTATT CTCAGTCTCC ATTGAGGGCA ACGCCACGAC

HpaI
      -----
1851  TTAACGGTGG AGGGCAGTGT AGTCTGAGCA GTACTCGTTG CTGCCGCGCG
      AATTGCCACC TCCCGTCACA TCAGACTCGT CATGAGCAAC GACGGCGCGC

1901  CGCCACCAGA CATAATAGCT GACAGACTAA CAGACTGTTC CTTTCCATGG
      GCGGTGGTCT GTATTATCGA CTGTCTGATT GTCTGACAAG GAAAGGTACC

+2                              SEQ ID NO: 3—▷M   Q   W   N
                                       SalI
                                       ------
1951  GTCTTTTCTG CAGTCACCGT CGTCGACCTA AGAATTCATG CAGTGGAACT
      CAGAAAAGAC GTCAGTGGCA GCAGCTGGAT TCTTAAGTAT GTCACCTTGA

+2  S    T    A    F    H    Q   T    L    Q    D    P    R    V    R    G    L    Y
2001  CCACTGCCTT CCACCAAACT CTGCAGGATC CCAGAGTCAG GGGTCTGTAT
      GGTGACGGAA GGTGGTTTGA GACGTCCTAG GGTCTCAGTC CCCAGACATA

+2  L    P    A    G    G    S    S    G    T    V    N    P    A    P    N    I
2051  CTTCCTGCTG GTGGCTCCAG TTCAGGAACA GTAAACCCTG CTCCGAATAT
      GAAGGACGAC CACCGAGGTC AAGTCCTTGT CATTTGGGAC GAGGCTTATA
```

FIG. 2D

```
       +2    A  S  H     I  S  S  I     S  A  R     T  G  D     P  V  T
     2101  TGCCTCTCAC ATCTCGTCAA TCTCCGCGAG GACTGGGGAC CCTGTGACGA
           ACGGAGAGTG TAGAGCAGTT AGAGGCGCTC CTGACCCCTG GGACACTGCT

+2 N  M  E  N     I  T  S     G  F  L  G     P  L  L     V  L  Q
     2151  ACATGGAGAA CATCACATCA GGATTCCTAG GACCCCTGCT CGTGTTACAG
           TGTACCTCTT GTAGTGTAGT CCTAAGGATC CTGGGGACGA GCACAATGTC

+2    A  G  F  F     L  L  T     R  I  L     T  I  P     Q  S  L  D
     2201  GCGGGGTTTT TCTTGTTGAC AAGAATCCTC ACAATACCGC AGAGTCTAGA
           CGCCCCAAAA AGAACAACTG TTCTTAGGAG TGTTATGGCG TCTCAGATCT

+2       S  W  W     T  S  L  N     F  L  G     G  S  P     V  C  L
     2251  CTCGTGGTGG ACTTCTCTCA ATTTTCTAGG GGGATCTCCC GTGTGTCTTG
           GAGCACCACC TGAAGAGAGT TAAAAGATCC CCCTAGAGGG CACACAGAAC

+2 G  Q  N  S     Q  S  P     T  S  N     H  S  P  T     S  C  P
     2301  GCCAAAATTC GCAGTCCCCA ACCTCCAATC ACTCACCAAC CTCCTGTCCT
           CGGTTTTAAG CGTCAGGGGT TGGAGGTTAG TGAGTGGTTG GAGGACAGGA

+2    P  I  C  P     G  Y  R     W  M  C     L  R  R  F     I  I  F
     2351  CCAATTTGTC CTGGTTATCG CTGGATGTGT CTGCGGCGTT TTATCATATT
           GGTTAAACAG GACCAATAGC GACCTACACA GACGCCGCAA AATAGTATAA

+2    L  F  I     L  L  L  C     L  I  F     L  L  V     L  L  D
     2401  CCTCTTCATC CTGCTGCTAT GCCTCATCTT CTTATTGGTT CTTCTGGATT
           GGAGAAGTAG GACGACGATA CGGAGTAGAA GAATAACCAA GAAGACCTAA

+2 Y  Q  G  M     L  P  V     C  P  L     I  P  G  S     T  T  T
     2451  ATCAAGGTAT GTTGCCCGTT TGTCCTCTAA TTCCAGGATC AACAACAACC
           TAGTTCCATA CAACGGGCAA ACAGGAGATT AAGGTCCTAG TTGTTGTTGG

+2    S  T  G  P     C  K  T     C  T  T     P  A  Q     G  N  S  M
                           BstAPI
                        -----------
                             BspMI                     EcoNI
                           -------               -------------
     2501  AGTACGGGAC CATGCAAAAC CTGCACGACT CCTGCTCAAG GCAACTCTAT
           TCATGCCCTG GTACGTTTTG GACGTGCTGA GGACGAGTTC CGTTGAGATA
                                   BsgI
                                 ------

+2    F  P  S     C  C  C  T     K  P  T     D  G  N     C  T  C
     2551  GTTTCCCTCA TGTTGCTGTA CAAAACCTAC GGATGGAAAT TGCACCTGTA
           CAAAGGGAGT ACAACGACAT GTTTTGGATG CCTACCTTTA ACGTGGACAT

+2 I  P  I  P     S  S  W     A  F  A  K     Y  L  W     E  W  A
                              BstXI
                         -------------
     2601  TTCCCATCCC ATCGTCCTGG GCTTTCGCAA AATACCTATG GGAGTGGGCC
           AAGGGTAGGG TAGCAGGACC CGAAAGCGTT TTATGGATAC CCTCACCCGG

+2    S  V  R  F     S  W  L     S  L  L     V  P  F  V     Q  W  F
     2651  TCAGTCCGTT TCTCTTGGCT CAGTTTACTA GTGCCATTTG TTCAGTGGTT
           AGTCAGGCAA AGAGAACCGA GTCAAATGAT CACGGTAAAC AAGTCACCAA

+2    V  G  L     S  P  T  V     W  L  S     A  I  W     M  M  W
     2701  CGTAGGGCTT TCCCCCACTG TTTGGCTTTC AGCTATATGG ATGATGTGGT
           GCATCCCGAA AGGGGGTGAC AAACCGAAAG TCGATATACC TACTACACCA
```

FIG. 2E

```
        +2  Y   W   G   P     S   L   Y     S   I   V   S     P   F   I     P   L   L
     2751 ATTGGGGGCC AAGTCTGTAC AGCATCGTGA GTCCCTTTAT ACCGCTGTTA
          TAACCCCCGG TTCAGACATG TCGTAGCACT CAGGGAAATA TGGCGACAAT

+2  P   I   F   F     C   L   W     V   Y   I    *
                                           BstZ17 I              XhoI
                                           ------              ------
                                           Bst1107I            PaeR7I
                                           ------              ------
     2801 CCAATTTTCT TTTGTCTCTG GGTATACATT TAAGAATTCA GACTCGAGCA
          GGTTAAAAGA AAACAGAGAC CCATATGTAA ATTCTTAAGT CTGAGCTCGT

AscI       EcoRV                 MluI
                     --------   ------               -------
     2851 AGTCTAGAAA GGCGCGCCAA GATATCAAGG ATCCACTACG CGTTAGAGCT
          TCAGATCTTT CCGCGCGGTT CTATAGTTCC TAGGTGATGC CAATCTCGA

BclI
               ------
     2901 CGCTGATCAG CCTCGACTGT GCCTTCTAGT TGCCAGCCAT CTGTTGTTTG
          GCGACTAGTC GGAGCTGACA CGGAAGATCA ACGGTCGGTA GACAACAAAC

2951 CCCCTCCCCC GTGCCTTCCT TGACCCTGGA AGGTGCCACT CCCACTGTCC
          GGGGAGGGGG CACGGAAGGA ACTGGGACCT TCCACGGTGA GGGTGACAGG

3001 TTTCCTAATA AAATGAGGAA ATTGCATCGC ATTGTCTGAG TAGGTGTCAT
          AAAGGATTAT TTTACTCCTT TAACGTAGCG TAACAGACTC ATCCACAGTA

3051 TCTATTCTGG GGGGTGGGGT GGGGCAGGAC AGCAAGGGGG AGGATTGGGA
          AGATAAGACC CCCCACCCCA CCCCGTCCTG TCGTTCCCCC TCCTAACCCT

3101 AGACAATAGC AGGCATGCTG GGGAGCTCTT CCGCTTCCTC GCTCACTGAC
          TCTGTTATCG TCCGTACGAC CCCTCGAGAA GGCGAAGGAG CGAGTGACTG

3151 TCGCTGCGCT CGGTCGTTCG GCTGCGGCGA GCGGTATCAG CTCACTCAAA
          AGCGACGCGA GCCAGCAAGC CGACGCCGCT CGCCATAGTC GAGTGAGTTT

Pci I
                                                              ---
     3201 GGCGGTAATA CGGTTATCCA CAGAATCAGG GGATAACGCA GGAAAGAACA
          CCGCCATTAT GCCAATAGGT GTCTTAGTCC CCTATTGCGT CCTTTCTTGT

Pci I
          ---
     3251 TGTGAGCAAA AGGCCAGCAA AAGGCCAGGA ACCGTAAAAA GGCCGCGTTG
          ACACTCGTTT TCCGGTCGTT TTCCGGTCCT TGGCATTTTT CCGGCGCAAC

3301 CTGGCGTTTT TCCATAGGCT CCGCCCCCCT GACGAGCATC ACAAAAATCG
          GACCGCAAAA AGGTATCCGA GGCGGGGGGA CTGCTCGTAG TGTTTTTAGC

3351 ACGCTCAAGT CAGAGGTGGC GAAACCCGAC AGGACTATAA AGATACCAGG
          TGCGAGTTCA GTCTCCACCG CTTTGGGCTG TCCTGATATT TCTATGGTCC

3401 CGTTTCCCCC TGGAAGCTCC CTCGTGCGCT CTCCTGTTCC GACCCTGCCG
          GCAAAGGGGG ACCTTCGAGG GAGCACGCGA GAGGACAAGG CTGGGACGGC
```

FIG. 2F

```
                                                              HaeII
                                                              ------
3451   CTTACCGGAT ACCTGTCCGC CTTTCTCCCT TCGGGAAGCG TGGCGCTTTC
       GAATGGCCTA TGGACAGGCG GAAAGAGGGA AGCCCTTCGC ACCGCGAAAG

3501   TCAATGCTCA CGCTGTAGGT ATCTCAGTTC GGTGTAGGTC GTTCGCTCCA
       AGTTACGAGT GCGACATCCA TAGAGTCAAG CCACATCCAG CAAGCGAGGT

3551   AGCTGGGCTG TGTGCACGAA CCCCCCGTTC AGCCCGACCG CTGCGCCTTA
       TCGACCCGAC ACACGTGCTT GGGGGGCAAG TCGGGCTGGC GACGCGGAAT

3601   TCCGGTAACT ATCGTCTTGA GTCCAACCCG GTAAGACACG ACTTATCGCC
       AGGCCATTGA TAGCAGAACT CAGGTTGGGC CATTCTGTGC TGAATAGCGG

3651   ACTGGCAGCA GCCACTGGTA ACAGGATTAG CAGAGCGAGG TATGTAGGCG
       TGACCGTCGT CGGTGACCAT TGTCCTAATC GTCTCGCTCC ATACATCCGC

3701   GTGCTACAGA GTTCTTGAAG TGGTGGCCTA ACTACGGCTA CACTAGAAGG
       CACGATGTCT CAAGAACTTC ACCACCGGAT TGATGCCGAT GTGATCTTCC

3751   ACAGTATTTG GTATCTGCGC TCTGCTGAAG CCAGTTACCT TCGGAAAAAG
       TGTCATAAAC CATAGACGCG AGACGACTTC GGTCAATGGA AGCCTTTTC

3801   AGTTGGTAGC TCTTGATCCG GCAAACAAAC CACCGCTGGT AGCGGTGGTT
       TCAACCATCG AGAACTAGGC CGTTTGTTTG GTGGCGACCA TCGCCACCAA

3851   TTTTTGTTTG CAAGCAGCAG ATTACGCGCA GAAAAAAAGG ATCTCAAGAA
       AAAAACAAAC GTTCGTCGTC TAATGCGCGT CTTTTTTTCC TAGAGTTCTT

3901   GATCCTTTGA TCTTTTCTAC GGGGTCTGAC GCTCAGTGGA ACGAAAACTC
       CTAGGAAACT AGAAAAGATG CCCCAGACTG CGAGTCACCT TGCTTTTGAG

3951   ACGTTAAGGG ATTTTGGTCA TGAGATTATC AAAAAGGATC TTCACCTAGA
       TGCAATTCCC TAAAACCAGT ACTCTAATAG TTTTTCCTAG AAGTGGATCT

4001   TCCTTTTAAA TTAAAAATGA AGTTTTAAAT CAATCTAAAG TATATATGAG
       AGGAAAATTT AATTTTTACT TCAAAATTTA GTTAGATTTC ATATATACTC

4051   TAAACTTGGT CTGACAGTTA CCAATGCTTA ATCAGTGAGG CACCTATCTC
       ATTTGAACCA GACTGTCAAT GGTTACGAAT TAGTCACTCC GTGGATAGAG

Eam1105I
                                                          ------------
                                                          AspEI
                                                          ------------
4101   AGCGATCTGT CTATTTCGTT CATCCATAGT TGCCTGACTC CCCGTCGTGT
       TCGCTAGACA GATAAAGCAA GTAGGTATCA ACGGACTGAG GGGCAGCACA

4151   AGATAACTAC GATACGGGAG GGCTTACCAT CTGGCCCCAG TGCTGCAATG
       TCTATTGATG CTATGCCCTC CCGAATGGTA GACCGGGGTC ACGACGTTAC
```

FIG. 2G

```
                          Cfr10I
                          ------
                          BsrFI
                          ------
4201  ATACCGCGAG ACCCACGCTC ACCGGCTCCA GATTTATCAG CAATAAACCA
      TATGGCGCTC TGGGTGCGAG TGGCCGAGGT CTAAATAGTC GTTATTTGGT
                 BsaI
                 -------

4251  GCCAGCCGGA AGGGCCGAGC GCAGAAGTGG TCCTGCAACT TTATCCGCCT
      CGGTCGGCCT TCCCGGCTCG CGTCTTCACC AGGACGTTGA AATAGGCGGA

4301  CCATCCAGTC TATTAATTGT TGCCGGGAAG CTAGAGTAAG TAGTTCGCCA
      GGTAGGTCAG ATAATTAACA ACGGCCCTTC GATCTCATTC ATCAAGCGGT

FspI
                  ------
                  AviII
                  ------
                  AosI
                  ------
4351  GTTAATAGTT TGCGCAACGT TGTTGCCATT GCTACAGGCA TCGTGGTGTC
      CAATTATCAA ACGCGTTGCA ACAACGGTAA CGATGTCCGT AGCACCACAG

4401  ACGCTCGTCG TTTGGTATGG CTTCATTCAG CTCCGGTTCC CAACGATCAA
      TGCGAGCAGC AAACCATACC GAAGTAAGTC GAGGCCAAGG GTTGCTAGTT

4451  GGCGAGTTAC ATGATCCCCC ATGTTGTGCA AAAAAGCGGT TAGCTCCTTC
      CCGCTCAATG TACTAGGGGG TACAACACGT TTTTTCGCCA ATCGAGGAAG

PvuI
                    -------
4501  GGTCCTCCGA TCGTTGTCAG AAGTAAGTTG GCCGCAGTGT TATCACTCAT
      CCAGGAGGCT AGCAACAGTC TTCATTCAAC CGGCGTCACA ATAGTGAGTA

4551  GGTTATGGCA GCACTGCATA ATTCTCTTAC TGTCATGCCA TCCGTAAGAT
      CCAATACCGT CGTGACGTAT TAAGAGAATG ACAGTACGGT AGGCATTCTA

4601  GCTTTTCTGT GACTGGTGAG TACTCAACCA AGTCATTCTG AGAATAGTGT
      CGAAAAGACA CTGACCACTC ATGAGTTGGT TCAGTAAGAC TCTTATCACA

BcgI
             -------------
4651  ATGCGGCGAC CGAGTTGCTC TTGCCCGGCG TCAATACGGG ATAATACCGC
      TACGCCGCTG GCTCAACGAG AACGGGCCGC AGTTATGCCC TATTATGGCG

XmnI
                                       -----------
                                       Asp700
                                       -----------
4701  GCCACATAGC AGAACTTTAA AAGTGCTCAT CATTGGAAAA CGTTCTTCGG
      CGGTGTATCG TCTTGAAATT TTCACGAGTA GTAACCTTTT GCAAGAAGCC

4751  GGCGAAAACT CTCAAGGATC TTACCGCTGT TGAGATCCAG TTCGATGTAA
      CCGCTTTTGA GAGTTCCTAG AATGGCGACA ACTCTAGGTC AAGCTACATT

4801  CCCACTCGTG CACCCAACTG ATCTTCAGCA TCTTTTACTT TCACCAGCGT
      GGGTGAGCAC GTGGGTTGAC TAGAAGTCGT AGAAAATGAA AGTGGTCGCA
```

FIG. 2H

```
4851  TTCTGGGTGA GCAAAAACAG GAAGGCAAAA TGCCGCAAAA AAGGGAATAA
      AAGACCCACT CGTTTTTGTC CTTCCGTTTT ACGGCGTTTT TTCCCTTATT

4901  GGGCGACACG GAAATGTTGA ATACTCATAC TCTTCCTTTT TCAATATTAT
      CCCGCTGTGC CTTTACAACT TATGAGTATG AGAAGGAAAA AGTTATAATA

4951  TGAAGCATTT ATCAGGGTTA TTGTCTCATG AGCGGATACA TATTTGAATG
      ACTTCGTAAA TAGTCCCAAT AACAGAGTAC TCGCCTATGT ATAAACTTAC

5001  TATTTAGAAA AATAAACAAA TAGGGGTTCC GCGCACATTT CCCCGAAAAG
      ATAAATCTTT TTATTTGTTT ATCCCCAAGG CGCGTGTAAA GGGGCTTTTC

5051  TGCCACCTGA CGTCTAAGAA ACCATTATTA TCATGACATT AACCTATAAA
      ACGGTGGACT GCAGATTCTT TGGTAATAAT AGTACTGTAA TTGGATATTT

5101  AATAGGCGTA TCACGAGGCC CTTTCGTC
      TTATCCGCAT AGTGCTCCGG GAAAGCAG
```

FIG. 21

SEQ ID NO: 4

```
  1  TCGCGCGTTT CGGTGATGAC GGTGAAAACC TCTGACACAT GCAGCTCCCG
     AGCGCGCAAA GCCACTACTG CCACTTTTGG AGACTGTGTA CGTCGAGGGC

51  GAGACGGTCA CAGCTTGTCT GTAAGCGGAT GCCGGGAGCA GACAAGCCCG
     CTCTGCCAGT GTCGAACAGA CATTCGCCTA CGGCCCTCGT CTGTTCGGGC

101  TCAGGGCGCG TCAGCGGGTG TTGGCGGGTG TCGGGGCTGG CTTAACTATG
     AGTCCCGCGC AGTCGCCCAC AACCGCCCAC AGCCCCGACC GAATTGATAC

HindIII
                                                  -------
151  CGGCATCAGA GCAGATTGTA CTGAGAGTGC ACCATATGAA GCTTTTTGCA
     GCCGTAGTCT CGTCTAACAT GACTCTCACG TGGTATACTT CGAAAAACGT StuI
         -------
         AatI
         -------
201  AAAGCCTAGG CCTCCAAAAA AGCCTCCTCA CTACTTCTGG AATAGCTCAG
     TTTCGGATCC GGAGGTTTTT TCGGAGGAGT GATGAAGACC TTATCGAGTC SfiI
         --------------
251  AGGCCGAGGC GGCCTCGGCC TCTGCATAAA TAAAAAAAAT TAGTCAGCCA
     TCCGGCTCCG CCGGAGCCGG AGACGTATTT ATTTTTTTTA ATCAGTCGGT 301  TGGGGCGGAG AATGGGCGGA ACTGGGCGGG GAGGGAATTA TTGGCTATTG
     ACCCCGCCTC TTACCCGCCT TGACCCGCCC CTCCCTTAAT AACCGATAAC 351  GCCATTGCAT ACGTTGTATC TATATCATAA TATGTACATT TATATTGGCT
     CGGTAACGTA TGCAACATAG ATATAGTATT ATACATGTAA ATATAACCGA 401  CATGTCCAAT ATGACCGCCA TGTTGACATT GATTATTGAC TAGTTATTAA
     GTACAGGTTA TACTGGCGGT ACAACTGTAA CTAATAACTG ATCAATAATT 451  TAGTAATCAA TTACGGGGTC ATTAGTTCAT AGCCCATATA TGGAGTTCCG
     ATCATTAGTT AATGCCCCAG TAATCAAGTA TCGGGTATAT ACCTCAAGGC 501  CGTTACATAA CTTACGGTAA ATGGCCCGCC TGGCTGACCG CCCAACGACC
     GCAATGTATT GAATGCCATT TACCGGGCGG ACCGACTGGC GGGTTGCTGG 551  CCCGCCCATT GACGTCAATA ATGACGTATG TTCCCATAGT AACGCCAATA
     GGGCGGGTAA CTGCAGTTAT TACTGCATAC AAGGGTATCA TTGCGGTTAT 601  GGGACTTTCC ATTGACGTCA ATGGGTGGAG TATTTACGGT AAACTGCCCA
     CCCTGAAAGG TAACTGCAGT TACCCACCTC ATAAATGCCA TTTGACGGGT 651  CTTGGCAGTA CATCAAGTGT ATCATATGCC AAGTCCGCCC CCTATTGACG
     GAACCGTCAT GTAGTTCACA TAGTATACGG TTCAGGCGGG GGATAACTGC 701  TCAATGACGG TAAATGGCCC GCCTGGCATT ATGCCCAGTA CATGACCTTA
     AGTTACTGCC ATTTACCGGG CGGACCGTAA TACGGGTCAT GTACTGGAAT SnaBI
                                        -------
751  CGGGACTTTC CTACTTGGCA GTACATCTAC GTATTAGTCA TCGCTATTAC
     GCCCTGAAAG GATGAACCGT CATGTAGATG CATAATCAGT AGCGATAATG
```

FIG. 3B

```
 801  CATGGTGATG CGGTTTTGGC AGTACACCAA TGGGCGTGGA TAGCGGTTTG
      GTACCACTAC GCCAAAACCG TCATGTGGTT ACCCGCACCT ATCGCCAAAC

851  ACTCACGGGG ATTTCCAAGT CTCCACCCCA TTGACGTCAA TGGGAGTTTG
      TGAGTGCCCC TAAAGGTTCA GAGGTGGGGT AACTGCAGTT ACCCTCAAAC

901  TTTTGGCACC AAAATCAACG GGACTTTCCA AAATGTCGTA ATAACCCCGC
      AAAACCGTGG TTTTAGTTGC CCTGAAAGGT TTTACAGCAT TATTGGGGCG

951  CCCGTTGACG CAAATGGGCG GTAGGCGTGT ACGGTGGGAG GTCTATATAA
      GGGCAACTGC GTTTACCCGC CATCCGCACA TGCCACCCTC CAGATATATT

1001  GCAGAGCTCG TTTAGTGAAC CGTCAGATCG CCTGGAGACG CCATCCACGC
      CGTCTCGAGC AAATCACTTG GCAGTCTAGC GGACCTCTGC GGTAGGTGCG

XmaIII
                                                  ------
                                                  SacII
                                                  ------
                                                  KspI
                                                  ------
                                                  EclXI
                                                  ------
                                                  EagI
                                                  ------
1051  TGTTTTGACC TCCATAGAAG ACACCGGGAC CGATCCAGCC TCCGCGGCCG
      ACAAAACTGG AGGTATCTTC TGTGGCCCTG GCTAGGTCGG AGGCGCCGGC

1101  GGAACGGTGC ATTGGAACGC GGATTCCCCG TGCCAAGAGT GACGTAAGTA
      CCTTGCCACG TAACCTTGCG CCTAAGGGGC ACGGTTCTCA CTGCATTCAT

PpuI 0I
                                       ------
                                       NsiI
                                       ------
1151  CCGCCTATAG ACTCTATAGG CACACCCCTT TGGCTCTTAT GCATGCTATA
      GGCGGATATC TGAGATATCC GTGTGGGGAA ACCGAGAATA CGTACGATAT

1201  CTGTTTTTGG CTTGGGGCCT ATACACCCCC GCTCCTTATG CTATAGGTGA
      GACAAAAACC GAACCCCGGA TATGTGGGGG CGAGGAATAC GATATCCACT

EspI
       --------
       CelII
       --------
       Bpu1102I
       --------
1251  TGGTATAGCT TAGCCTATAG GTGTGGGTTA TTGACCATTA TTGACCACTC
      ACCATATCGA ATCGGATATC CACACCCAAT AACTGGTAAT AACTGGTGAG

1301  CCCTATTGGT GACGATACTT TCCATTACTA ATCCATAACA TGGCTCTTTG
      GGGATAACCA CTGCTATGAA AGGTAATGAT TAGGTATTGT ACCGAGAAAC

1351  CCACAACTAT CTCTATTGGC TATATGCCAA TACTCTGTCC TTCAGAGACT
      GGTGTTGATA GAGATAACCG ATATACGGTT ATGAGACAGG AAGTCTCTGA

1401  GACACGGACT CTGTATTTTT ACAGGATGGG GTCCATTTAT TATTTACAAA
      CTGTGCCTGA GACATAAAAA TGTCCTACCC CAGGTAAATA ATAAATGTTT
```

FIG. 3C

```
1451  TTCACATATA CAACAACGCC GTCCCCCGTG CCCGCAGTTT TTATTAAACA
      AAGTGTATAT GTTGTTGCGG CAGGGGGCAC GGGCGTCAAA AATAATTTGT

MroI
                                       ------
                                       BspEI
                                       ------
                                       BseAI
                                       ------
                                       AccIII
                                       ------
1501  TAGCGTGGGA TCTCCGACAT CTCGGGTACG TGTTCCGGAC ATGGGCTCTT
      ATCGCACCCT AGAGGCTGTA GAGCCCATGC ACAAGGCCTG TACCCGAGAA

1551  CTCCGGTAGC GGCGGAGCTT CCACATCCGA GCCCTGGTCC CATCCGTCCA
      GAGGCCATCG CCGCCTCGAA GGTGTAGGCT CGGGACCAGG GTAGGCAGGT

1601  GCGGCTCATG GTCGCTCGGC AGCTCCTTGC TCCTAACAGT GGAGGCCAGA
      CGCCGAGTAC CAGCGAGCCG TCGAGGAACG AGGATTGTCA CCTCCGGTCT

1651  CTTAGGCACA GCACAATGCC CACCACCACC AGTGTGCCGC ACAAGGCCGT
      GAATCCGTGT CGTGTTACGG GTGGTGGTGG TCACACGGCG TGTTCCGGCA

1701  GGCGGTAGGG TATGTGTCTG AAAATGAGCT CGGAGATTGG GCTCGCACCT
      CCGCCATCCC ATACACAGAC TTTTACTCGA GCCTCTAACC CGAGCGTGGA

BfrI
                 -------
                 AflII
                 -------
1751  GGACGCAGAT GGAAGACTTA AGGCAGCGGC AGAAGAAGAT GCAGGCAGCT
      CCTGCGTCTA CCTTCTGAAT TCCGTCGCCG TCTTCTTCTA CGTCCGTCGA

HpaI
                                                        -
1801  GAGTTGTTGT ATTCTGATAA GAGTCAGAGG TAACTCCCGT TGCGGTGCTG
      CTCAACAACA TAAGACTATT CTCAGTCTCC ATTGAGGGCA ACGCCACGAC

HpaI
      -----
1851  TTAACGGTGG AGGGCAGTGT AGTCTGAGCA GTACTCGTTG CTGCCGCGCG
      AATTGCCACC TCCCGTCACA TCAGACTCGT CATGAGCAAC GACGGCGCGC

1901  CGCCACCAGA CATAATAGCT GACAGACTAA CAGACTGTTC CTTTCCATGG
      GCGGTGGTCT GTATTATCGA CTGTCTGATT GTCTGACAAG GAAAGGTACC

+3                               SEQ ID NO: 5 ──▷  M  D  A
                                       SalI
                                       ------
1951  GTCTTTTCTG CAGTCACCGT CGTCGACGAA TTCAAGCAAT CATGGATGCA
      CAGAAAAGAC GTCAGTGGCA GCAGCTGCTT AAGTTCGTTA GTACCTACGT

+3  M  K  R  G  L  C  C  V  L  L  L  C  G  A  V  F  V
2001  ATGAAGAGAG GGCTCTGCTG TGTGCTGCTG CTGTGTGGAG CAGTCTTCGT
      TACTTCTCTC CCGAGACGAC ACACGACGAC GACACACCTC GTCAGAAGCA
```

FIG. 3D

```
           +3      S   P   S     A   S   Y     Q   V   R     N   S   T     G   L   Y   H
                                NheI                                                    PmlI
                                ------                                                  ----
                        Eco47III                                                        PmaCI
                        --------                                                        ----
                        Afe I         SexAI                                             BbrPI
                        --------      ---------                                         ----
           2051   TTCGCCCAGC GCTAGCTACC AGGTGCGCAA CAGCACCGGC CTGTACCACG
                  AAGCGGGTCG CGATCGATGG TCCACGCGTT GTCGTGGCCG GACATGGTGC

+3      V   T   N   D     C   P   N     S   S   I   V     Y   E   A   A   D   A
                  PmlI
                  --
                  PmaCI
                  --
                  BbrPI
                  --
           2101   TGACCAACGA CTGCCCCAAC AGCAGCATCG TGTACGAGGC CGCCGACGCC
                  ACTGGTTGCT GACGGGGTTG TCGTCGTAGC ACATGCTCCG GCGGCTGCGG

+3      I   L   H   T     P   G   C     V   P   C     V   R   E     G   N   A   S
           2151   ATCCTGCACA CCCCCGGCTG CGTGCCCTGC GTGCGCGAGG GCAACGCCAG
                  TAGGACGTGT GGGGGCCGAC GCACGGGACG CACGCGCTCC CGTTGCGGTC

+3      R   C   W     V   A   M   T     P   T   V     A   T   R     D   G   K
           2201   CCGCTGCTGG GTGGCCATGA CCCCCACCGT GGCCACCCGC GACGGCAAGC
                  GGCGACGACC CACCGGTACT GGGGGTGGCA CCGGTGGGCG CTGCCGTTCG

+3      L   P   A   T     Q   L   R     R   H   I   D     L   L   V     G   S   A
                                                                                    DraIII
                                                                                    -
           2251   TGCCCGCCAC CCAGCTGCGC CGCCACATCG ACCTGCTGGT GGGCAGCGCC
                  ACGGGCGGTG GGTCGACGCG GCGGTGTAGC TGGACGACCA CCCGTCGCGG

+3      T   L   C     S   A   L   Y     V   G   D     L   C   G   S     V   F   L
                  DraIII
                  --------
           2301   ACCCTGTGCA GCGCCCTGTA CGTGGGCGAC CTGTGCGGCA GCGTGTTCCT
                  TGGGACACGT CGCGGGACAT GCACCCGCTG GACACGCCGT CGCACAAGGA

+3      V   G   Q     L   F   T   F     S   P   R     R   H   W     T   T   Q
           2351   GGTGGGCCAG CTGTTCACCT TCAGCCCCCG CCGCCACTGG ACCACCCAGG
                  CCACCCGGTC GACAAGTGGA AGTCGGGGGC GGCGGTGACC TGGTGGGTCC

+3      G   C   N   C     S   I   Y     P   G   H   I     T   G   H     R   M   A
           2401   GCTGCAACTG CAGCATCTAC CCCGGCCACA TCACCGGCCA CCGCATGGCC
                  CGACGTTGAC GTCGTAGATG GGGCCGGTGT AGTGGCCGGT GGCGTACCGG
                                                                340-----SAg
           +3      W   D   M   M     M   N   W     S   P   T     T  |M   E   N     I   T   S
           2451   TGGGACATGA TGATGAACTG GAGCCCCACC ACC|ATGGAGA ACATCACATC
                  ACCCTGTACT ACTACTTGAC CTCGGGGTGG TGG|TACCTCT TGTAGTGTAG

+3      G   F   L     G   P   L   L     V   L   Q     A   G   F     F   L   L
                              PpuMI
                              ---------
           2501   AGGATTCCTA GGACCCCTGC TCGTGTTACA GGCGGGGTTT TTCTTGTTGA
                  TCCTAAGGAT CCTGGGGACG AGCACAATGT CCGCCCCAAA AAGAACAACT
```

FIG. 3E

```
       +3   T   R   I   L    T   I   P    Q   S   L   D   S   W   W    T   S   L
      2551  CAAGAATCCT CACAATACCG CAGAGTCTAG ACTCGTGGTG GACTTCTCTC
            GTTCTTAGGA GTGTTATGGC GTCTCAGATC TGAGCACCAC CTGAAGAGAG

+3   N   F   L   G    G   S   P    V   C   L    G   Q   N    S   Q   S   P
      2601  AATTTTCTAG GGGGATCTCC CGTGTGTCTT GGCCAAAATT CGCAGTCCCC
            TTAAAAGATC CCCCTAGAGG GCACACAGAA CCGGTTTTAA GCGTCAGGGG

+3    T   S   N    H   S   P   T    S   C   P    P   I   C    P   G   Y
      2651  AACCTCCAAT CACTCACCAA CCTCCTGTCC TCCAATTTGT CCTGGTTATC
            TTGGAGGTTA GTGAGTGGTT GGAGGACAGG AGGTTAAACA GGACCAATAG

+3   R   W   M   C    L   R   R    F   I   I   F    L   F   I    L   L   L
      2701  GCTGGATGTG TCTGCGGCGT TTTATCATAT TCCTCTTCAT CCTGCTGCTA
            CGACCTACAC AGACGCCGCA AAATAGTATA AGGAGAAGTA GGACGACGAT

+3   C   L   I   F    L   L   V    L   L   D    Y   Q   G   M    L   P   V
      2751  TGCCTCATCT TCTTATTGGT TCTTCTGGAT TATCAAGGTA TGTTGCCCGT
            ACGGAGTAGA AGAATAACCA AGAAGACCTA ATAGTTCCAT ACAACGGGCA

+3    C   P   L    I   P   G   S    T   T   T    S   T   G    P   C   K
                                                                       BstAPI
                                                                       -----
      2801  TTGTCCTCTA ATTCCAGGAT CAACAACAAC CAGTACGGGA CCATGCAAAA
            AACAGGAGAT TAAGGTCCTA GTTGTTGTTG GTCATGCCCT GGTACGTTTT

+3   T   C   T   T    P   A   Q    G   N   S   M    F   P   S    C   C   C
            BstAP I               EcoNI
            -----                 ------------
      2851  CCTGCACGAC TCCTGCTCAA GGCAACTCTA TGTTTCCCTC ATGTTGCTGT
            GGACGTGCTG AGGACGAGTT CCGTTGAGAT ACAAAGGGAG TACAACGACA

+3   T   K   P   T    D   G   N    C   T   C    I   P   I   P    S   S   W
      2901  ACAAAACCTA CGGATGGAAA TTGCACCTGT ATTCCCATCC CATCGTCCTG
            TGTTTTGGAT GCCTACCTTT AACGTGGACA TAAGGGTAGG GTAGCAGGAC

+3    A   F   A    K   Y   L   W    E   W   A    S   V   R    F   S   W
      2951  GGCTTTCGCA AAATACCTAT GGGAGTGGGC CTCAGTCCGT TTCTCTTGGC
            CCGAAAGCGT TTTATGGATA CCCTCACCCG GAGTCAGGCA AAGAGAACCG

+3   L   S   L   L    V   P   F    V   Q   W   F    V   G   L    S   P   T
      3001  TCAGTTTACT AGTGCCATTT GTTCAGTGGT TCGTAGGGCT TTCCCCCACT
            AGTCAAATGA TCACGGTAAA CAAGTCACCA AGCATCCCGA AAGGGGGTGA

+3   V   W   L   S    A   I   W    M   M   W    Y   W   G   P    S   L   Y
      3051  GTTTGGCTTT CAGCTATATG GATGATGTGG TATTGGGGGC CAAGTCTGTA
            CAAACCGAAA GTCGATATAC CTACTACACC ATAACCCCCG GTTCAGACAT

+3    S   I   V    S   P   F   I    P   L   L    P   I   F    F   C   L
      3101  CAGCATCGTG AGTCCCTTTA TACCGCTGTT ACCAATTTTC TTTTGTCTCT
            GTCGTAGCAC TCAGGGAAAT ATGGCGACAA TGGTTAAAAG AAAACAGAGA

+3   W   V   Y   I    *
            BstZ17 I                         XhoI
            ------                           ------
            Bst1107I                         PaeR7I                    AscI
            ------                           ------                    --------
      3151  GGGTATACAT TTAAGAATTC AGACTCGAGC AAGTCTAGAA AGGCGCGCCA
            CCCATATGTA AATTCTTAAG TCTGAGCTCG TTCAGATCTT TCCGCGCGGT
```

FIG. 3F

```
              EcoRV      BamHI      MluI                  BclI
              ------    -------    -------               ------
       3201   AGATATCAAG GATCCACTAC GCGTTAGAGC TCGCTGATCA GCCTCGACTG
              TCTATAGTTC CTAGGTGATG CGCAATCTCG AGCGACTAGT CGGAGCTGAC

3251   TGCCTTCTAG TTGCCAGCCA TCTGTTGTTT GCCCCTCCCC CGTGCCTTCC
              ACGGAAGATC AACGGTCGGT AGACAACAAA CGGGGAGGGG GCACGGAAGG

3301   TTGACCCTGG AAGGTGCCAC TCCCACTGTC CTTTCCTAAT AAAATGAGGA
              AACTGGGACC TTCCACGGTG AGGGTGACAG GAAAGGATTA TTTTACTCCT

3351   AATTGCATCG CATTGTCTGA GTAGGTGTCA TTCTATTCTG GGGGGTGGGG
              TTAACGTAGC GTAACAGACT CATCCACAGT AAGATAAGAC CCCCCACCCC

3401   TGGGGCAGGA CAGCAAGGGG GAGGATTGGG AAGACAATAG CAGGCATGCT
              ACCCCGTCCT GTCGTTCCCC CTCCTAACCC TTCTGTTATC GTCCGTACGA

3451   GGGGAGCTCT TCCGCTTCCT CGCTCACTGA CTCGCTGCGC TCGGTCGTTC
              CCCCTCGAGA AGGCGAAGGA GCGAGTGACT GAGCGACGCG AGCCAGCAAG

3501   GGCTGCGGCG AGCGGTATCA GCTCACTCAA AGGCGGTAAT ACGGTTATCC
              CCGACGCCGC TCGCCATAGT CGAGTGAGTT TCCGCCATTA TGCCAATAGG

Pci I
                                             -------
       3551   ACAGAATCAG GGGATAACGC AGGAAAGAAC ATGTGAGCAA AAGGCCAGCA
              TGTCTTAGTC CCCTATTGCG TCCTTTCTTG TACACTCGTT TTCCGGTCGT

3601   AAAGGCCAGG AACCGTAAAA AGGCCGCGTT GCTGGCGTTT TTCCATAGGC
              TTTCCGGTCC TTGGCATTTT TCCGGCGCAA CGACCGCAAA AAGGTATCCG

3651   TCCGCCCCCC TGACGAGCAT CACAAAAATC GACGCTCAAG TCAGAGGTGG
              AGGCGGGGGG ACTGCTCGTA GTGTTTTTAG CTGCGAGTTC AGTCTCCACC

3701   CGAAACCCGA CAGGACTATA AAGATACCAG GCGTTTCCCC CTGGAAGCTC
              GCTTTGGGCT GTCCTGATAT TTCTATGGTC CGCAAAGGGG GACCTTCGAG

3751   CCTCGTGCGC TCTCCTGTTC CGACCCTGCC GCTTACCGGA TACCTGTCCG
              GGAGCACGCG AGAGGACAAG GCTGGGACGG CGAATGGCCT ATGGACAGGC

3801   CCTTTCTCCC TTCGGGAAGC GTGGCGCTTT CTCAATGCTC ACGCTGTAGG
              GGAAAGAGGG AAGCCCTTCG CACCGCGAAA GAGTTACGAG TGCGACATCC

3851   TATCTCAGTT CGGTGTAGGT CGTTCGCTCC AAGCTGGGCT GTGTGCACGA
              ATAGAGTCAA GCCACATCCA GCAAGCGAGG TTCGACCCGA CACACGTGCT

3901   ACCCCCCGTT CAGCCCGACC GCTGCGCCTT ATCCGGTAAC TATCGTCTTG
              TGGGGGGCAA GTCGGGCTGG CGACGCGGAA TAGGCCATTG ATAGCAGAAC

3951   AGTCCAACCC GGTAAGACAC GACTTATCGC CACTGGCAGC AGCCACTGGT
              TCAGGTTGGG CCATTCTGTG CTGAATAGCG GTGACCGTCG TCGGTGACCA

4001   AACAGGATTA GCAGAGCGAG GTATGTAGGC GGTGCTACAG AGTTCTTGAA
              TTGTCCTAAT CGTCTCGCTC CATACATCCG CCACGATGTC TCAAGAACTT

4051   GTGGTGGCCT AACTACGGCT ACACTAGAAG GACAGTATTT GGTATCTGCG
              CACCACCGGA TTGATGCCGA TGTGATCTTC CTGTCATAAA CCATAGACGC
```

FIG. 3G

```
4101  CTCTGCTGAA GCCAGTTACC TTCGGAAAAA GAGTTGGTAG CTCTTGATCC
      GAGACGACTT CGGTCAATGG AAGCCTTTTT CTCAACCATC GAGAACTAGG

4151  GGCAAACAAA CCACCGCTGG TAGCGGTGGT TTTTTTGTTT GCAAGCAGCA
      CCGTTTGTTT GGTGGCGACC ATCGCCACCA AAAAACAAA CGTTCGTCGT

4201  GATTACGCGC AGAAAAAAAG GATCTCAAGA AGATCCTTTG ATCTTTTCTA
      CTAATGCGCG TCTTTTTTTC CTAGAGTTCT TCTAGGAAAC TAGAAAAGAT

4251  CGGGGTCTGA CGCTCAGTGG AACGAAAACT CACGTTAAGG GATTTTGGTC
      GCCCCAGACT GCGAGTCACC TTGCTTTTGA GTGCAATTCC CTAAAACCAG

4301  ATGAGATTAT CAAAAAGGAT CTTCACCTAG ATCCTTTTAA ATTAAAAATG
      TACTCTAATA GTTTTTCCTA GAAGTGGATC TAGGAAAATT TAATTTTTAC

4351  AAGTTTTAAA TCAATCTAAA GTATATATGA GTAAACTTGG TCTGACAGTT
      TTCAAAATTT AGTTAGATTT CATATATACT CATTTGAACC AGACTGTCAA

4401  ACCAATGCTT AATCAGTGAG GCACCTATCT CAGCGATCTG TCTATTTCGT
      TGGTTACGAA TTAGTCACTC CGTGGATAGA GTCGCTAGAC AGATAAAGCA

Eam1105I
                  ------------
                     AspEI
                  ------------
4451  TCATCCATAG TTGCCTGACT CCCCGTCGTG TAGATAACTA CGATACGGGA
      AGTAGGTATC AACGGACTGA GGGGCAGCAC ATCTATTGAT GCTATGCCCT

4501  GGGCTTACCA TCTGGCCCCA GTGCTGCAAT GATACCGCGA GACCCACGCT
      CCCGAATGGT AGACCGGGGT CACGACGTTA CTATGGCGCT CTGGGTGCGA
                                                     BsaI
                                                  -------

4551  CACCGGCTCC AGATTTATCA GCAATAAACC AGCCAGCCGG AAGGGCCGAG
      GTGGCCGAGG TCTAAATAGT CGTTATTTGG TCGGTCGGCC TTCCCGGCTC

4601  CGCAGAAGTG GTCCTGCAAC TTTATCCGCC TCCATCCAGT CTATTAATTG
      GCGTCTTCAC CAGGACGTTG AAATAGGCGG AGGTAGGTCA GATAATTAAC

4651  TTGCCGGGAA GCTAGAGTAA GTAGTTCGCC AGTTAATAGT TTGCGCAACG
      AACGGCCCTT CGATCTCATT CATCAAGCGG TCAATTATCA AACGCGTTGC

4701  TTGTTGCCAT TGCTACAGGC ATCGTGGTGT CACGCTCGTC GTTTGGTATG
      AACAACGGTA ACGATGTCCG TAGCACCACA GTGCGAGCAG CAAACCATAC

4751  GCTTCATTCA GCTCCGGTTC CCAACGATCA AGGCGAGTTA CATGATCCCC
      CGAAGTAAGT CGAGGCCAAG GGTTGCTAGT TCCGCTCAAT GTACTAGGGG
                                                    PvuI
                                                  -------
4801  CATGTTGTGC AAAAAAGCGG TTAGCTCCTT CGGTCCTCCG ATCGTTGTCA
      GTACAACACG TTTTTTCGCC AATCGAGGAA GCCAGGAGGC TAGCAACAGT

4851  GAAGTAAGTT GGCCGCAGTG TTATCACTCA TGGTTATGGC AGCACTGCAT
      CTTCATTCAA CCGGCGTCAC AATAGTGAGT ACCAATACCG TCGTGACGTA

4901  AATTCTCTTA CTGTCATGCC ATCCGTAAGA TGCTTTTCTG TGACTGGTGA
      TTAAGAGAAT GACAGTACGG TAGGCATTCT ACGAAAAGAC ACTGACCACT
```

FIG. 3H

```
                                                      BcgI
                                                  ------------
4951  GTACTCAACC AAGTCATTCT GAGAATAGTG TATGCGGCGA CCGAGTTGCT
      CATGAGTTGG TTCAGTAAGA CTCTTATCAC ATACGCCGCT GGCTCAACGA

5001  CTTGCCCGGC GTCAATACGG GATAATACCG CGCCACATAG CAGAACTTTA
      GAACGGGCCG CAGTTATGCC CTATTATGGC GCGGTGTATC GTCTTGAAAT

XmnI
                       -----------
                         Asp700
                       -----------
5051  AAAGTGCTCA TCATTGGAAA ACGTTCTTCG GGGCGAAAAC TCTCAAGGAT
      TTTCACGAGT AGTAACCTTT TGCAAGAAGC CCCGCTTTTG AGAGTTCCTA

5101  CTTACCGCTG TTGAGATCCA GTTCGATGTA ACCCACTCGT GCACCCAACT
      GAATGGCGAC AACTCTAGGT CAAGCTACAT TGGGTGAGCA CGTGGGTTGA

5151  GATCTTCAGC ATCTTTTACT TTCACCAGCG TTTCTGGGTG AGCAAAAACA
      CTAGAAGTCG TAGAAAATGA AAGTGGTCGC AAAGACCCAC TCGTTTTTGT

5201  GGAAGGCAAA ATGCCGCAAA AAAGGGAATA AGGGCGACAC GGAATGTTG
      CCTTCCGTTT TACGGCGTTT TTTCCCTTAT TCCCGCTGTG CCTTACAAC

SspI
                                 ------
5251  AATACTCATA CTCTTCCTTT TTCAATATTA TTGAAGCATT TATCAGGGTT
      TTATGAGTAT GAGAAGGAAA AAGTTATAAT AACTTCGTAA ATAGTCCCAA

5301  ATTGTCTCAT GAGCGGATAC ATATTTGAAT GTATTTAGAA AAATAAACAA
      TAACAGAGTA CTCGCCTATG TATAAACTTA CATAAATCTT TTTATTTGTT

5351  ATAGGGGTTC CGCGCACATT TCCCCGAAAA GTGCCACCTG ACGTCTAAGA
      TATCCCCAAG GCGCGTGTAA AGGGGCTTTT CACGGTGGAC TGCAGATTCT

5401  AACCATTATT ATCATGACAT TAACCTATAA AAATAGGCGT ATCACGAGGC
      TTGGTAATAA TAGTACTGTA ATTGGATATT TTTATCCGCA TAGTGCTCCG

5451  CCTTTCGTC
      GGAAAGCAG
```

FIG. 31 pCMV-II - E2661-sAg

SEQ ID NO:6

```
  1  TCGCGCGTTT CGGTGATGAC GGTGAAAAACC TCTGACACAT GCAGCTCCCG GAGACGGTCA CAGCTTGTCT GTAAGCGGAT
     AGCGCGCAAA GCCACTACTG CCACTTTTGG AGACTGTGTA CGTCGAGGGC CTCTGCCAGT GTCGAACAGA CATTCGCCTA

81  GCCGGGAGCA GACAAGCCCG TCAGCGGGTG TTGGCGGGTG TCGGGGGTG CTTAACTATG CGGCATCAGA
     CGGCCCTCGT CTGTTCGGGC AGTCCCGCGC AACCGCCCAC AGCCCCGACC GAATTGATAC GCCGTAGTCT

161  GCAGATTGTA CTGAGAGTGC ACCATATGAA GCTTTTTGCA AAAGCCTAGG CCTCCAAAAA AGCCTCCTCA CTACTTCTGG
     CGTCTAACAT GACTCTCACG TGGTATACTT CGAAAAACGT TTCGGATCC GGAGGTTTT TCGGAGGAGT GATGAAGACC

241  AATAGCTCAG AGGCCGAGGC GGCCTCGGCC TCTGCATAAA TAAAAAAAT TAGTCAGCCA TGGGGCGGAG AATGGGCGGA
     TTATCGAGTC TCCGGCTCCG CCGGAGCCGG AGACGTATTT ATTTTTTTA ATCAGTCGGT ACCCCGCCTC TTACCCGCCT

321  ACTGGGCGGG GAGGGAATTA TTGGCTATTG GCCATTGCAT ACGTTGTATC TATATCATAA TATGTACATT TATATTGGCT
     TGACCCGCCC CTCCCTTAAT AACCGATAAC CGGTAACGTA TGCAACATAG ATATAGTATT ATACATGTAA ATATAACCGA

401  CATGTCCAAT ATGACCGCCA TGTTGACATT GATTATTGAC TAGTTATTAA TAGTAATCAA TTACGGGGTC ATTAGTTCAT
     GTACAGGTTA TACTGGCGGT ACAACTGTAA CTAATAACTG ATCAATAATT ATCATTAGTT AATGCCCCAG TAATCAAGTA

481  AGCCCATATA TGGAGTTCCG CGTTACATAA CTTACGGTAA ATGGCCCGCC TGGCTGACCG CCCAACGACC CCCGCCCATT
     TCGGGTATAT ACCTCAAGGC GCAATGTATT GAATGCCATT TACCGGGCGG ACCGACTGGC GGGTTGCTGG GGGCGGGTAA

561  GACGTCAATA ATGACGTATG TTCCCATAGT AACGCCAATA GGGACTTTCC ATTGACGTCA ATGGGTGGAG TATTTACGGT
     CTGCAGTTAT TACTGCATAC AAGGGTATCA TTGCGGTTAT CCCTGAAAGG TAACTGCAGT TACCCACCTC ATAAATGCCA

641  AAACTGCCCA CTTGGCAGTA CATCAAGTGT ATCATATGCC AAGTCCGCCC CCTATTGACG TCAATGACGG TAAATGGCCC
     TTTGACGGGT GAACCGTCAT GTAGTTCACA TAGTATACGG TTCAGGCGGG GGATAACTGC AGTTACTGCC ATTTACCGGG

721  GCCTGGCATT ATGCCCAGTA CATGACCTTA CGGGACTTTC CTACTTGGCA GTACATCTAC GTATTAGTCA TCGCTATTAC
     CGGACCGTAA TACGGGTCAT GTACTGGAAT GCCCTGAAAG GATGAACCGT CATGTAGATG CATAATCAGT AGCGATAATG
```

FIG. 4B

```
801   CATGGTGATG CGGTTTTGGC AGTACACCAA TGGGCGTGA TAGCGGTTTG ACTCACGGGG ATTTCCAAGT CTCCACCCCA
      GTACCACTAC GCCAAAACCG TCATGTGGTT ACCCGCACCT ATCGCCAAAC TGAGTGCCCC TAAAGGTTCA GAGGTGGGGT

881   TTGACGTCAA TGGGAGTTTG TTTTGGCACC AAAATCAACG GGACTTTCCA AAATGTCGTA ATAACCCCGC CCCGTTGACG
      AACTGCAGTT ACCCTCAAAC AAAACCGTGG TTTTAGTTGC CCTGAAAGGT TTTACAGCAT TATTGGGGCG GGGCAACTGC

961   CAAATGGGCG GTAGGCGTGT ACGGTGGGAG GTCTATATAA GCAGAGCTCG TTTAGTGAAC CGTCAGATCG CCTGGAGACG
      GTTTACCCGC CATCCGCACA TGCCACCCTC CAGATATATT CGTCTCGAGC AAATCACTTG GCAGTCTAGC GGACCTCTGC

1041  CCATCCACGC TGTTTTGACC TCCATAGAAG ACACCGGGAC CGATCCAGCC TCCGGGGCCG GGAACGGTGC ATTGGAACGC
      GGTAGGTGCG ACAAAACTGG AGGTATCTTC TGTGGCCCTG GCTAGGTCGG AGGCGCCGGC CCTTGCCACG TAACCTTGCG

1121  GGATTCCCCG TGCCAAGAGT GACGTAAGTA ACTCTATAGG CCGCCTATAG ACTCTATATA TGGCTCTCTTAT GCATGCTATA
      CCTAAGGGGC ACGTTCTCA CTGCATTCAT GGCGGATATC TGAGATATC GTGGGGAA ACCGAGAATA CGTACGATAT

1201  CTGTTTTTGG CTTGGGGCCT ATACACCCCC GCTCCTTATG CTATAGGTGA TGGTATAGCT TAGCCTATAG GTGTGGGTTA
      GACAAAAACC GAACCCCGGA TATGTGGGGG CGAGGAATAC GATATCCACT ACCATATCGA ATCGGATATC CACACCCAAT

1281  TTGACCATTA CCCTATTGGT TACTCTGTCC GACGATACTT TCAGAGACT GACACGGACT TCCATTACTA GTCCATTTAT CCACAACTAT
      AACTGGTAAT GGGATAACCA ATGAGACAGG CTGCTATGAA AAGTCTCTGA CTGTGCCTGA AGGTAATGAT ACCGAGAAAC GGTGTTGATA

1361  CTCTATTGGC TATATGCCAA TACTCACATA CAACAACGCC GTCCCCGTG CCCGCAGTTT ACAGGATGGG GTCCATTTAT
      GAGATAACCG ATATAACGGTT GTTGTTGCGG CAGGGGGCAC GGGCGTCAAA TGTCCTACCC CAGGTAAATA

1441  TATTTACAAA TTCACATATA CAACAACGCC GTCCCCCGTG CCCGCAGTTT TTATTAAACA TAGCGTGGGA TCTCCGACAT
      ATAAATGTTT AAGTGTATAT GTTGTTGCGG CAGGGGGCAC GGGCGTCAAA AATAATTGT ATCGCACCCT AGAGGCTGTA

1521  CTCGGGTACG TGTTCCGGAC ATGGCCTCTT GGCGGAGCTT CTCCGGTAGC GCCCTGGTCC CCACATCCGA GCCCTGGTCC CATCCGGTCCA
      GAGCCCATGC ACAAGGCCTG TACCCGAGAA GAGGCCATCG CCGCCTCGAA CGGTGTAGGCT GGGACCAGG GTAGGCAGGT
```

FIG. 4C

```
1601  GCGGCTCATG GTCGCTCGGC AGCTCCTTGC TCCTAACAGT GGAGGCCAGA CTTAGGCACA GCACAATGCC CACCACCACC
      CGCCGAGTAC CAGCGAGCCG TCGAGGAACG AGGATTGTCA CCTCCGGTCT GAATCCGTGT CGTGTTACGG GTGGTGGTGG

1681  AGTGTGCCGC ACAAGGCCGT GGCGGTAGGG TATGTGTCTG AAAATGAGCT CGGAGATTGG GCTCGCACCT GGACGCAGAT
      TCACACGGCG TGTTCCGGCA CCGCCATCCC ATACACAGAC TTTTACTCGA GCCTCTAACC CGAGCGTGGA CCTGCGTCTA

1761  GGAAGACTTA AGGCAGCGGC AGAAGAAGAT GCAGGCAGCT GAGTTGTTGT ATTCTGATAA GAGTCAGAGG TAACTCCCGT
      CCTTCTGAAT TCCGTCGCCG TCTTCTTCTA CGTCCGTCGA CTCAACAACA TAAGACTATT CGCAGTCTCC ATTGAGGCA

1841  TGCGGTGTCG TTAACGGTGG AGGGCAGTGT AGTCTGAGCA GTACTCGTTG CTGCCGCGCG CGCCACCAGA CATAATAGCT
      ACGCCACGAC AATTGCCACC TCCCGTCACA TCAGACTCGT CATGAGCAAC GACGGCGCGC GCGGTGTCT GTATTATCGA

─────▷ M  D  A
+3                                         SEQ ID NO:7 ────────────
                                                PstI                    EcoRI

1921  GACAGACTAA CAGACTGTTC CTTTCCATGG GTCTTTTCTG CAGTCACCGT CGTCGACGAA TTCAAGCAAT CATGGATGCA
      CTGTCTGATT GTCTGACAAG GAAAGGTACC CAGAAAAGAC GTCAGTGGCA GCAGCTGCTT AAGTTCGTTA GTACCTACGT

+3     M  K  R  G   L  C  C    V  L  L   L  C  G  A    V  F  V    S  P  S    A  S  E  T   H  V  T
2001  ATGAAGAGAG GGCTCTGCTG CTGTGTGCTG CTGTGTGGAG CAGTCTTCGT TTCGCCCAGC GCTAGCGAAA CCCACGTCAC
      TACTTCTCTC CCGAGACGAC GACACACGAC GACACACCTC GTCAGAAGCA AAGCGGGTCG CGATCGCTTT GGGTGCAGTG

+3     G  G  S    A  G  H    T  V  S  G    F  V  S    L  L  A  P    G  A  K    Q  N  V   Q  L  I
2081  CGGGGGAAGT GCCGGCCACA CTGTGTCTGG ATTTGTTAGC CTCCTCGCAC CAGGCGCCAA GCAGAACGTC CAGCTGATCA
      GCCCCCTTCA CGGCCGGTGT GACACAGACC TAAACAATCG GAGGAGCGTG GTCCGCGGTT CGTCTTGCAG GTCGACTAGT

+3     N  T  N  G    S  W  H    L  N  S  T    A  L  N    C  N  D    S  L  N  T    G  W  L   A  G  L
2161  ACACCAACGG CAGTTGGCAC CTCAATAGCA CGGCCCTGAA CTGCAATGAT AGCCTCAACA CCGGCTGGTT GGCAGGGCTT
      TGTGGTTGCC GTCAACCGTG GAGTTATCGT GCCGGGACTT GACGTTACTA TCGGAGTTGT GGCCGACCAA CCGTCCCGAA

+3     F  Y  H  H   K  F  N    S  S  G    C  P  E  R    L  A  S    C  R  P    L  T  D  F   D  Q  G
2241  TTCTATCACC ACAAGTTCAA CTCTTCAGGC TGTCCTGAGA GGCTAGCCAG CTGCCGACCC CTTACCGATT TTGACCAGGG
      AAGATAGTGG TGTTCAAGTT GAGAAGTCCG ACAGGACTCT CCGATCGGTC GACGGCTGGG GAATGGCTAA AACTGTCCC
```

FIG. 4D

```
+3        W  G  P     I  S  Y  A  N  G  S     G  P  D     Q  R  P  Y     C  W  H     Y  P  P     K  P  C
2321      CTGGGGCCCT ATCAGTTATG CCAACGGAAG CGGCCCCGAC CAGCGCCCCT ACTGCTGGCA CTACCCCCA AAACCTTGCG
          GACCCCGGGA TAGTCAATAC GGTTGCCTTC GCCGGGGCTG GTCGCGGGGA TGACGACCGT GATGGGGGT TTTGGAACGC

+3        G  I  V  P     A  K  S     V  C  G  P     V  Y  C     F  T  P     S  P  V  V     V  G  T     T  D  R
2401      GTATTGTGCC CGCGAAGAGT GTGTGTGGTC CGGTATATTG CTTCACTCCC AGCCCCGTGG TGTGGGAAC GACCGACAGG
          CATAACACGG GCGCTTCTCA CACACACCAG GCCATATAAC GAAGTGAGGG TCGGGGCACC ACACCCTTG CTGGCTGTCC

+3        S  G  A  P     T  Y  S     W  G  E     N  D  T  D     V  F  V     L  N  N     T  R  P  P     L  G  N
2481      TCGGGCGCGC CCACCTACAG CTGGGGTGAA AATGATACGG ACGTCTTCGT CCTTAACAAT ACCAGGCCAC CGCTGGGCAA
          AGCCCGCGCG GGTGGATGTC GACCCCACTT TTACTATGCC TGCAGAAGCA GGAATTGTTA TGGTCCGGTG GCGACCCGTT

+3        W  F  G     C  T  W  M  N  S  T     G  F  T     K  V  C  G     A  P  P     C  V  I     G  G  A
2561      TTGGTTCGGT TGTACCTGGA TGAACTCAAC TGGATTCACC AAAGTGTGCG GAGCGCCTCC TTGTGTCATC GGAGGGGCGG
          AACCAAGCCA ACATGGACCT ACTTGAGTTG ACCTAAGTGG TTTCACACGC CTCGCGGAGG AACACAGTAG CCTCCCCGCC

+3        G  N  N  T     L  H  C     P  T  D  C     F  R  K     H  P  D     A  T  Y  S     R  C  G     S  G  P
2641      GCAACAACAC CCTGCACTGC CCCACTGATT GCTTCCGCAA GCATCCGGAC GCCACATACT CTCGGTGCGG CTCCGGTCCC
          CGTTGTTGTG GGACGTGACG GGGTGACTAA CGAAGGCGTT CGTAGGCCTG CGGTGTATGA GAGCCACGCC GAGGCCAGGG

+3        W  I  T  P     R  C  L     V  D  Y     P  Y  R  L     W  H  Y     P  C  T     I  N  Y  T     I  F  K
2721      TGGATCACAC CCAGGTGCCT GGTCGACTAC CCGTATAGGC TTTGGCATTA TCCTTGTACC ATCAACTACA CCATATTTAA
          ACCTAGTGTG GGTCCACGGA CCAGCTGATG GGCATATCCG AAACCGTAAT AGGAACATGG TAGTTGATGT GGTATAAATT

+3        I  R  M     Y  V  G  G     V  E  H     R  L  E     A  C  N     W  T  R     G  E  R     C  D  L
2801      AATCAGGATG TACGTGGGAG GGGTCGAACA CAGGCTGGAA GCTGCCTGCA ACTGGACGCG GGGCGAACGT TGCGATCTGG
          TTAGTCCTAC ATGCACCCTC CCCAGCTTGT GTCCGACCTT CGACGGACGT TGACCTGCGC CCCGCTTGCA ACGCTAGACC

+3        E  D  R  D     R  S  E     I  D  M  E     N  I  T     S  G  F     L  G  P     L  L  V  L     Q  A  G
2881      AAGATAGGGA CAGGTCCGAG ATCGATATGG AGAACATCAC CTAGGACCCC TGCTCGTGTT ACAGGCGGGG
          TTCTATCCCT GTCCAGGCTC TAGCTATACC TCTTGTAGTG TAGTCCTAAG ACGAGCACAA TGTCCGCCCC
                                          ClaI
                                          ------
```

FIG. 4E

```
+3         F  F  L  L     T  R  I     L  T  I     P  Q  S  L     D  S  W     T  S     L  N  F  L     G  G  S
2961       TTTTCTTGT TGACAAGAAT CCTCACAATA CCGCAGAGTC TAGACTCGTG GTGGACTTCT CTCAATTTTC TAGGGGGATC
           AAAAGAACA ACTGTTCTTA GGAGTGTTAT GGCGTCTCAG ATCTGAGCAC CACCTGAAGA GAGTTAAAAG ATCCCCCTAG

+3            P  V  C     L  G  Q  N     S  Q  S     P  T  S     N  H  S     P  T  S  C     P  P  I     C  P  G
3041       TCCCGTGTGT CTTGGCCAAA ATTCGCAGTC CCCAACCTCC AATCACTCAC CAACCTCCTG TCCTCCAATT TGTCCTGGTT
           AGGGCACACA GAACCGGTTT TAAGCGTCAG GGGTTGGAGG TTAGTGAGTG GTTGGAGGAC AGGAGGTTAA ACAGGACCAA

+3         Y  R  W  M     C  L  R     R  F  I  I     F  L  F     L  C  L  I     F  L  L     V  L  L
3121       ATGCTGGAT GTGTCTGCGG CGTTTTATCA TATTCCTCTT CATCCTGCTG CTATGCCTCA TCTTCTTATT GGTTCTTCTG
           TAGCGACCTA CACAGACGCC GCAAAATAGT ATAAGGAGAA GTAGGACGAC GATACGGAGT AGAAGAATAA CCAAGAAGAC

+3         D  Y  Q  G     L  I  P  G     S  T  T     T  S  T     G  P  C  K     T  C  T
3201       GATTATCAAG GTATGTTGCC CGTTTGTCCT CTAATTCCAG GATCAACAAC AACCAGTACG GGACCATGCA AAACCTGCAC
           CTAATAGTTC CATACAACGG GCAAACAGGA GATTAAGGTC CTAGTTGTTG TTGGTCATGC CCTGGTACGT TTTGGACGTG

+3            T  P  A     Q  G  N  S     M  F  P     S  C  C     C  T  K  P     T  D  G     N  C  T     C  I  P
3281       GACTCCTGCT CAAGGCAACT CTATGTTTCC CTCATGTTGC TGTACAAAAC CTACGGATGG AAATTGCACC TGTATTCCCA
           CTGAGGACGA GTTCCGTTGA GATACAAAGG GAGTACAACG ACATGTTTTG GATGCCTACC TTTAACGTGG ACATAAGGGT

+3         I  P  S  S     W  A  F     A  K  Y  L     W  E  W     A  S  V     R  F  S  W     L  S  L     L  V  P
3361       TCCCATCGTC CTGGGCTTTC GCAAATATCC TATGGGAGTG GGCCTCAGTC CGTTTCTCTT GGCTCAGTTT ACTAGTGCCA
           AGGGTAGCAG GACCCGAAAG CGTTTATATGG ATACCCTCAC CCGGAGTCAG GCAAAGAGAA CCGAGTCAAA TGATCACGGT

+3         F  V  Q  W     F  V  G     L  S  P     T  V  W  L     S  A  I     W  M  M     W  Y  W  G     P  S  L
3441       TTTGTTCAGT GGTTCGTAGG GCTTTCCCCC ACTGTTTGGC TTTCAGCTAT ATGGATGATG TGGTATTGGG GGCCAAGTCT
           AAACAAGTCA CCAAGCATCC CGAAAGGGGG TGACAAACCG AAAGTCGATA TACCTACTAC ACCATAACCC CCGGTTCAGA

+3         Y  S  I     V  S  P     F  F  I  P  L     L  P  I     F  F  C  L     W  V  Y     I  *
                                                                                         EcoRI
3521       GTACAGCATC GTGAGTCCCT TTATACCGCT TTATACCGCT GTTACCAATT TTCTTTTGTC TCTGGGTATA CATTTAAGAA TTCAGACTCG
           CATGTCGTAG CACTCAGGGA AATATGGCGA CAATGGTTAA AAGAAAACAG AGACCCATAT GTAAATTCTT AAGTCTGAGC
```

FIG. 4F

```
                                              BamHI
                                              -----
3601  AGCAAGTCTA GAAAGGCGCG CCAAGATATC AAGGATCCAC TACGCGTTAG AGCTCGCTGA TCAGCCTCGA CTGTGCCTTC
      TCGTTCAGAT CTTTCCGCGC GGTTCTATAG TTCCTAGGTG ATGCGCAATC TCGAGCGACT AGTCGGAGCT GACACGGAAG

3681  TAGTTGCCAG CCATCTGTTG TTTGCCCCTC CCCCGTGCCT TCCTTGACCC TGGAAGTGC CACTCCCACT GTCCTTTCCT
      ATCAACGGTC GGTAGACAAC AAACGGGGAG GGGGCACGGA AGGAACTGGG ACCTTCCACG GTGAGGTGA CAGGAAAGGA

3761  AATAAAATGA GGAAATTGCA TCGCATTGTC TGAGTAGGTG TCATTCTATT CTGGGGGGTG GGGTGGGGCA GGACAGCAAG
      TTATTTTACT CCTTTAACGT AGCGTAACAG ACTCATCCAC AGTAAGATAA GACCCCCCAC CCCACCCCGT CCTGTCGTTC

3841  GGGGAGGATT GGGAAGACAA TAGCAGGCAT GCTGGGGAGC TCTTCCGCTT CCTCGCTCAC TGACTCGCTG CGCTCGGTCG
      CCCCTCCTAA CCCTTCTGTT ATCGTCCGTA CGACCCCTCG CGAAGGCGAA GGAGCGAGTG ACTGAGCGAC GCGAGCCAGC

3921  TTCGGCTGCG GCGAGCGGTA TCAGCTCACT CAAAGGCGGT AATACGGTTA TCCACAGAAT CAGGGGATAA CGCAGGAAAG
      AAGCCGACGC CGCTCGCCAT AGTCGAGTGA GTTTCCGCCA TTATGCCAAT AGGTGTCTTA GTCCCCTATT GCGTCCTTTC

4001  AACATGTGAG CAAAAGGCCA GCAAAAGGCC AGGAACCGTA AAAAGGCCGC GTTGCTGGCG TTTTTCCATA GGCTCCGCCC
      TTGTACACTC GTTTTCCGGT CGTTTTCCGG TCCTTGGCAT TTTTCCGGCG CAACGACCGC AAAAAGGTAT CCGAGGCGGG

4081  CCCTGACGAG CATCACAAAA ATCGACGCTC AAGTCAGAGG TGGCGAAACC CGACAGGACT ATAAAGATAC CAGGCGTTTC
      GGGACTGCTC GTAGTGTTTT TAGCTGCGAG TTCAGTCTCC ACCGCTTTGG GCTGTCCTGA TATTTCTATG GTCCGCAAAG

4161  CCCCTGGAAG CTCCCTCGTG CGCTCTCCTG TTCCGACCCT GCCGCTTACC GGATACCTGT CCGCCTTTCT CCCTTCGGGA
      GGGGACCTTC GAGGGAGCAC GCGAGAGGAC AAGGCTGGGA CGGCGAATGG CCTATGGACA GGCGGAAAGA GGGAAGCCCT

4241  AGCGTGGCGC TTTCTCAATG CTCACGCTGT AGGTATCTCA GTTCGGTGTA GGTCGTTCGC TCCAAGCTGG GCTGTGTGCA
      TCGCACCGCG AAAGAGTTAC GAGTGCGACA TCCATAGAGT CAAGCCACAT CCAGCAAGCG AGGTTCGACC CGACACACGT

4321  CGAACCCCCC GTTCAGCCCG ACCGCTGCGC CTTATCCGGT AACTATCGTC TTGAGTCCAA CCCGGTAAGA CACGACTTAT
      GCTTGGGGGG CAAGTCGGGC TGGCGACGCG GAATAGGCCA TTGATAGCAG AACTCAGGTT GGGCCATTCT GTGCTGAATA

4401  CGCCACTGGC AGCAGCCACT GGTAACAGGA TTAGCAGAGC GAGGTATGTA GGCGGTGCTA CAGAGTTCTT GAAGTGGTGG
      GCGGTGACCG TCGTCGGTGA CCATTGTCCT AATCGTCTCG CTCCATACAT CCGCCACGAT GTCTCAAGAA CTTCACCACC

FIG. 4G
```

```
4481  CCTAACTACG GCTACACTAG AAGGACAGTA TTTGGTATCT GCGCTCTGCT GAAGCCAGTT ACCTTCGGAA AAAGAGTTGG
      GGATTGATGC CGATGTGATC TTCCTGTCAT AAACCATAGA CGCGAGACGA CTTCGGTCAA TGGAAGCCTT TTTCTCAACC

4561  TAGCTCTTGA TCCGGCAAAC AAACCACCGC TGGTAGCGGT TTTGCAAGCA TTTGCAAGCA GCAGATTACG CGCAGAAAAA
      ATCGAGAACT AGGCCGTTTG TTTGGTGGCG ACCATCGCCA AAACGTTCGT AAACGTTCGT CGTCTAATGC GCGTCTTTTT

4641  AAGGATCTCA AGAAGATCCT TTGATCTTTT CTACGGGGTC TGACGCTCAG TGGAACGAAA ACTCACGTTA AGGGATTTTG
      TTCCTAGAGT TCTTCTAGGA AACTAGAAAA GATGCCCCAG ACTGCGAGTC ACCTTGCTTT TGAGTGCAAT TCCCTAAAAC

4721  GTCATGAGAT TATCAAAAAG GATCTTCACC TAGATCCTTT TAAATTAAAA ATGAAGTTTT AAATCAATCT AAAGTATATA
      CAGTACTCTA ATAGTTTTTC CTAGAAGTGG ATCTAGGAAA ATTTAATTTT TACTTCAAAA TTTAGTTAGA TTTCATATAT

4801  TGAGTAAACT TGGTCTGACA GTTACCAATG CTTAAATCAGT GAGGCACCTA TCTCAGCGAT CTGTCTATTT CGTTCATCCA
      ACTCATTTGA ACCAGACTGT CAATGGTTAC GAATTAGTCA CTCCGTGGAT AGAGTCGCTA GACAGATAAA GCAAGTAGGT

4881  TAGTTGCCTG ACTCCCCGTC GTGTAGATAA CTACGATACG GGAGGGCTTA CCATCTGGCC CCAGTGCTGC AATGATACCG
      ATCAACGGAC TGAGGGGCAG CACATCTATT GATGCTATGC CCTCCCGAAT GGTAGACCGG GGTCACGACG TTACTATGGC

4961  CGAGACCCAC GCTCACCGGC TCCAGATTTA TCAGCAATAA TTGTTGCCGG ACCAGCCAGC CGGAAGGGCC GTGGTCCTGC
      GCTCTGGGTG CGAGTGGCCG AGGTCTAAAT AGTCGTTATT AACAACGGCC TGGTCGGTCG GCCTTCCCGG CACCAGGACG

5041  AACTTTATCC GCCTCCATCC AGTCTATTAA TTGTTGTTGC TGACTGGTTT ATGGCTTCAT GCCAGTTAAT AGTTTGCGCA
      TTGAAATAGG CGGAGGTAGG TCAGATAATT AACAACAACG ACTGACCAAA TACCGAAGTA CGGTCAATTA TCAAACGCGT

5121  ACGTTGTTGC CATTGCTACA GGCATCGTGG TGTCACGCTC GTCGTTTGGT ATGGCTTCAT CCGATCGTTG TTCCCAACGA
      TGCAACAACG GTAACGATGT CCGTAGCACC CAGTGCGAGC CAGCAAACCA TACCGAAGTA GGCTAGCAAC AAGGGTTGCT

5201  TCAAGGCGAG TTACATGATC CCCATGTTG TGCAAAAAAG CGGTTAGCTC CTTCGGTCCT CCGATCGTTG TCAGAAGTAA
      AGTTCCGCTC AATGTACTAG GGGGTACAAC ACGTTTTTTC GCCAATCGAG GAAGCCAGGA GGCTAGCAAC AGTCTTCATT

5281  GTTGGCCGCA GTGTTATCAC TCATGGTTAT GGCAGCACTG CATAATTCTC TTACTGTCAT GCCATCCGTA AGATGCTTTT
      CAACCGGCGT CACAATAGTG AGTACCAATA CCGTCGTGAC GTATTAAGAG AATGACAGTA CGGTAGGCAT TCTACGAAAA
```

FIG. 4H

```
5361  CTGTGACTGG TGAGTACTCA ACCAAGTCAT TCTGAGAATA GTGTATGCGG CGACCGAGTT GCTCTTGCCC GGCGTCAATA
      GACACTGACC ACTCATGAGT TGGTTCAGTA AGACTCTTAT CACATACGCC GCTGGCTCAA CGAGAACGGG CCGCAGTTAT

5441  CGGGATAATA CCGCGCCACA TAGCAGAACT TTAAAAGTGC TCATCATTGG AAAACGTTCT TCGGGGCGAA AACTCTCAAG
      GCCCTATTAT GGCGCGGGTG ATCGTCTTGA AATTTTCACG AGTAGTAACC TTTTGCAAGA AGCCCCGCTT TTGAGAGTTC

5521  GATCTTACCG CTGTTGAGAT CCAGTTCGAT GTAACCCACT CGTGCACCCA ACTGATCTTC AGCATCTTTT ACTTTCACCA
      CTAGAATGGC GACAACTCTA GGTCAAGCTA CATTGGGTGA GCACGTGGGT TGACTAGAAG TCGTAGAAAA TGAAAGTGGT

5601  GCGTTTCTGG GTGAGCAAAA ACAGGAAGGC AAAATGCCGC AAAAAAGGGA ATAAGGGCGA CACGGAAATG TTGAATACTC
      CGCAAAGACC CACTCGTTTT TGTCCTTCCG TTTTACGGCG TTTTTTCCCT TATTCCCGCT GTGCCTTTAC AACTTATGAG

5681  ATACTCTTCC TTTTTCAATA TTATTGAAGC ATTTATCAGG GTTATTGTCT CATGAGCGGA TACATATTTG AATGTATTTA
      TATGAGAAGG AAAAAGTTAT AATAACTTCG TAAATAGTCC CAATAACAGA GTACTCGCCT ATGTATAAAC TTACATAAAT

5761  GAAAAATAAA CAAATAGGGG TTCCGCGCAC ATTTCCCCGA AAAGTGCCAC CTGACGTCTA AGAAACCATT ATTATCATGA
      CTTTTATTT GTTTATCCCC AAGGCGCGTG TAAAGGGGCT GACTGCAGAT TCTTTGGTAA TAATAGTACT

5841  CATTAACCTA TAAAAATAGG CGTATCACGA GGCCCTTTCG TC
      GTAATTGGAT ATTTTTATCC GCATAGTGCT CCGGGAAAGC AG
```

FIG. 41

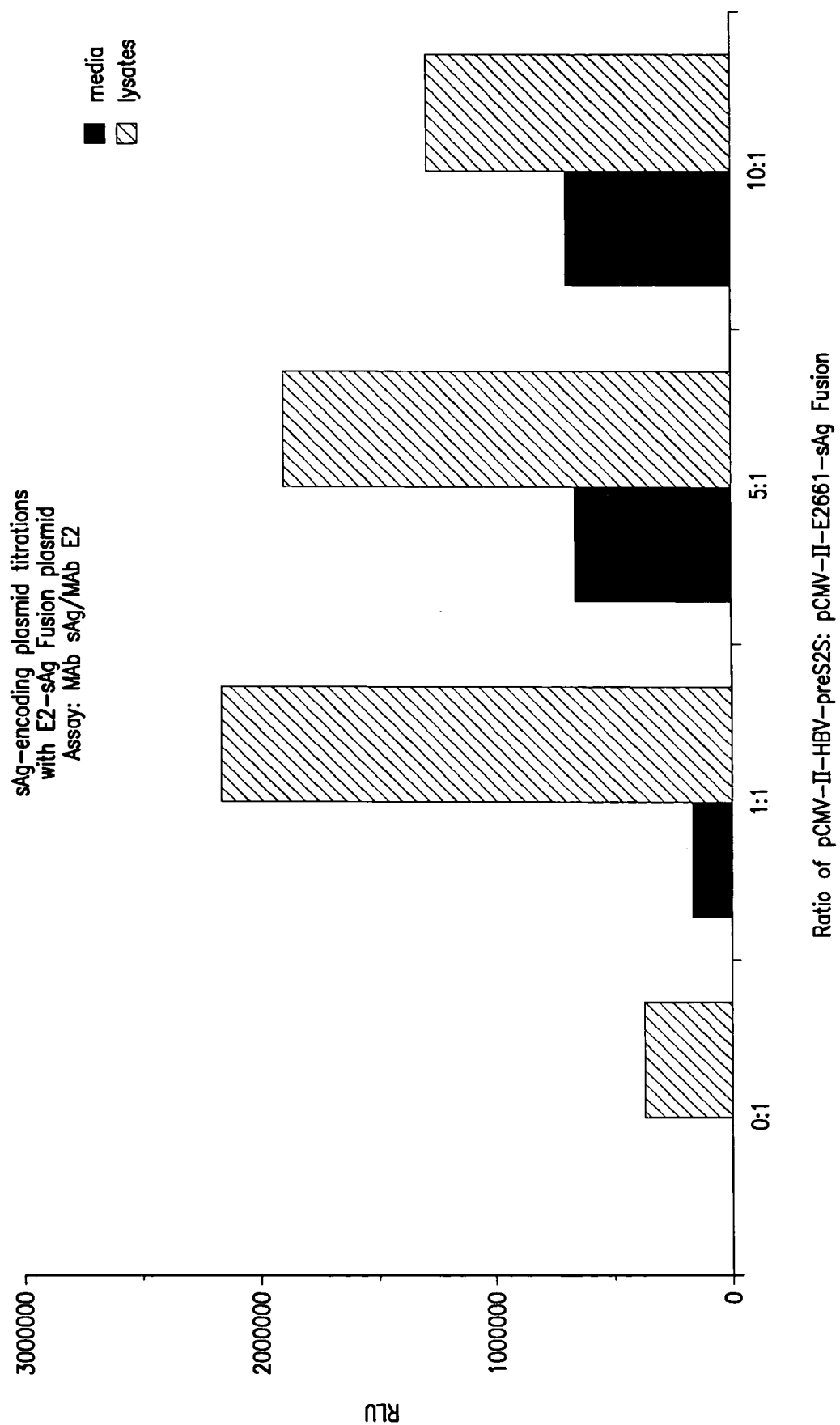

Sucrose Gradient Sedimentation of Media from COS7 Cells Transiently Transfected with Different Ratios of sAg:E2 Fusion Assay: MAb sAg/ MAb sAg

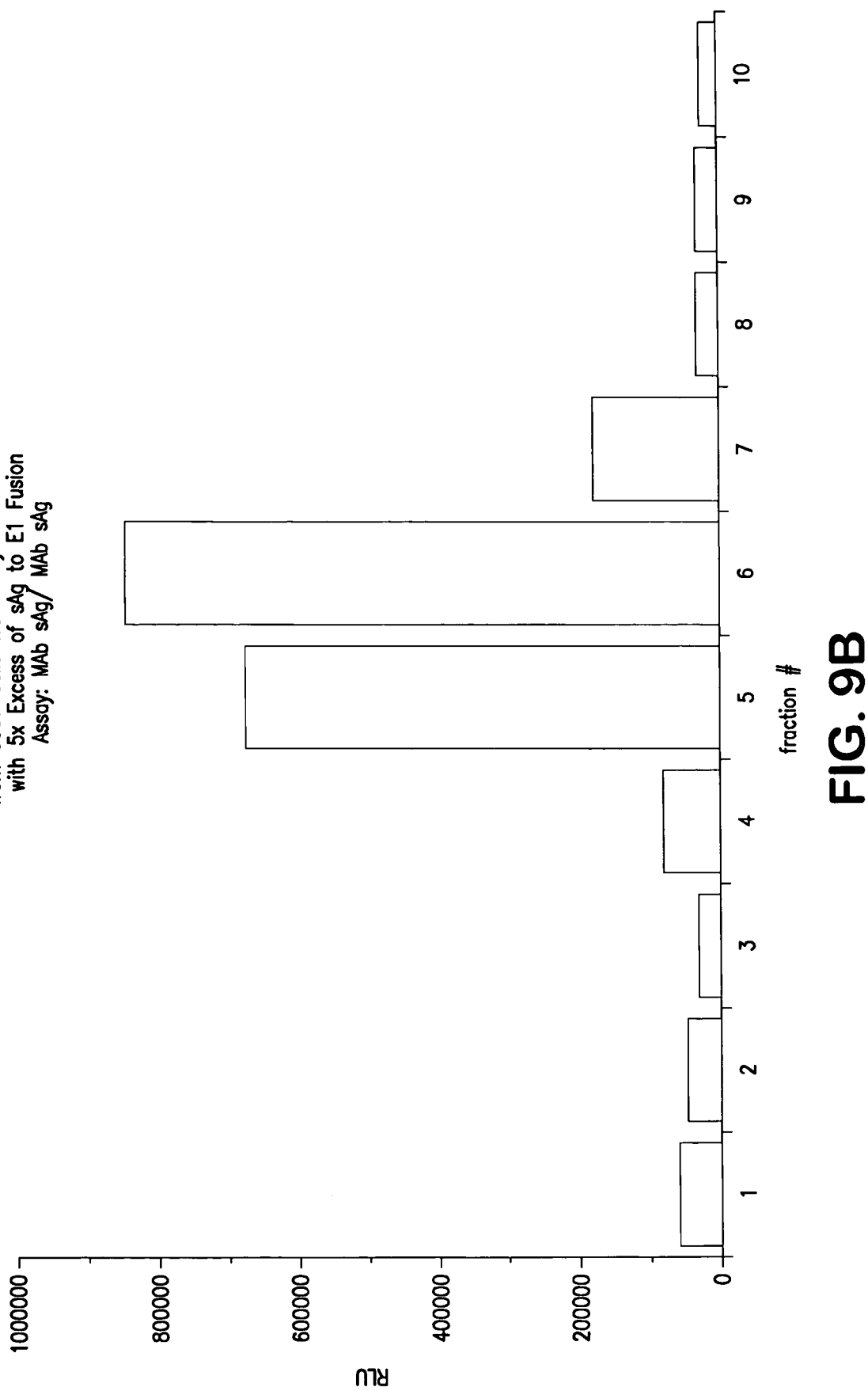

HBV/HCV VIRUS-LIKE PARTICLE

CROSS-REFERENCE TO RELATED APPLICATION

This application is a divisional of U.S. patent application Ser. No. 09/721,480, filed Nov. 22, 2000 now U.S. Pat. No. 6,740,323, from which application priority is claimed pursuant to 35 U.S.C. §120, and this application is related to Provisional Patent Application Ser. No. 60/167,224, filed Nov. 24, 1999, from which priority is claimed under 35 USC §119 (e)(1), and which applications are incorporated herein by reference in their entireties.

TECHNICAL FIELD OF THE INVENTION

The invention is related to the area of recombinant vaccines. It is particularly related to the field of chimeric antigens and virus-like particles for use in vaccines, especially combination vaccines for Hepatitis B virus (HBV) and Hepatitis C virus (HCV).

BACKGROUND OF THE INVENTION

Hepatitis C virus (HCV) infects approximately 1% of the world's population and causes serious health problems. Over 75% of acutely infected individuals eventually progress to a chronic carrier state that can result in cirrhosis, liver failure, and hepatocellular carcinoma. A very small fraction of chronically infected patients clear HCV naturally and resolve chronic hepatitis. See Alter et al. (1992) N. Engl. J. Med. 327:1899-1905; Resnick and Koff. (1993) Arch. Intern. Med. 153:1672-1677; Seeff (1995) Gastrointest. Dis. 6:20-27; Tong et al. (1995) N. Engl. J. Med. 332:1463-1466. Immunization against E2 glycoproteins of some flaviviruses (see e.g., Konishi et al., (1992) Virology 188: 714-720), including HCV (Ishii et al., (1998) Hepatology 28: 1117-1120), may protect against infection. However, attempts to express recombinant HCV E1 and E2 glycoproteins have been frustrated by the fact that these proteins are not secreted from the host cell but are retained within the endoplasmic reticulum (Dubuisson et al. (1994) J. Virology 68: 6147-6160).

One approach to making vaccines for HCV and other viruses which has been attempted is to prepare chimeric antigens consisting of fusions of hepatitis B virus surface antigen (HBsAg) with a heterologous antigen, for example a portion of an HCV protein. See, e.g., Inchauspe et al. (1998) Dev. Biol. Stand. 92: 162-168; Nakano et al. (1997) J. Virol. (1997) 71: 7101-7109; and Inchauspe et al. (1997) Vaccine 15: 853-856. The use of HBsAg is attractive for the production of immunogenic compositions such as vaccines because HBsAg is highly immunogenic and is secreted from cultured cells in the form of virus-like particles (U.S. Pat. No. 5,098,704). Attempts to introduce small portions of viral proteins into HBsAg have succeeded in the production of virus-like particles (see e.g., Delpeyroux et al. (1990) J. Virology 64: 6090-6100, who inserted an 11 amino acid segment of polio virus capsid protein into HBsAg). However, in one study only two out of six fusion proteins containing HBsAg combined with different hydrophillic domains of HCV E2 were secreted into the culture medium as virus-like particles (Lee et al. (1996) J. Med. Virol. 50: 145-151), possibly because the E2 inserts were too large or hydrophilic. The insertion site of heterologous epitopes into HBsAg may be an important factor. A study which inserted an epitope of HBV nucleocapsid (HBcAg) at various positions into HBsAg found that insertion into an internal site in HBsAg resulted in a chimeric protein that was immunogenic for HBcAg, while insertion at the C-terminus was weakly immunogenic (Schodel et al. (1992) J. Virology 66: 106-114). Insertion at the N-terminus prevented surface access of the HBcAg epitope in the resultant particles and was non-immunogenic (Id.). Apparently, the molecular context in which an epitope is presented is important in determining immunogenicity, probably because of subtle alterations of protein secondary and tertiary structure. This principle was further illustrated by Eckhart et al. ((1996) J. Gen. Virol. 77: 2001-2008), who introduced a conserved, six amino acid epitope of HIV-1 gp41 protein into influenza hemagglutinin and obtained neutralizing antibodies, but could not generate neutralizing antibodies when the same epitope was inserted into HBsAg. Smaller isolated epitopes are more likely to be sensitive to such effects than larger portions of an immunogenic protein.

Currently there is no method available for expressing entire E1 or E2 glycoproteins of HCV in virus-like particles for use in immunization. Available methods limit chimeric proteins based on HBsAg to the insertion of only small isolated domains of E2, which may or may not have a native immunogenic structure. Thus, there remains a need in the art for methods and materials that can be used to express HCV antigens in an immunogenic form in virus-like particles.

SUMMARY OF THE INVENTION

It is an object of the invention to provide HBV/HCV chimeric antigens for use in immunogenic compositions. It is a further object of the invention to provide virus-like particles comprising HBV/HCV chimeric antigens and methods and materials for producing such virus-like particles. It is another object of the invention to provide HBV/HCV combination vaccines. These and other objects of the invention are provided by one or more of the embodiments described below.

One embodiment of the invention provides a virus-like particle for use as an immunogen or as a component of a vaccine. The virus-like particle comprises a first HBsAg (hepatitis B virus surface antigen) and a chimeric antigen. The chimeric antigen comprises a second HBsAg which is linked to an HCV immunogenic polypeptide. The first and the second HBsAg each comprise a substantially complete S domain.

Another embodiment of the invention provides another virus-like particle for use as an immunogen or as a component of a vaccine. The virus-like particle comprises a first HBsAg and first and second chimeric antigens. The first chimeric antigen comprises a second HBsAg which is linked to a first immunogenic polypeptide comprising an HCV E1 glycoprotein or a fragment thereof. The second chimeric antigen comprises a third HBsAg which is linked to a second immunogenic polypeptide comprising an HCV E2 glycoprotein or a fragment thereof. The first, second, and third HBsAg each comprise a substantially complete S domain.

Still another embodiment of the invention provides fusion proteins comprising a substantially complete S domain of HBsAg and a polypeptide. In one fusion protein, the polypeptide comprises (a) amino acid residues 192 to 330 of an HCV-1 polyprotein, or (b) the corresponding residues of other HCV isolates, or (c) an immunogenic sequence having at least about 80% sequence identity to (a) or (b). In another fusion protein, the polypeptide comprises (a) amino acid residues 384 to 661 of an HCV-1 polyprotein, or (b) the corresponding residues of other HCV isolates, or (c) an immunogenic sequence having at least about 80% sequence identity to (a) or (b).

Yet another embodiment of the invention provides nucleic acid molecules which encode fusion proteins comprising a substantially complete S domain of HBsAg and a polypeptide. In one fusion protein, the polypeptide comprises (a) amino acid residues 192 to 330 of an HCV-1 polyprotein, or (b) the corresponding residues of other HCV isolates, or (c) an immunogenic sequence having at least about 80% sequence identity to (a) or (b). In another fusion protein, the polypeptide comprises (a) amino acid residues 384 to 661 of an HCV-1 polyprotein, or (b) the corresponding residues of other HCV isolates, or (c) an immunogenic sequence having at least about 80% sequence identity to (a) or (b). These nucleic acid molecules are employed as components of immunogenic compositions, which are additional embodiments.

Another embodiment of the invention provides vectors comprising nucleic acid molecules which encode fusion proteins. The fusion proteins comprise a substantially complete S domain of HBsAg and a polypeptide comprising an immunogenic fragment of an HCV-1 polyprotein.

A further embodiment of the invention provides a method of producing virus-like particles. A cell is cultured in a culture medium, whereby the cell expresses virus-like particles comprising a first HBsAg and a chimeric antigen. The chimeric antigen comprises a second HBsAg which is linked to an HCV immunogenic polypeptide. The first and the second HBsAg each comprise a substantially complete S domain. The virus-like particles are then isolated from the culture medium.

Yet another embodiment is a method of producing a cell line that expresses virus-like particles. A cell is transfected with a vector that expresses virus-like particles comprising a first HBsAg and a chimeric antigen. The chimeric antigen comprises a second HBsAg which is linked to an HCV immunogenic polypeptide. The first and the second HBsAg each comprise a substantially complete S domain. The cell is cultured to produce a cell line that expresses the virus-like particles.

Still other embodiments of the invention are cell lines that express virus-like particles. In one cell line, the virus-like particles comprise a first HBsAg and a chimeric antigen. The chimeric antigen comprises a second HBsAg which is linked to an HCV immunogenic polypeptide. The first and the second HBsAg each comprise a substantially complete S domain. In another type of cell line, the virus-like particles comprise a first HBsAg and first and second chimeric antigens. The first chimeric antigen comprises a second HBsAg which is linked to a first immunogenic polypeptide comprising an HCV E1 glycoprotein or a fragment thereof, and the second chimeric antigen comprises a third HBsAg which is linked to a second immunogenic polypeptide comprising an HCV E2 glycoprotein or a fragment thereof. The first, second, and third HBsAg each comprise a substantially complete S domain.

The invention thus provides the art with novel methods and materials for the production of HBV/HCV combination vaccines.

BRIEF DESCRIPTION OF THE DRAWINGS

FIGS. 1A and 1B-1F show the expression vector pCMVII (FIG. 1A) and its nucleotide sequence (FIGS. 1B-1F; SEQ ID NO:1).

FIGS. 2A and 2B-2I show the expression vector pCMVII-pS2-sAg (FIG. 2A) and its nucleotide sequence (FIGS. 2B-2I and SEQ ID NO:2; preS2 coding sequence begins at nucleotide position 1988 and ends at nucleotide base 2152, and SAg coding sequence begins at base 2153 and ends at 2830). The amino acid sequence of the encoded preS2-S polypeptide is also displayed in FIGS. 2B-2I and in SEQ ID NO:3.

FIGS. 3A and 3B-3I show the expression vector pCMVII opti 330 E1/SAg (FIG. 3A) and its nucleotide sequence (FIGS. 3B-3I and SEQ ID NO:4; 330 E1 coding sequence begins at nucleotide position 1992 and ends at nucleotide base 2483 and SAg coding sequence begins at base 2484). The amino acid sequence of the encoded chimeric antigen polypeptide is also displayed in FIGS. 3B-3I and in SEQ ID NO:5.

FIGS. 4A and 4B-4I show the expression vector pCMV-II-E2661-sAg (FIG. 4A) and its nucleotide sequence (FIGS. 4B-4F and SEQ ID NO:6; the human tissue plasminogen activator leader sequence begins at nucleotide position 1992 and ends at nucleotide position 2060, the 661 E2 coding sequence begins at nucleotide position 2067 and ends at nucleotide base 2900, and the sAg coding sequence begins at base 2907). The amino acid sequence of the encoded chimeric antigen polypeptide is also displayed in FIGS. 4B-4F and in SEQ ID NO:7.

FIGS. 6A and 6B illustrate the expression of HCVE2-HBsAg fusion protein in COS7 cells. Increasing amounts of sAg-encoding plasmid were expressed together with HCVE2-sAg fusion plasmid. The experiment is described in Example 2. The capture antibody was MAb sAg, and the detecting antibody was MAb E2 (FIG. 6A) or MAb sAg (FIG. 6B).

FIGS. 7A and 7B show the sedimentation profile of virus-like particles expressed from COS7 cells transiently transfected with different ratios of sAg:E2-sAg fusion protein. The experiment is described in Example 2. The capture antibody was MAb sAg, and the detecting antibody was MAb E2 (FIG. 7A) or MAb sAg (FIG. 7B).

FIGS. 9A and 9B show the sedimentation profile of virus-like particles expressed from COS7 cells transiently transfected with a 5:1 ratio of sAg:E1-sAg fusion protein. The experiment is described in Example 3. The capture antibody was MAb sAg, and the detecting antibody was MAb E1 (FIG. 9A) or MAb sAg (FIG. 9B).

In FIG. 10A, detecting antibodies for E1 and E2 were employed, demonstrating the secretion into the media of both E1- and E2-derived polypeptides. In FIG. 10B, the detecting antibody was MAb sAg.

DETAILED DESCRIPTION OF THE INVENTION

Figure 1A:
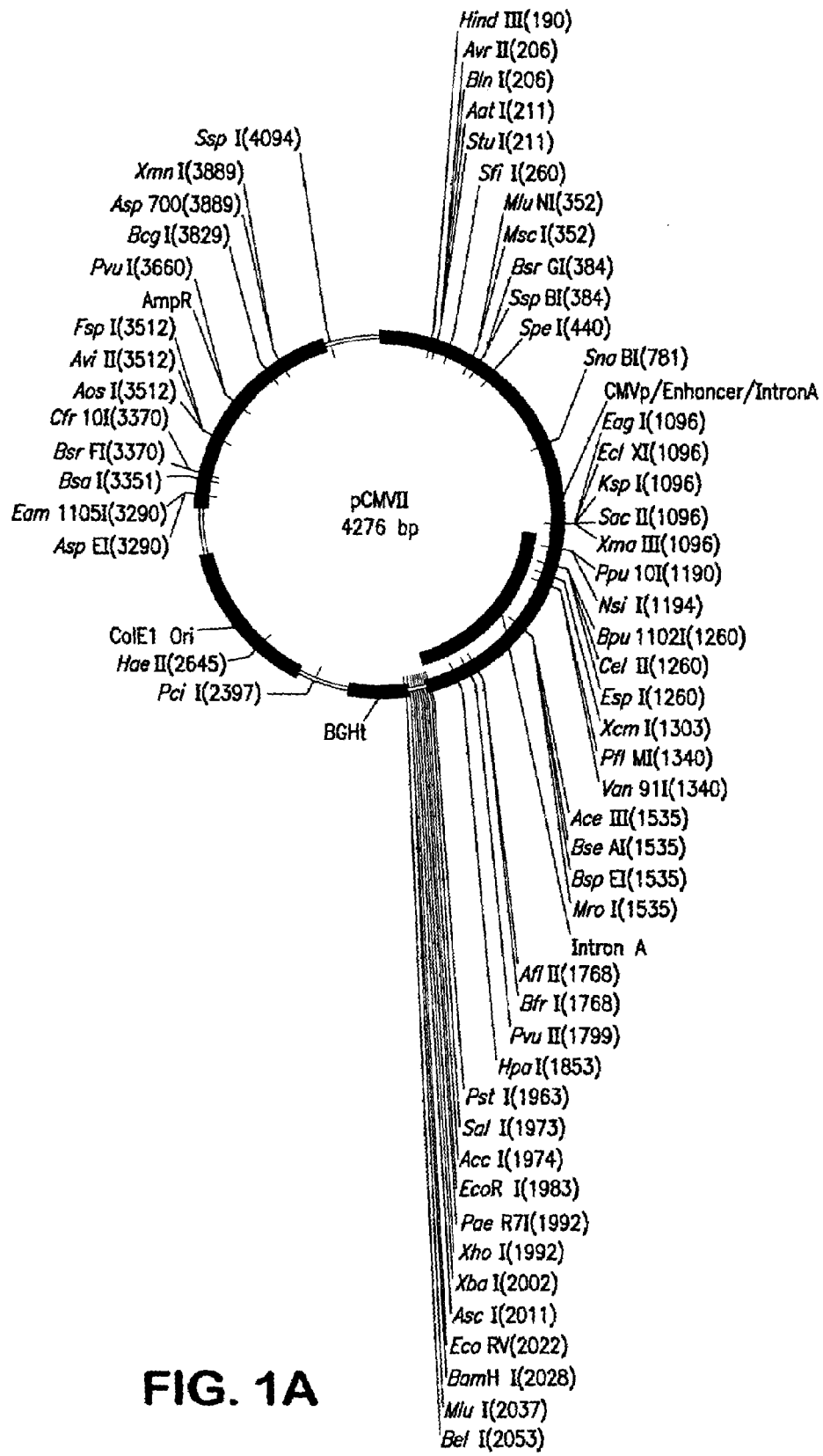
Figure 2A:
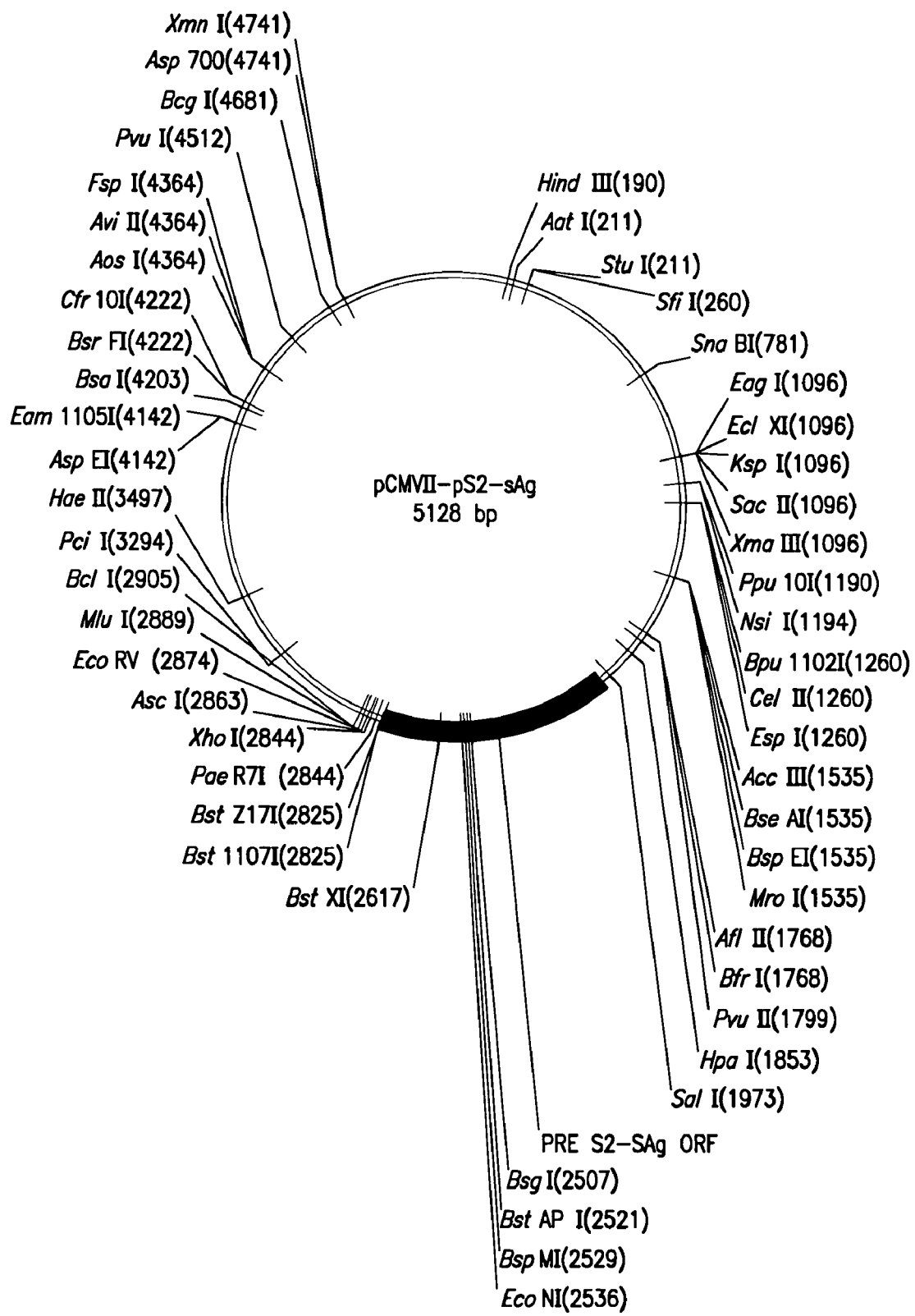
Figure 3A:
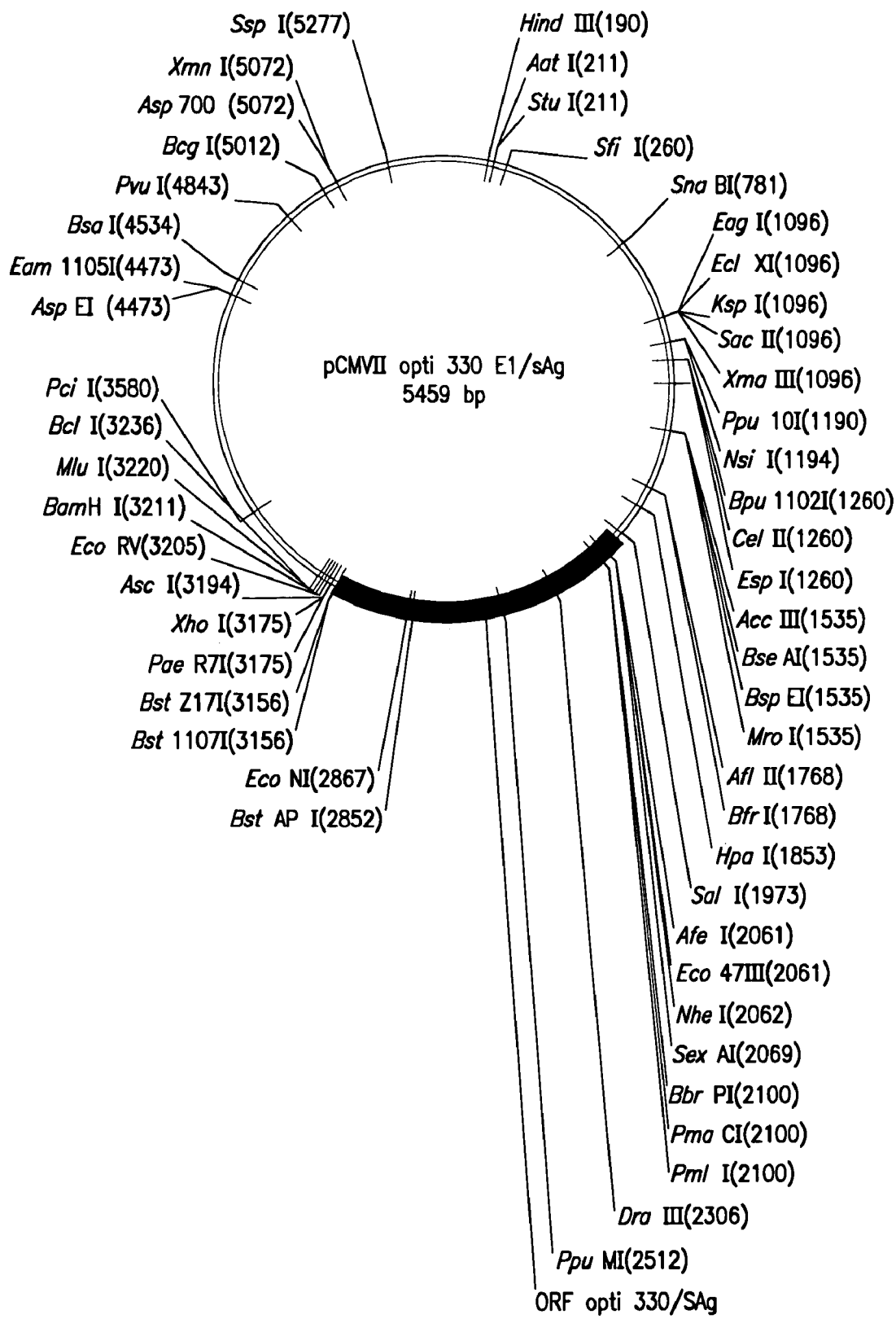
Figure 4A:
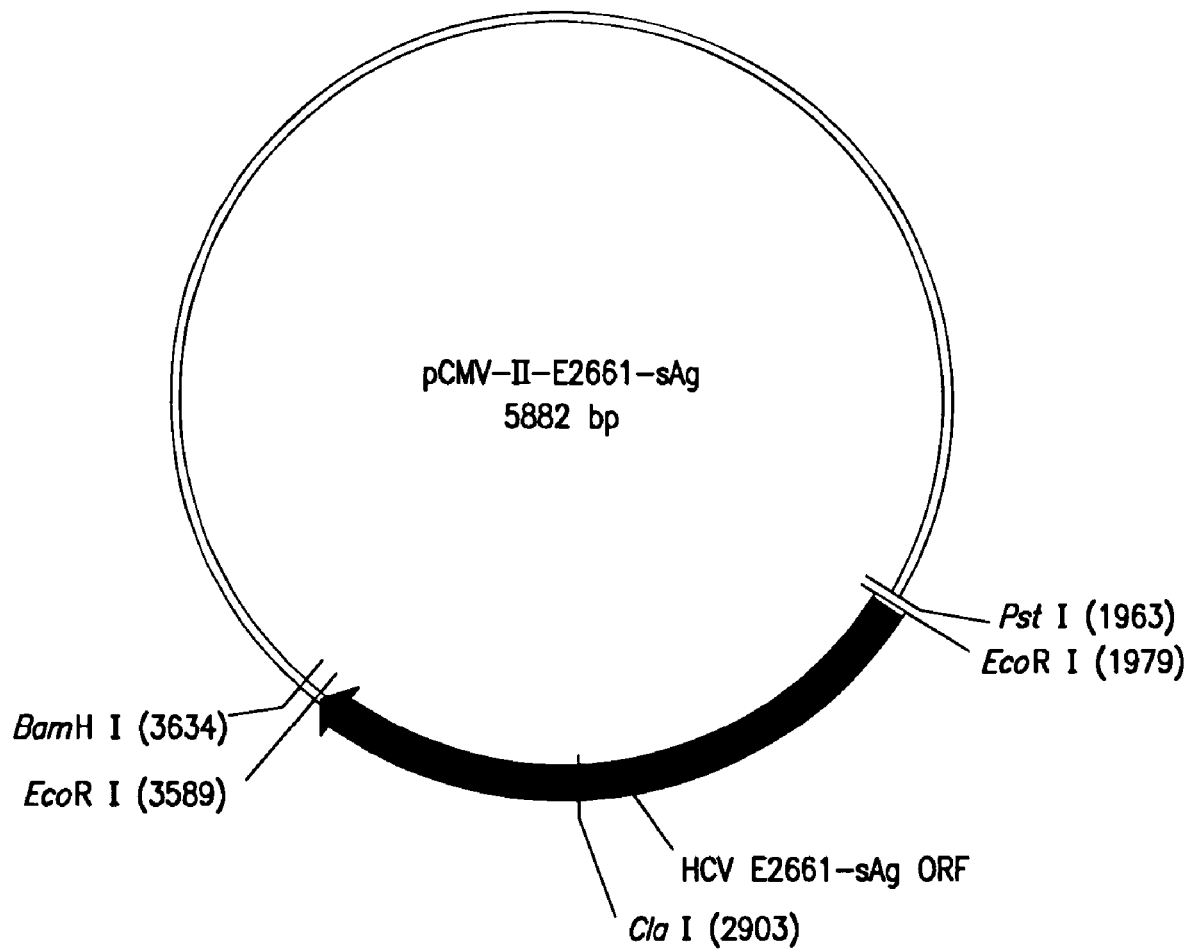

A summary of standard techniques and procedures which may be employed in order to perform the invention follows. This summary is not a limitation on the invention but, rather, gives examples which may be used, but which are not required.

The practice of the present invention will employ, unless otherwise indicated, conventional techniques of molecular biology, microbiology, recombinant DNA, and immunology, which are within the skill of the art. Such techniques are explained fully in the literature e.g., Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Animal Cell Culture* (R. I. Freshney ed. 1986); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London).

All publications, patents and patent applications cited herein, whether supra or infra, are hereby incorporated by reference in their entireties.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

Standard abbreviations for nucleotides and amino acids are used in this specification. For example, the following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "polypeptide" and "protein" are used interchangeably herein and refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. HCV encodes a single polyprotein having more than 3000 amino acid residues (Choo et al. *Science* (1989) 244:359-362; Choo et al. *Proc. Natl. Acad. Sci. USA* (1991) 88:2451-2455; Han et al. *Proc. Natl. Acad. Sci. USA* (1991) 88:1711-1715). The polyprotein is processed co- and post-translationally into both structural and non-structural (NS) proteins.

In particular, several proteins are encoded by the HCV genome. The order and nomenclature of the cleavage products of the HCV polyprotein is as follows: $NH_2$—C-E1-E2-NS2-NS3-NS4a-NS4b-NS5a-NS5b-COOH. Initial cleavage of the polyprotein is catalyzed by host proteases which liberate three structural proteins, the N-terminal nucleocapsid protein (termed "Core") and two envelope glycoproteins, "E1" (also known as E) and "E2" (also known as E2/NS1), as well as nonstructural (NS) proteins that contain the viral enzymes. The NS regions are termed NS2, NS3, NS4 and NS5. NS2 is an integral membrane protein with proteolytic activity. NS2, either alone or in combination with NS3, cleaves the NS2-NS3 sissle bond which in turn generates the NS3 N-terminus and releases a large polyprotein that includes both serine protease and RNA helicase activities. The NS3 protease serves to process the remaining polyprotein. Completion of polyprotein maturation is initiated by autocatalytic cleavage at the NS3-NS4a junction, catalyzed by the NS3 serine protease. Subsequent NS3-mediated cleavages of the HCV polyprotein appear to involve recognition of polyprotein cleavage junctions by an NS3 molecule of another polypeptide. In these reactions, NS3 liberates an NS3 cofactor (NS4a), two proteins with unknown function (NS4b and NS5a), and an RNA-dependent RNA polymerase (NS5b). Any one of these proteins, as well as immunogenic fragments thereof, will find use with the subject chimeric antigens.

The polypeptide for use in the chimeric antigens need not be physically derived from HCV, but may be synthetically or recombinantly produced. Moreover, the polypeptide may be derived from any of the various HCV strains, such as from strains 1, 2, 3 or 4 of HCV (described further below). A number of conserved and variable regions are known between these strains and, in general, the amino acid sequences of epitopes derived from these regions will have a high degree of sequence homology, e.g., amino acid sequence homology of more than 30%, preferably more than 40%, preferably more than 50%, preferably more than about 75%, more preferably more than about 80%-85%, preferably more than about 90%, and most preferably at least about 95%-98% sequence identity, or more, when the two sequences are aligned. Thus, for example, the term "E2" polypeptide refers to the native E2 protein from any of the various HCV strains, as well as E2 analogs, muteins and immunogenic fragments, as defined further below.

The terms "analog" and "mutein" refer to biologically active derivatives of the reference molecule, or fragments of such derivatives, that retain desired activity, such as immunological activity as described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publ. No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains the ability to elicit an immune response as defined below. For example, preferred immunogenic fragments, include but are not limited to fragments of HCV Core that comprise, e.g., amino acids 10-45, 10-53, 67-88, 81-130, 86-100, 120-130, 121-135 and 121-170 of the polyprotein, numbered relative to the HCV-1a sequence presented in Choo et al. (1991) *Proc Natl Acad Sci USA* 88:2451, as well as defined epitopes derived from the c33c region of the HCV polyprotein, as well as any of the other various epitopes identified from the HCV core, E1, E2, NS3 and NS4 regions. See, e.g., Chien et al. *Proc. Natl. Acad. Sci. USA* (1992) 89:10011-10015; Chien et al. *J. Gastroent. Hepatol.* (1993) 8:S33-39; Chien et al. International Publ. No. WO 93/00365; Chien, D. Y. International Publ. No. WO 94/01778; and U.S. Pat. No. 6,150,087, incorporated herein by reference in its entirety. Representative fragments of E1 and E2 polypeptides include C-terminally truncated variants of these molecules, such as E1 polypeptides terminating at, e.g., amino acids 369 and lower, such as e.g., E1 polypeptides ending in amino acids 351, 352, 353 and so on, and E2 polypeptides, terminating at about amino acids 730, such as E2 polypeptides ending in for example amino acids 716, 717, 718 and so on. These molecules are described in, e.g., U.S. Pat. No. 6,121,020, incorporated herein by reference in its entirety.

"Antigenic determinant" refers to the site on an antigen or hapten to which a specific antibody molecule or specific cell surface receptor binds.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, will stimulate a host's immune system to make a cellular antigen-specific immune response when the antigen is presented, or a humoral antibody response. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols,* supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol.* (1982) 157:105-132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publ. Nos. WO 96/04301, WO 94/01778, WO 95/33053, WO 92/08734, which applications are herein incorporated by reference in their entireties.

As used herein the term "T-cell epitope" refers to a feature of a peptide structure which is capable of inducing T-cell immunity towards the peptide structure or an associated hapten. T-cell epitopes generally comprise linear peptide determinants that assume extended conformations within the peptide-binding cleft of MHC molecules, (Unanue et al., *Science* (1987) 236:551-557). Conversion of polypeptides to MHC class II-associated linear peptide determinants (generally between 5-14 amino acids in length) is termed "antigen processing" which is carried out by antigen presenting cells (APCs). More particularly, a T-cell epitope is defined by local features of a short peptide structure, such as primary amino acid sequence properties involving charge and hydrophobicity, and certain types of secondary structure, such as helicity, that do not depend on the folding of the entire polypeptide. Further, it is believed that short peptides capable of recognition by helper T-cells are generally amphipathic structures comprising a hydrophobic side (for interaction with the MHC molecule) and a hydrophilic side (for interacting with the T-cell receptor), (Margalit et al., *Computer Prediction of T-cell Epitopes, New Generation Vaccines* Marcel-Dekker, Inc, ed. G. C. Woodrow et al., (1990) pp. 109-116) and further that the amphipathic structures have an α-helical configuration (see, e.g., Spouge et al. *J. Immunol.* (1987) 138:204-212; Berkower et al. *J. Immunol.* (1986) 136:2498-2503).

Hence, segments of proteins which include T-cell epitopes can be readily predicted using numerous computer programs. (See e.g., Margalit et al., *Computer Prediction of T-cell Epitopes, New Generation Vaccines* Marcel-Dekker, Inc, ed. G. C. Woodrow et al., (1990) pp. 109-116). Such programs generally compare the amino acid sequence of a peptide to sequences known to induce a T-cell response, and search for patterns of amino acids which are believed to be required for a T-cell epitope.

An "immunological response" to a polypeptide or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition, such as an immunogenic composition, or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic" polypeptide or composition is one which elicits an immunological response as defined above.

A "recombinant" protein is a protein which retains the desired activity and which has been prepared by recombinant DNA techniques as described herein. In general, the gene of interest is cloned and then expressed in transformed organisms, as described further below. The host organism expresses the foreign gene to produce the protein under expression conditions.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.nih.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* supra; *Nucleic Acid. Hybridization,* supra.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

By "nucleic acid immunization" is meant the introduction of a nucleic acid molecule encoding one or more selected antigens into a host cell, for the in vivo expression of the antigen or antigens. The nucleic acid molecule can be introduced directly into the recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, chimeric antigens which combine HBsAg with portions of HCV proteins enhance the presentation to the immune system of weakly immunogenic HCV proteins due to the strong antigenicity of HBsAg. Virus-like particles typically contain a membrane envelope in which are embedded one or more viral envelope proteins. Virus-like particles are secreted by a cell infected with a virus or a cell transfected with a nucleic acid molecule encoding one or more viral proteins.

Virus-like particles are an especially advantageous form of antigen presentation. Virus-like particles containing HBsAg chimeras combine the highly antigenic nature of HBsAg itself with the desirable presentation of other antigens at the surface of a particulate preparation.

The present invention provides methods and materials which enable the production of chimeric HBV/HCV antigens in the form of virus-like particles for the production of immunogenic compositions, such as vaccines. Utilizing co-expression of HBsAg together with the chimeric antigens, it is now possible to include large segments of HCV envelope glycoproteins fused to HBsAg in the form of virus-like particles. Such particles are especially well suited for use in immunogenic compositions.

The strategy for preparing HBV/HCV virus-like particles depends first on the production of one or more chimeric antigens for display in the particles. Such chimeric antigens are fusion proteins that comprise a substantially complete S domain of an HBsAg polypeptide (termed "sAg" herein) and an immunogenic HCV polypeptide or fragment thereof. An S domain of HBsAg, or any other polypeptide of the invention, is "substantially complete" if it contains the native sequence of the polypeptide with or without minor deletions of one or a few amino acids from either the N-terminal or C-terminal regions or within the polypeptide. For example the HBsAg S domain can be truncated by a few amino acids, i.e., up to about 3, 5, 7, or 10 amino acids, without greatly affecting either its antigenicity or ability to cause the formation of virus-like particles. Linker sequences of any desired length, preferably no more than a few amino acids, can be added between the polypeptides joined together to form the fusion protein. Either preS2 (formerly called preS) or both preS2 and preS1 domains of HBsAg can also be included at the amino terminus of the HBsAg polypeptide if desired.

Valenzuela, et al. (1982) Nature 298:347-350, describes the gene for HbsAg. See, also, Valenzuela, et al. (1979) Nature 280:815-819. Proteins derived from the HBV surface, such as the surface antigen, sAg, as well as the presurface sequences, preS1 and preS2, and any combination of these sequences, can spontaneously form particles upon expression in a suitable host cell, such as upon expression in mammalian, insect, yeast or Xenopus cells. Thus, as explained above, HCV/HBV virus-like particles for use in the present invention can include particle-forming polypeptides of sAg, preS1 and/or preS2, as well as particle-forming polypeptides from any combination of the above, such as sAg/preS1, sAg/preS2, and sAg/preS1/preS2. See, e.g., "HBV Vaccines—from the laboratory to license: a case study" in Mackett, M. and Williamson, J. D., Human Vaccines and Vaccination, pp. 159-176, for a discussion of HBV structure; and U.S. Pat. Nos. 4,722,840, 5,098,704, 5,324,513, 5,965,140, incorporated herein by reference in their entireties, Beames et al., J. Virol. (1995) 69:6833-6838, Birnbaum et al., J. Virol. (1990) 64:3319-3330, Zhou et al., J. Virol. (1991) 65:5457-5464, for descriptions of the recombinant production of various HBV particles.

HCV has a genome that contains a single open reading frame of approximately 9.5 kb, which is transcribed into a polyprotein. The HCV polyprotein is cleaved to form at least ten distinct products, which are $NH_2$-Core-E1-E2-p7-NS2-NS3-NS4a-NS4b-NS5a-NS5b-COOH. The HCV E1 and E2 proteins are postranslationally glycosylated. The full-length sequence of the polyprotein is disclosed in European Publ. No. 388,232 and U.S. Pat. No. 6,150,087, incorporated herein by reference in their entireties. Moreover, sequences for the above HCV polyprotein products, and immunogenic polypeptides derived therefrom, are known (see, e.g., U.S. Pat. No. 5,350,671, incorporated herein by reference in its entirety). For example, a number of general and specific immunogenic polypeptides, derived from the HCV polyprotein, have been described. See, e.g., Houghton et al., European Publ. Nos. 318,216 and 388,232; Choo et al. Science (1989) 244:359-362; Kuo et al. Science (1989) 244:362-364; Houghton et al. Hepatology (1991) 14:381-388; Chien et al. Proc. Natl. Acad. Sci. USA (1992) 89:10011-10015; Chien et al. J. Gastroent. Hepatol. (1993) 8:S33-39; Chien et al., International Publ. No. WO 93/00365; Chien, D. Y., International Publ. No. WO 94/01778. These publications provide an extensive background on HCV generally, as well as on the manufacture and uses of HCV polypeptide immunological reagents. For brevity, therefore, the disclosure of these publications is incorporated herein by reference.

Any desired HCV polypeptide can be utilized as part of the chimeric antigen, including, for example, the E1 and/or E2 envelope glycoproteins of HCV. The E1 glycoprotein corresponds to amino acid residues 192 to 383, and E2 extends from approximately amino acid 384 to amino acid 746 in most HCV strains. See Choo et al. (1991) Proc. Natl. Acad. Sci. USA 88:2451-2455. Preferred E1 polypeptides are those beginning at any amino acid residue from any of positions 192-360 of the HCV polyprotein and extending any desired length up to and including residue 383. Preferred E2 polypeptides are those beginning at any amino acid residue from positions 384-725 of the HCV polyprotein and extending any desired length up to and including residue 746. A fragment of the E1 or E2 glycoproteins which is utilized in the chimeric antigen should preferably comprise an epitope, domain, or other structural unit which is immunogenic.

An E1 or E2 glycoprotein or fragment thereof for use in a chimeric antigen, will preferably retain or resemble its native conformation. If a substantially native conformation is retained for the HCV polypeptide in the fusion protein containing HBsAg, then antibodies generated to the HCV polypeptide will recognize and bind to the corresponding polypeptide in HCV.

Other HCV polypeptides may also be used in the chimeric antigens of the invention. For example, HCV polypeptides derived from the Core region, such as polypeptides derived from the region found between amino acids 1-191; amino acids 10-53; amino acids 10-45; amino acids 67-88; amino acids 86-100; 81-130; amino acids 121-135; amino acids 120-130; amino acids 121-170; and any of the Core epitopes identified in, e.g., Houghton et al., U.S. Pat. No. 5,350,671; Chien et al. *Proc. Natl. Acad. Sci. USA* (1992) 89:10011-10015; Chien et al. *J. Gastroent. Hepatol.* (1993) 8:S33-39; Chien et al., International Publ. No. WO 93/00365; Chien, D. Y., International Publ. No. WO 94/01778; and U.S. Pat. No. 6,150,087, the disclosures of which are incorporated herein by reference in their entireties, will find use with the subject chimeric molecules.

Additionally, polypeptides derived from the nonstructural regions of the virus will also find use herein. The NS3/4a region of the HCV polyprotein has been described and the amino acid sequence and overall structure of the protein are disclosed in Yao et al. *Structure* (November 1999) 7:1353-1363. See, also, Dasmahapatra et al., U.S. Pat. No. 5,843,752, incorporated herein by reference in its entirety. As explained above, either the native sequence or immunogenic analogs can be used in the subject formulations. Dasmahapatra et al., U.S. Pat. No. 5,843,752 and Zhang et al., U.S. Pat. No. 5,990,276, both describe analogs of NS3/4a and methods of making the same.

Additionally, multiple epitope fusion antigens (termed "MEFAs"), as described in International Publ. No. WO 97/44469, may be used in the subject chimeras. Such MEFAs include multiple epitopes derived from two or more of the various viral regions. The epitopes are preferably from more than one HCV strain, thus providing the added ability to protect against multiple strains of HCV in a single vaccine.

Moreover, polypeptides for use in the subject chimeras may be derived from the NS3 region of the HCV polyprotein. A number of such polypeptides are known, including, but not limited to polypeptides derived from the c33c and c100 regions, as well as fusion proteins comprising an NS3 epitope, such as c25. These and other NS3 polypeptides are useful in the present compositions and are known in the art and described in, e.g., Houghton et al, U.S. Pat. No. 5,350,671; Chien et al. *Proc. Natl. Acad. Sci. USA* (1992) 89:10011-10015; Chien et al. *J. Gastroent. Hepatol.* (1993) 8:S33-39; Chien et al., International Publ. No. WO 93/00365; Chien, D. Y., International Publ. No. WO 94/01778; and U.S. Pat. No. 6,150,087, the disclosures of which are incorporated herein by reference in their entireties.

It is readily apparent that a multitude of HCV polypeptides may be used in the subject chimeric molecules or may be coadministered therewith, in order to provide an immune response against the HCV antigen in question.

As explained above, the HCV antigens may be used in their entireties or immunogenic fragments thereof, as well as immunogenic variants, can be combined with an HBsAg polypeptide to form the chimeric antigen by fusion of the gene sequences encoding the desired polypeptide sequences, in proper reading frame, using standard techniques available in the art. Thus, the HBV or HCV polypeptides described for use in the invention can be modified by deletions, insertions, or conservative amino acid substitutions, provided that a substantially native conformation is retained for the HCV epitope intended for use as an immunogen. Preferably, the HCV polypeptide or polypeptide fragment is chosen so that, when expressed in a fusion protein with HBsAg, it substantially retains the native conformation of the corresponding portion of the HCV protein from which it was derived, i.e., the approximate conformation existing in a mature HCV virion.

It should be noted that for convenience, the various HCV regions are generally defined with respect to the amino acid number relative to the polyprotein encoded by the genome of HCV-1a, as described in Choo et al. (1991) *Proc Natl Acad Sci USA* 88:2451, with the initiator methionine being designated position 1. However, the polypeptides for use with the present invention are not limited to those derived from the HCV-1a sequence. Any strain or isolate of HCV can serve as the basis for providing antigenic sequences for use with the invention. In this regard, the corresponding regions in another HCV isolate can be readily determined by aligning sequences from the two isolates in a manner that brings the sequences into maximum alignment.

Various strains and isolates of HCV are known in the art, which differ from one another by changes in nucleotide and amino acid sequence. For example, isolate HCV J1.1 is described in Kubo et al. (1989) Japan. Nucl. Acids Res. 17:10367-10372; Takeuchi et al. (1990) Gene 91:287-291; Takeuchi et al. (1990) J. Gen. Virol. 71:3027-3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524-9528 and Takamizawa et al., (1991) J. Virol. 65:1105-1113, respectively. HCV-1 isolates are described by Choo et al. (1990) Brit. Med. Bull. 46:423-441; Choo et al. (1991) Proc. Natl. Acad. Sci. USA 88:2451-2455 and Han et al. (1991) Proc. Natl. Acad. Sci. USA 88:1711-1715. HCV isolates HC-J1 and HC-J4 are described in Okamoto et al. (1991) Japan J. Exp. Med. 60:167-177. HCV isolates HCT 18~, HCT 23, Th, HCT 27, EC1 and EC10 are described in Weiner et al. (1991) Virol. 180:842-848. HCV isolates Pt-1, HCV-K1 and HCV-K2 are described in Enomoto et al. (1990) Biochem. Biophys. Res. Commun. 170:1021-1025. HCV isolates A, C, D & E are described in Tsukiyama-Kohara et al. (1991) Virus Genes 5:243-254.

Coding sequences for naturally occurring HCV polypeptides for use in the nucleic acid molecules or vectors of the invention can be obtained from any of the above cited strains of HCV or from newly discovered isolates isolated from tissues or fluids of infected patients. In choosing HCV polypeptides or their fragments from different HCV strains for use in a chimeric antigen of the invention, it is preferred that the nucleotide or amino acid sequences be aligned for maximum overlap between strains. This can be accomplished, for example, by compensating for insertions or deletions of amino acids so that the greatest possible overlap between strains is obtained prior to selecting a sequence for incorporation in the chimeric antigen. If a sequence disclosed herein is selected from another HCV strain, then preferably the corresponding sequence, i.e., the sequence which is aligned to be identical at the greatest possible number of residues to the disclosed sequence, will be selected. Modified sequences which do not occur in nature can also be used. A "nucleic acid molecule" according to the invention can be any nucleic acid such as DNA or RNA, either single or double stranded, or any analog or chemical derivative thereof which encodes a fusion protein of the invention or portion thereof or any HBsAg or portion thereof.

Nucleic acid molecules of the invention can be cloned into expression vectors and transformed into, for example, bacterial, yeast, plant, insect, or mammalian cells so that the chimeric antigens and virus-like particles of the invention can be expressed in and isolated from cell culture. Nucleic acid molecules can be contained within a plasmid, such as pBR322, pUC, ColE1, or related plasmids such as pCMV6a (see U.S. Pat. No. 5,688,688) or plasmids derived therefrom. Nucleic acid molecules can also be contained within a viral vector, such as any vector derived from adenovirus, Sindbis virus, simian virus 40, cytomegalovirus, and retroviruses such as murine sarcoma virus, mouse mammary tumor virus, Moloney murine leukemia virus, and Rous sarcoma virus. Bacterial vectors, such as *Salmonella* ssp., *Yersinia enterocolitica, Shigella* spp., *Vibrio cholerae, Mycobacterium* strain BCG, and *Listeria monocytogenes* can also be used. Minichromosomes such as MC and MC1, bacteriophages, cosmids, and replicons can be used as well.

Any suitable expression vector can be constructed or utilized to express any form of HBsAg or any chimeric antigen of the invention. A preferred vector is pCMVII, a pUC 19-based cloning vector designed for expression in mammalian cells. pCMVII comprises the following elements: human CMV IE enhancer/promoter, human CMV intron A, a human tissue plasminogen activator (tPA) leader, a bovine growth hormone poly A terminator (BGHt), a ColE1 origin of replication, and an Amp R ampicillin resistance gene (FIGS. 1A and 1B-1F, SEQ ID NO:1). pCMVII-pS2-sAg can be used for expression of preS2-HBsAg (FIGS. 2A and 2B-2I, SEQ ID NOS:2 and 3). In pCMVII-pS2-sAg, the coding sequences for the preS2 and S domains of HBsAg have been inserted into pCMVII between CMV intron A and BGHt; this vector can also be modified by adding the coding sequences for the preS1 domain or removing the preS2 domain. Chimeric antigens containing HBsAg together with epitopes of HCV proteins can be constructed similar to pCMVII opti 330 E1/sAg (FIGS. 3A and 3B-3I, SEQ ID NOS:4 and 5) or pCMVII-E2661-sAg (FIGS. 4A and 4B-4F, SEQ ID NOS:6 and 7). These vectors are provided by way of example and are not intended to limit the scope of the invention. Isolated and purified pCMVII vectors containing an insert encoding HBsAg or a chimeric antigen can be dissolved in sterile 0.9% saline buffer or another suitable buffer prior to use.

The expression of chimeric antigens for use as immunogens requires transfection of eukaryotic cells with an expression vector. Any suitable eukaryotic cell line can be used, for example CHO cells or COS cells. A nucleic acid molecule that encodes a chimeric antigen can be incorporated into any vector suitable for transfection, for example a plasmid vector or a viral vector. If a viral vector is used, it will preferably produce defective, non-infectious viral particles so that the risk of contamination with infectious virus in a vaccine preparation is minimized.

Transfection can be performed by any known method and can result in either transient transfection or stable transfection. Stable transfection is preferred to establish a cell line producing HBV/HCV virus-like particles. Methods for obtaining stable transfection are well known and include, for example, selection for spontaneously stable transfectants, transfection with immortalizing genes (see, e.g., Katakura et al., Methods Cell Biol. (1998) 57:69-91), and selection for genes providing resistance to antibiotics such as hygromycin B and neomycin. A preferred method for CHO cells involves selection for cells transfected with dihydrofolate reductase followed by amplification of the transgene using methotrexate (see Wurm et al., Ann. N.Y. Acad. Sci. (1996) 782:70-78).

Co-expression of chimeric antigens with HBsAg results in formation and secretion of virus-like particles. Optimum secretion of virus-like particles requires a sufficient quantity of expression of HBsAg in relation to the expression of chimeric antigen, and higher quantities of HBsAg expression generally improve the efficiency of chimeric antigen secretion. Secretion of chimeric antigen as virus-like particles can be optimized by varying the ratio of the coding sequences for HBsAg to the coding sequences for the chimeric antigen. Generally, useful secretion of virus-like particles will be obtained at a ratio of HBsAg coding sequences to chimeric antigen coding sequences of about 1:1, 2:1, 3:1, 4:1, 5:1, 7:1, 10:1, 20:1, 30:1, 40:1, 50:1, or 100:1. Ratios less than 1:1 provide reduced yield of virus-like particles containing chimeric antigen, while high ratios greater than 100:1 dilute out the chimeric antigen and eventually will limit the utility of the particles because of dilution of the chimeric antigen with HBsAg.

One strategy for transfecting host cells with the vectors of the invention, either for in vitro production of virus-like particles or for immunization of a host organism using a nucleic acid vaccine, is to provide two or more separate vectors, one that encodes HBsAg and one or more that each encode a chimeric antigen. Another strategy is to include both HBsAg and one or more chimeric antigens in a single construct. For example, an expression vector having a single open reading frame could have a coding sequence for HBsAg under control of a promoter, followed by sequences encoding one or more chimeric antigens, each preceded by an internal ribosomal entry site (IRES, see, e.g., Martinez-Salas (1999) Curr. Op. Biotechnol. 10: 458-464). Thus, the invention encompasses the use either of a single immunogenic polypeptide or multiple distinct immunogenic polypeptides in a single virus-like particle. Optionally, expression of immunogenic polypeptides can be regulated by including promoter and/or enhancer sequences in the expression vector which respond to activators introduced into the transfected cells.

Cells that have been transfected with plasmid or viral vectors expressing chimeric HBV/HCV antigens together with HBsAg can be analyzed to determine whether each antigen is being expressed and secreted in the form of virus-like particles. Any standard immunological assay can be used to detect HBV and HCV antigens, including, for example, chemiluminescence assays (see, e.g., Magic Lite assay in Examples 1-4; Woodhead, J. S. and Weeks, I. (1989) J. Biolumin. Chemilumin. 4:611-14), ELISA, and radioimmunoassays. Where an antigen is produced by transfected cells in culture, the amount of secretion of the antigen into the culture medium can be ascertained by comparing the amount of antigen in the culture medium with the amount remaining in lysed cells. The presence of virus-like particles can be confirmed by sedimentation of such particles from the culture medium into a density gradient, for example a sucrose density gradient (see Examples 1-3).

While expression in a mammalian cell line is preferred, other systems may also be employed to express virus-like particles of the invention. For example, yeast cell culture may be used (see U.S. Pat. No. 5,098,704, incorporated herein by reference), in which case virus-like particles can be harvested by disrupting the cells using agitation with glass beads or another suitable method.

Generally, the proteins of the subject invention will naturally aggregate to form particles in the expression host. The particles may be enveloped having a lipid membrane coat, which may or may not include membrane proteins encoded by the virus. Alternatively, the particles may not include the lipid membrane or the membrane may be present initially or may be removed, in whole or in part. U.S. Pat. Nos. 4,722,840 and 5,965,140, incorporated herein by reference in their entireties, describe hybrid particles comprised of a particle-forming fragment of a structural protein from a virus, such as a particle-forming fragment of hepatitis B virus (HBV) surface antigen (HBsAg), fused to a heterologous polypeptide.

HBV/HCV virus-like particles can be purified after being harvested from a culture medium or cell suspension and before being used in an immunogenic composition. Any method can be used that is known to separate virus-like particles or viruses from surrounding proteins, lipids, nucleic acids, membranes, intact cells, and the like. Especially preferred are affinity chromatography methods; for example, an immobilized monoclonal antibody specific for HBsAg can be used. Additional suitable methods are gel filtration chromatography, ion exchange chromatography, and density gradient sedimentation. Methods for isolated chimeric virus-like particles are described in, e.g., U.S. Pat. Nos. 4,722,840 and 5,965,140, incorporated herein by reference in their entireties.

Any composition of the invention, such as a fusion protein, a virus-like particle, or a nucleic acid molecule, can be used as an "immunogenic composition." An immunogenic composition preferably generates an immune response, as defined above, such as an antibody or a T-cell response, in a mammal to whom it is administered. An immunogenic composition of the invention can be, but is not limited to, a vaccine or a combination vaccine, e.g., an immunogenic composition that produces an immune response to more than one immunogen. Moreover, the chimeric proteins of the invention may be formulated into "antigenic compositions," e.g., compositions that include epitopes to which a specific antibody molecule or specific cell surface receptor binds.

Immunogenic and antigenic compositions containing HBV/HCV virus-like particles or a nucleic acid molecule encoding proteins which form virus-like particles can be administered to a mammal, such as a mouse, rabbit, baboon, chimpanzee, or human, to elicit anti-HCV antibodies in vivo. Injection of an immunogenic composition of the invention preferably results in the synthesis of virus-like particles in the host. Therefore, Compositions comprising nucleic acids should include sequences encoding both HBsAg and chimeric antigens such as HBsAg-E1 and/or HBsAg-E2 fusion proteins, as well as fusions with other HCV polypeptides. The weight:weight ratio of nucleic acids encoding HBsAg to nucleic acids encoding chimeric antigens is preferably 1:1, 2:1, 5:1, 10:1, 20:1, 30:1, 50:1, or 100:1 and results in the formation of virus-like particles in the cells of the host and their secretion within the host. More preferably, the ratio is in the range of 5:1 to 20:1.

Virus-like particles or nucleic acid molecules of an antigenic or immunogenic composition can be combined with adjuvants, immunostimulatory molecules, or carriers, including but not limited to, MF59 (described below), poly(dl-lactide-co-glycolide) microparticles (PLG, see, e.g., Delgado et al. (1999) Vaccine 17: 2927-2938), LT toxins, immune stimulating complexes (ISCOMS, see, e.g., Mowat et al. (1999) Immunol. Lett. 65: 133-140), and QS21 (see Singh & O'Hagan (1999) Nat. Biotechnol. 17: 1075-1081).

For example, preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+ CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) detoxified mutants of a bacterial ADP-ribosylating toxin such as a cholera toxin (CT), a pertussis toxin (PT), or an $E.$ $coli$ heat-labile toxin (LT), particularly LT-K63, LT-R72, CT-S109, PT-K9/G129; see, e.g., WO 93/13302 and WO 92/19265; (7) other substances that act as immunostimulating agents to enhance the effectiveness of the composition; and (8) microparticles with adsorbed macromolecules, as described in copending U.S. patent application Ser. No. 09/285,855 (filed Apr. 2, 1999) and international Patent Application Serial No. PCT/US99/17308 (filed Jul. 29, 1999). Alum and MF59 are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

An immunogenic composition may also comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Liposomes, such as those described in U.S. Pat. No. 5,422,120, WO 95/13796, WO 91/14445, or EP 524,968 B1, as well as poly (dl-lactide-co-glycolide) microparticles (PLG, see, e.g., Delgado et al. (1999) Vaccine 17: 2927-2938), can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates.

Compositions of the invention generally contain pharmaceutically acceptable excipients, such as water, saline, glycerol, and ethanol, as well as substances such as wetting agents, emulsifying agents, or pH buffering agents.

The chimeric molecules of the present invention may be used for nucleic acid immunization, to generate an appropriate immune response, such as to activate HCV-specific T cells, using standard gene delivery protocols. Any method known in the art can be employed to package and deliver nucleic acid molecules of the invention, including nucleic acid molecules in an immunogenic composition. Methods for gene delivery are known in the art. See, e.g., U.S. Pat. Nos. 5,399,346, 5,580,859, 5,589,466, incorporated by reference herein in their entireties. For example, the coding sequences can be packaged in a viral vector, combined with lipid, peptoid excipients, PLG formulations, or gold particles. Preferably, an immunogenic composition is delivered as naked DNA or naked RNA. The expressed immunogenic polypeptide is preferably presented to the host immune system with native post-translational modifications, structure, and conformation.

For example, the constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097: 1-17; Straubinger et al., in *Methods of Enzymology* (1983), Vol. 101, pp. 512-527.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art. See, e.g., Straubinger et al., in METHODS OF IMMNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochim. Biophys. Acta.* (1975) 394:483-491. See, also, U.S. Pat. Nos. 4,663,161 and 4,871,488.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110-2209), or isolated from known sources using commonly available techniques.

A number of adenovirus vectors have also been described, such as adenovirus Type 2 and Type 5 vectors. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as but not limited to vectors derived from the Sindbis and Semliki Forest viruses, VEE, will also find use as viral vectors for delivering the gene of interest. For a description of Sindbis-virus derived vectors useful for the practice of the instant methods, see, Dubensky et al., *J. Virol.* (1996) 70:508-519; and International Publication Nos. WO 95/07995 and WO 96/17072.

Other vectors can be used, including but not limited to simian virus 40, cytomegalovirus. Bacterial vectors, such as *Salmonella* ssp. *Yersinia enterocolitica, Shigella* spp., *Vibrio cholerae,* Mycobacterium strain BCG, and *Listeria monocytogenes* can be used. Minichromosomes such as MC and MC1, bacteriophages, cosmids (plasmids into which phage lambda cos sites have been inserted) and replicons (genetic elements that are capable of replication under their own control in a cell) can also be used.

The chimeric constructs may also be encapsulated, adsorbed to, or associated with, particulate carriers. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

A wide variety of other methods can be used to deliver the constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest; and Felgner, P. L., *Advanced Drug Delivery Reviews* (1990) 5:163-187, for a review of delivery systems useful for gene transfer. One particularly effective method of delivering DNA-using electroporation is described in International Publication No. WO/0045823.

Additionally, biolistic delivery systems employing particulate carriers such as gold and tungsten, are useful for delivering the constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

The chimeric constructs can be delivered either directly to the vertebrate subject or, alternatively, delivered ex vivo, to cells derived from the subject and the cells reimplanted in the subject. For example, the constructs can be delivered as plasmid DNA, e.g., contained within a plasmid, such as pBR322, pUC, or Col E1.

Figure 6B:
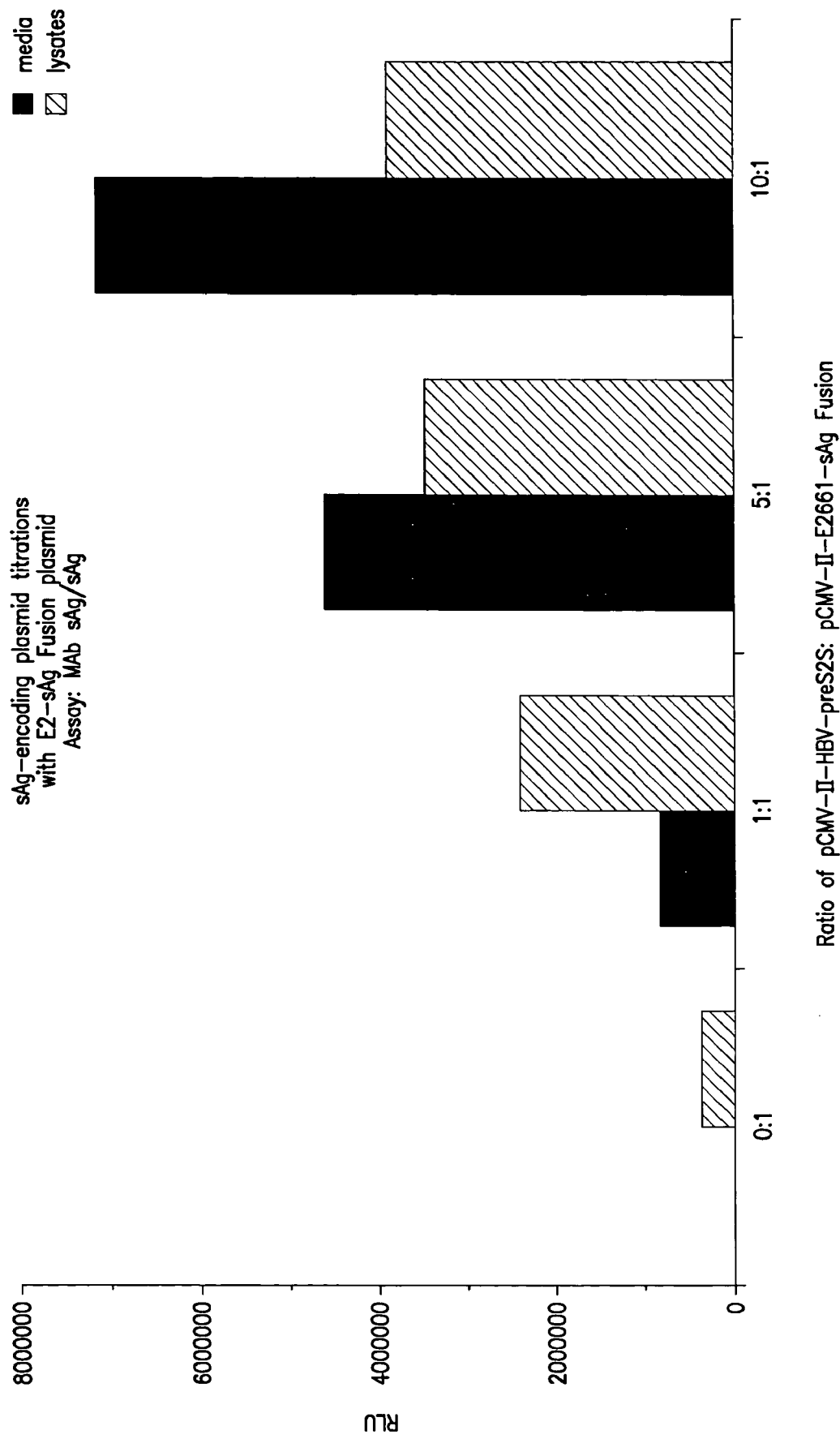

An immunogenic composition of the invention is administered in a manner compatible with the particular composition used and in an amount which is effective to elicit an anti-HCV polypeptide antibody titer, such as an anti-E2 or anti-E1 antibody titer. Administration can be by any means known in the art, including intramuscular, intradermal, intraperitoneal, or subcutaneous injection, including injection using a biological ballistic gun ("gene gun"). Electroporation or iontophoresis can also be used. Administration may also be intranasal or oral. For oral administration of an immunogenic composition, a protein carrier is preferably included. An immunogenic composition, including compositions comprising naked DNA or RNA, is preferably injected intramuscularly to a large mammal, such as a baboon, chimpanzee, or human, at a dose of 0.5, 0.75, 1.0, 1.5, 2.0, 2.5, 5 or 10 mg/kg. A composition comprising virus-like particles is preferably injected intramuscularly to a large mammal, such as a human, at a dose of 0.01, 0.05, 0.5, 0.75, 1.0, 1.5, 2.0, 2.5, 5 or 10 mg protein/kg body weight.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral, intranasal, and pulmonary administration, suppositories, and transdermal or transcutaneous applications (e.g., see WO98/20734), needles, and gene guns or hyposprays. Dosage treatment may be a single dose schedule or a multiple dose schedule. The composition may be administered in conjunction with other immunoregulatory agents.

Methods for the ex vivo delivery and reimplantation of transformed cells into a subject are known in the art and described in e.g., WO93/14778. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Immunogenic compositions comprising either HBV/HCV virus-like particles or nucleic acids encoding and expressing such virus-like particles can be administered either to a mammal that is not infected with HCV or can be administered to an HCV-infected mammal. The particular dosages of virus-like particles or nucleic acids will depend on a number of factors including, but not limited to, the species, age, and general condition of the mammal to which the composition is administered and the mode of administration of the composition. An effective amount of the composition of the invention can be readily determined using routine experimentation. In vivo models are well known and can be employed to identify appropriate doses. If desired, co-stimulatory molecules or adjuvants can also be provided before, after, or together with the immunogenic compositions. Immunogenic compositions can be administered more than once, as required for effective immunization. Administration of immunogenic compositions containing virus-like particles can be performed either before or after administration of immunogenic compositions containing nucleic acids, such that one form (protein or nucleic acid) provides a primary immunization and the other form boosts the immune response.

III. Experimental

Below are examples of specific embodiments for carrying out the present invention. The examples are offered for illustrative purposes only, and are not intended to limit the scope of the present invention in any way. Those of skill in the art will readily appreciate that the invention may be practiced in a variety of ways given the teaching of this disclosure.

Efforts have been made to ensure accuracy with respect to numbers used (e.g., amounts, temperatures, etc.), but some experimental error and deviation should, of course, be allowed for.

EXAMPLE 1

Detection of HBV Virus-Like Particles Using Sucrose Density Gradient Sedimentation Purified recombinant HBsAg particles were obtained in the form of a hepatitis B vaccine from Chiron Corp. Clinical Department. Two hundred fifty μL of a 37 μg/mL suspension in 0.03 M citrate, 0.26 M NaCl, 0.005% polysorbate 80 was loaded onto a 5-30% (wt-vol) sucrose gradient and centrifuged 4 hrs at 40,000 rpm in a Beckman SW41 rotor. Ten fractions were removed and assayed for HBsAg by the Magic Lite Assay. The results are shown in FIG. 5.

Magic Lite Assay

This describes a highly sensitive immunochemiluminescence assay used to detect HBV and HCV antigens. One hundred μL of sample was added to a 12×75 mm polystyrene tube. One hundred μL (30 μg) of a "capture" antibody was added to the sample. The capture antibody was covalently linked to paramagnetic particles by glutaraldehyde crosslinking a mixture of 6:1 paramagnetic particles:antibody. The tubes were vortexed and incubated in a 37° C. waterbath for 20 minutes. Next the tubes were placed on a magnetic rack where the paramagnetic particles (PMP) can aggregate. This allowed for washing and decanting. After the third wash, 100 μL of a "detecting" antibody, which was covalently linked to dimethylacridinium, was added and the tube was vortexed. The tubes were again incubated at 37° C. for 20 minutes and then placed on a magnetic rack for washing and decanting. After the third wash, the tubes were placed in a Ciba Corning Magic Lite chemiluminometer to measure the analyte bound. Results were expressed in arbitrary units of light intensity (relative light units, RLU).

Antibodies

Anti-sAg was provided by Chiron Diagnostics (Walpole, Mass.) and was directed against serotypes AYW and ADW. MAb 5E5/H7 was obtained from mice using HeLa E1/E2 amino acids 1-967 as an immunogen and recognizes the E2 epitope 384-655. MAb 3D5/C3 was also obtained from mice immunized with HeLa E1/E2 amino acids 1-967 and recognizes E1 epitope 211-217.

EXAMPLE 2

Expression of HBV/HCV Virus-Like Particles Containing Chimeric HBsAg-E2-661 Antigen in COS7 Cells Five μg of pCMV-II-E2661-sAg (FIG. 4A) and increasing amounts of pCMV-II-pS2-sAg (FIG. 2A) were prepared. Expression from pCMV-II-pS2-sAg resulted in a mixture of about 5-20% preS2-S-polypeptide, with the remainder being S-polypeptide. Ratios of sAg to E2661-sAg plasmids used were 0:1, 1:1, 5:1, and 10:1 on a μg DNA basis. The total amount of DNA in each tube was normalized to 55 μg by the addition of pCMV-km-Bgal. This mixture was transfected into COS7 cells using the LT1 transfection reagent from Panvera, as described below. At 48 hours post-transfection, media and soluble lysates (obtained by incubating cell monolayers in PBS with 0.1% NP40 and centrifuging to remove insoluble debris) were removed and assayed by the Magic Lite Assay, with capture by anti-sAg followed by detection with a conjugated anti-E2 MAb (5E5/H7, see Example 1) (FIG. 6A) or MAb sAg (FIG. 6B). Both E2 and sAg were increasingly secreted into the medium as the ratio of sAg:E2661-sAg was increased, with an optimum secretion at ratios in the range of 5:1 to 10:1.

Figure 5:
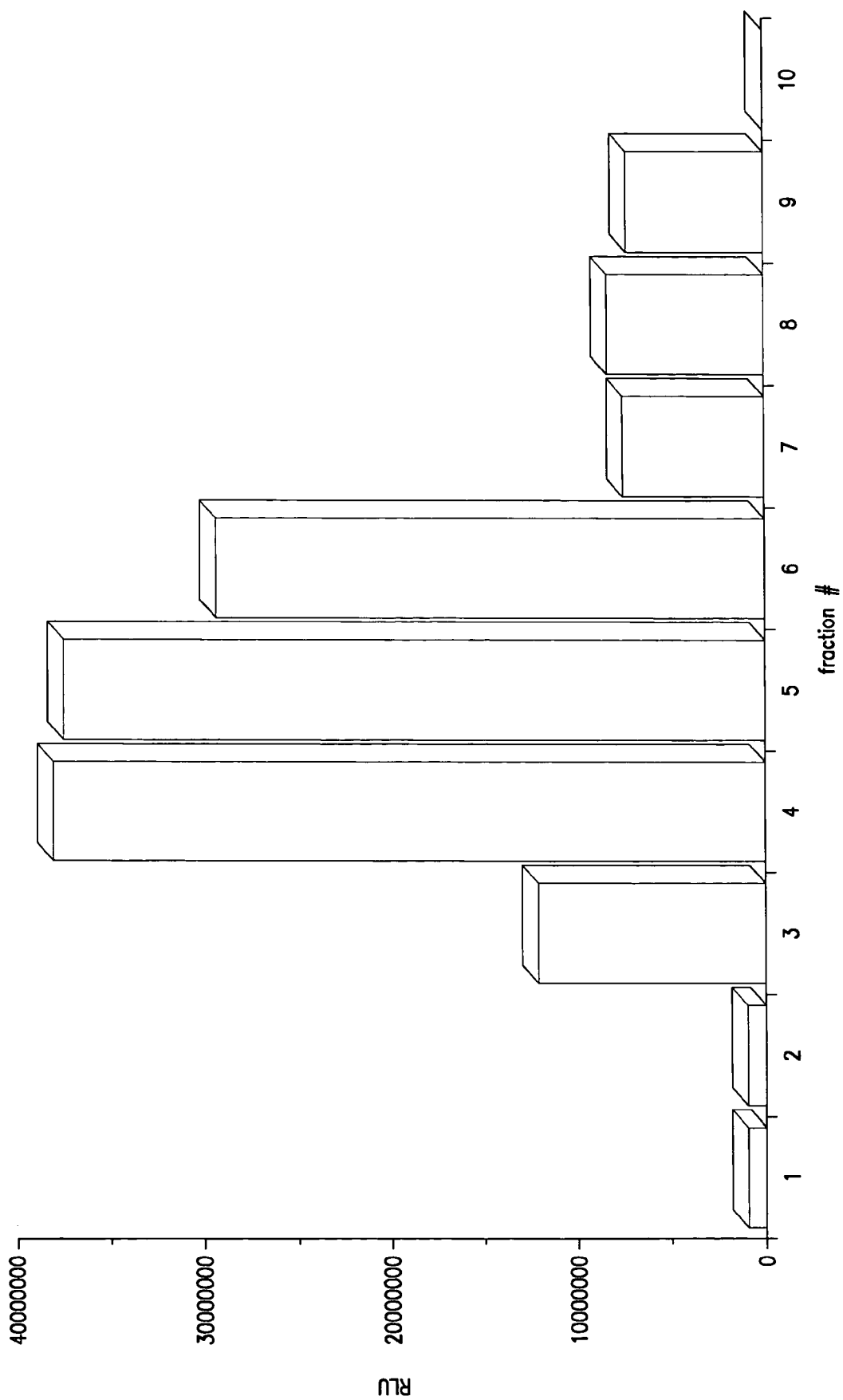
FIG. 5 shows the results of sucrose density gradient centrifugation of purified recombinant HBsAg virus-like particles. The experiment is described in Example 1.
Figure 7B:
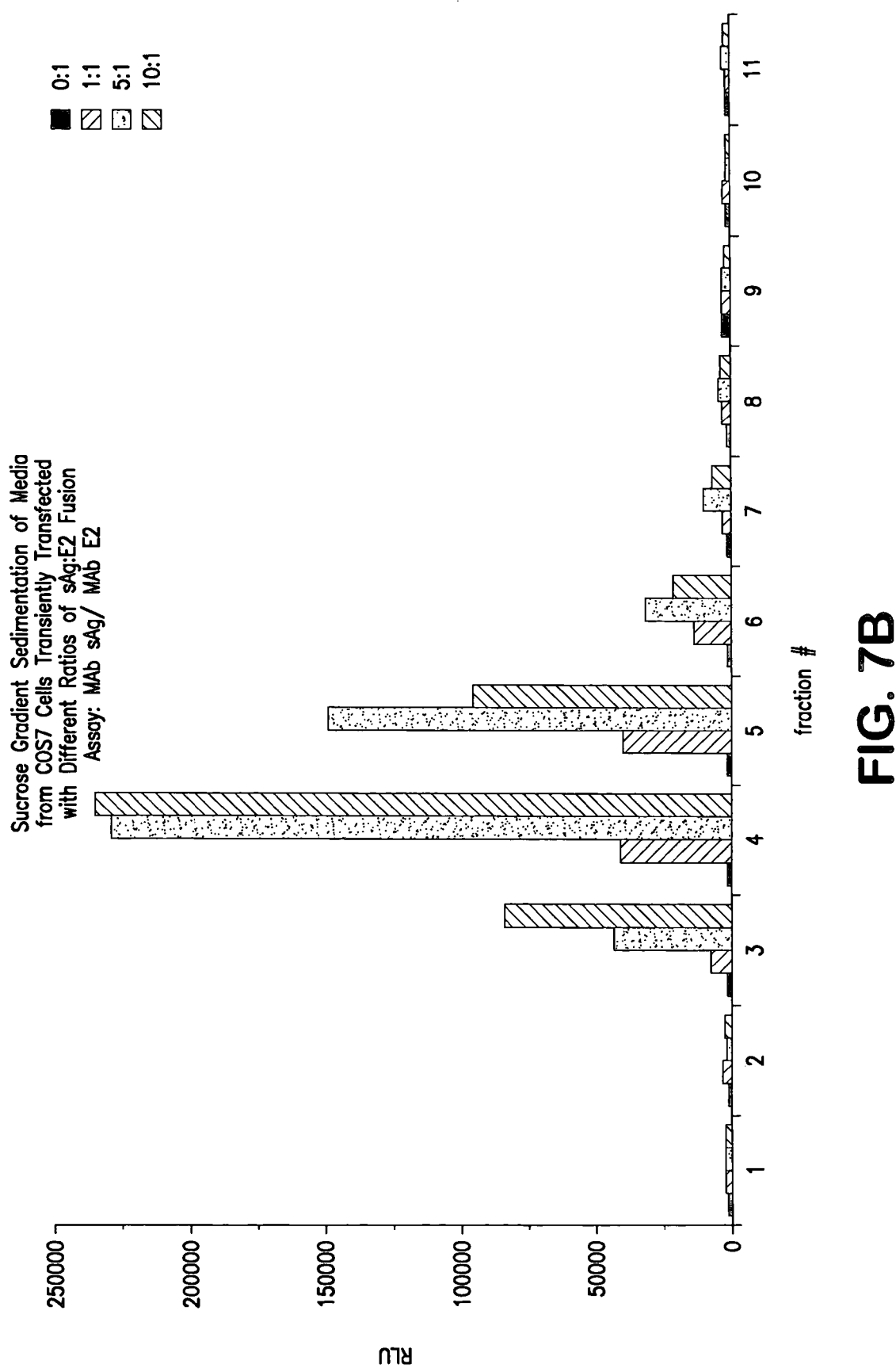
Figure 8A:
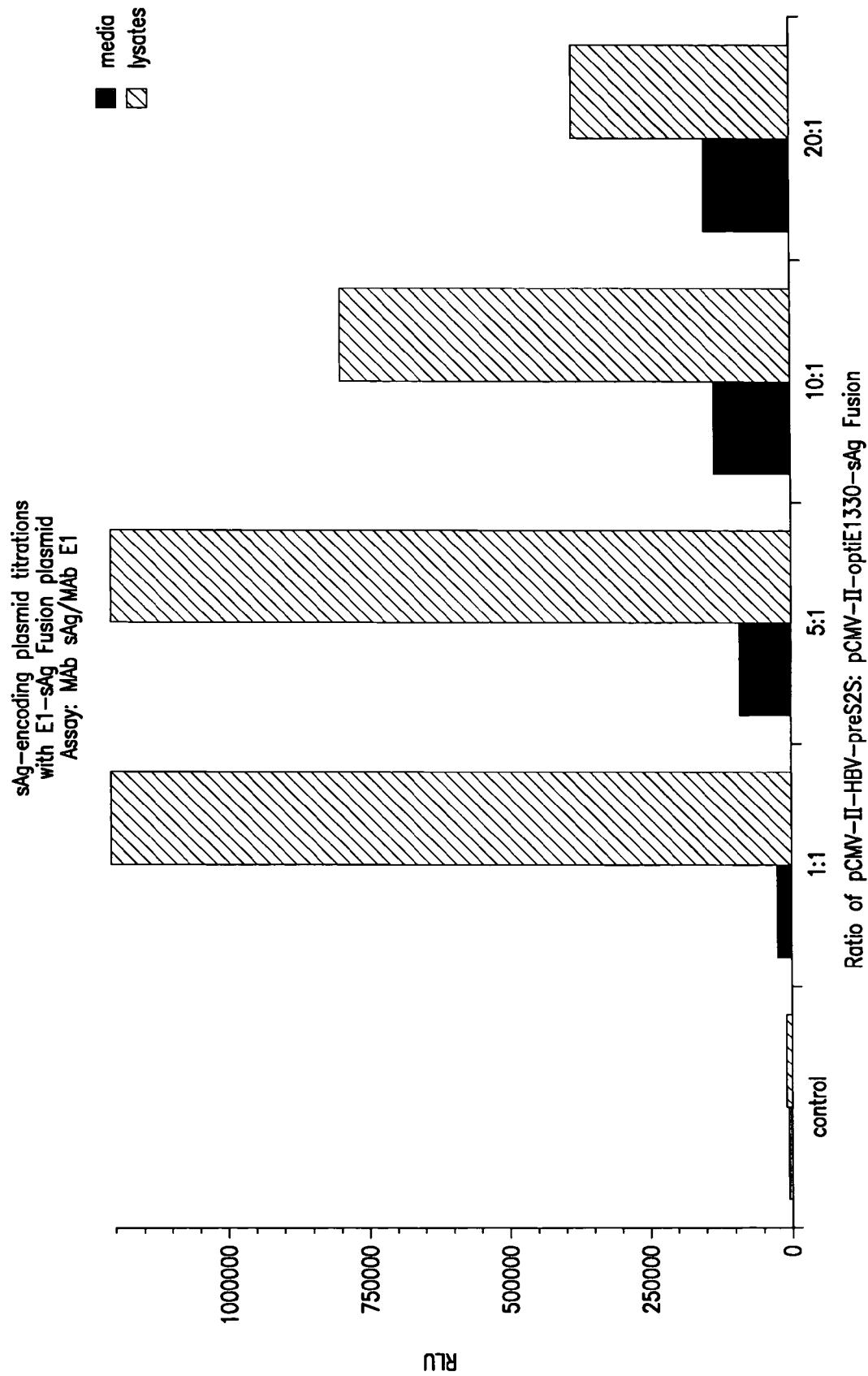
FIGS. 8A and 8B demonstrate the expression of HCVE1-HBsAg fusion protein in COS7 cells. Increasing amounts of sAg-encoding plasmid were expressed together with HCVE1-sAg fusion plasmid. The experiment is described in Example 3. The capture antibody was MAb sAg, and the detecting antibody was MAb E2 (FIG. 8A) or MAb sAg (FIG. 8B).
Figure 8B:
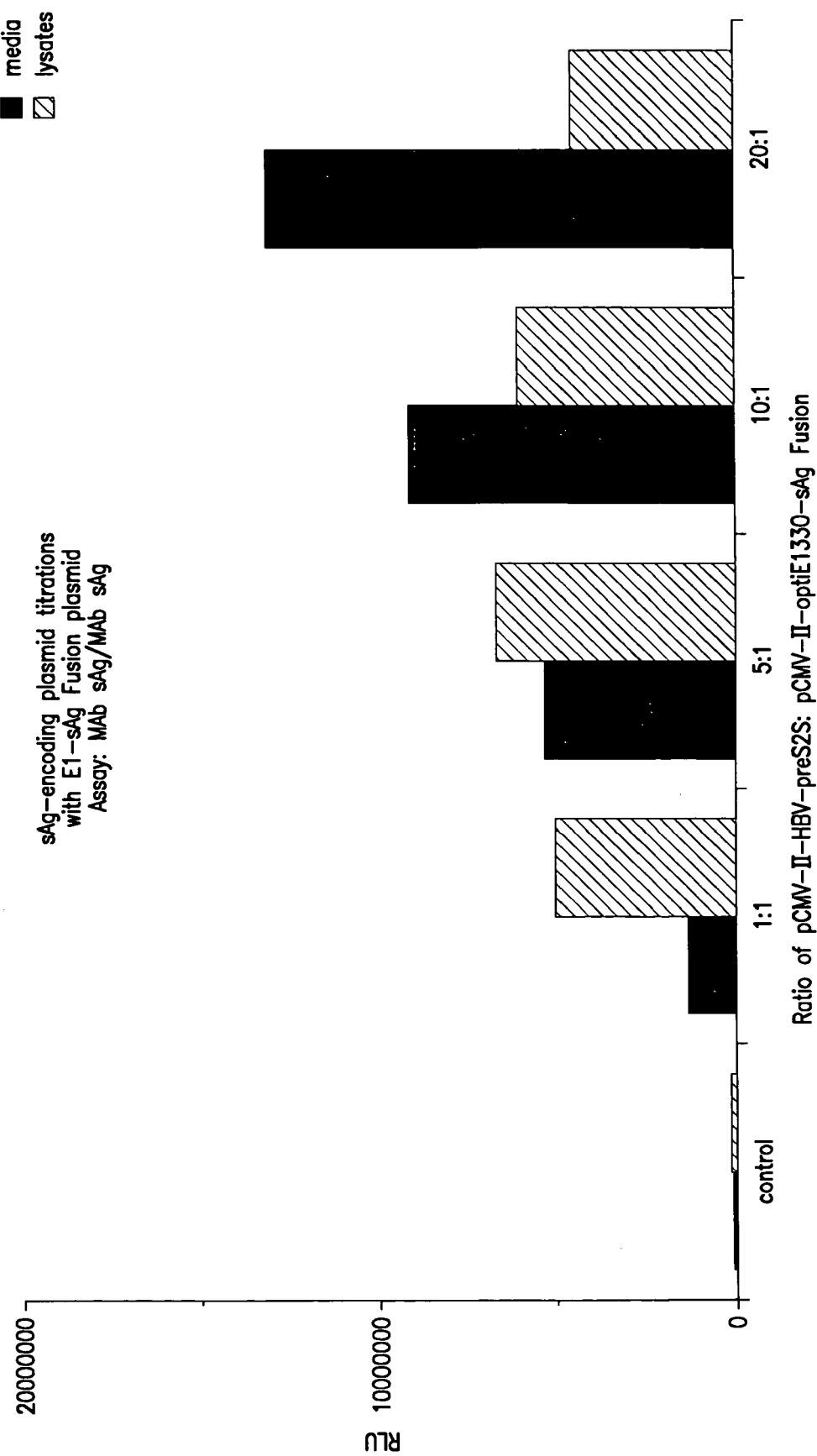
Figure 9A:
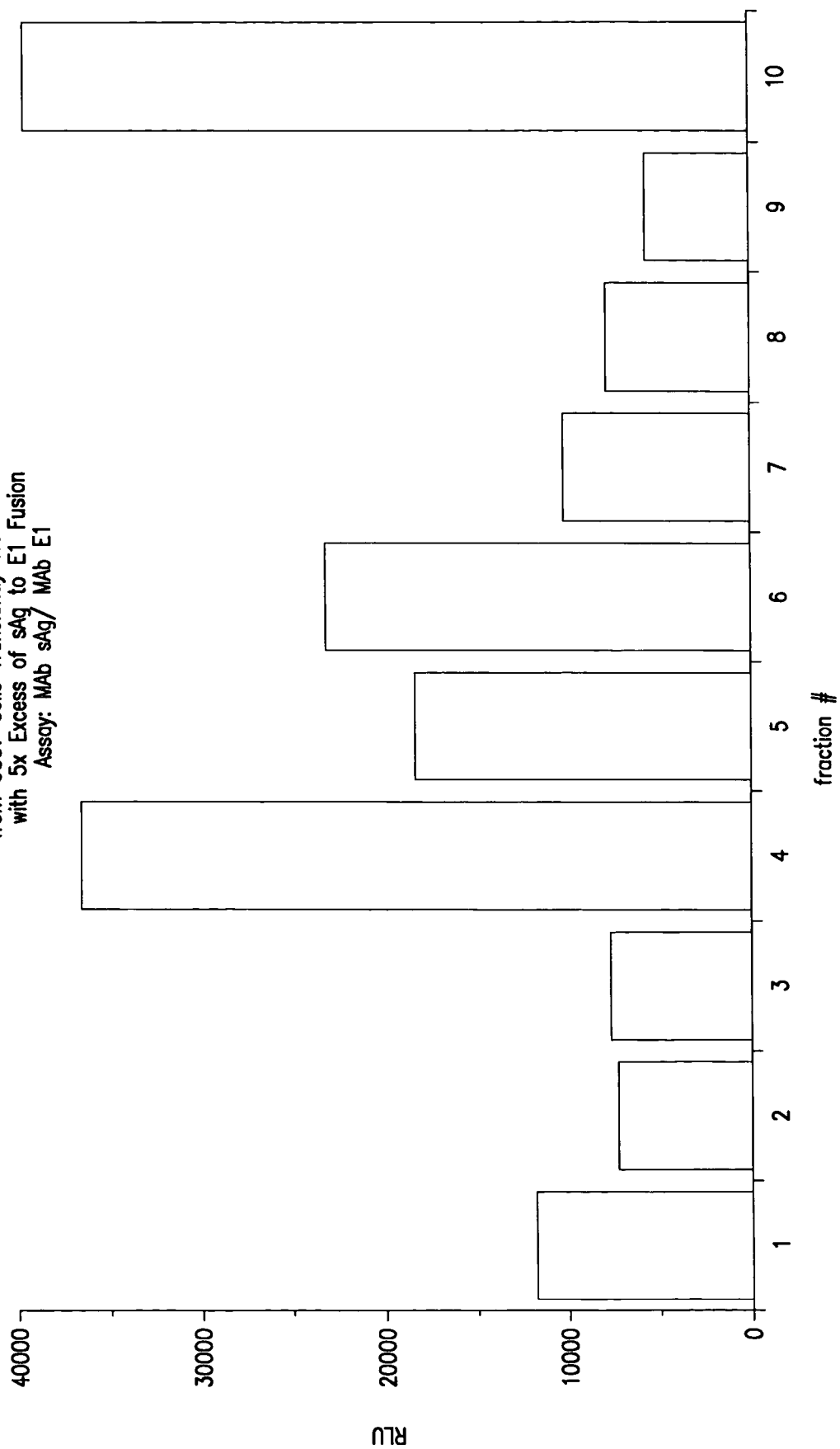
Figure 10A:
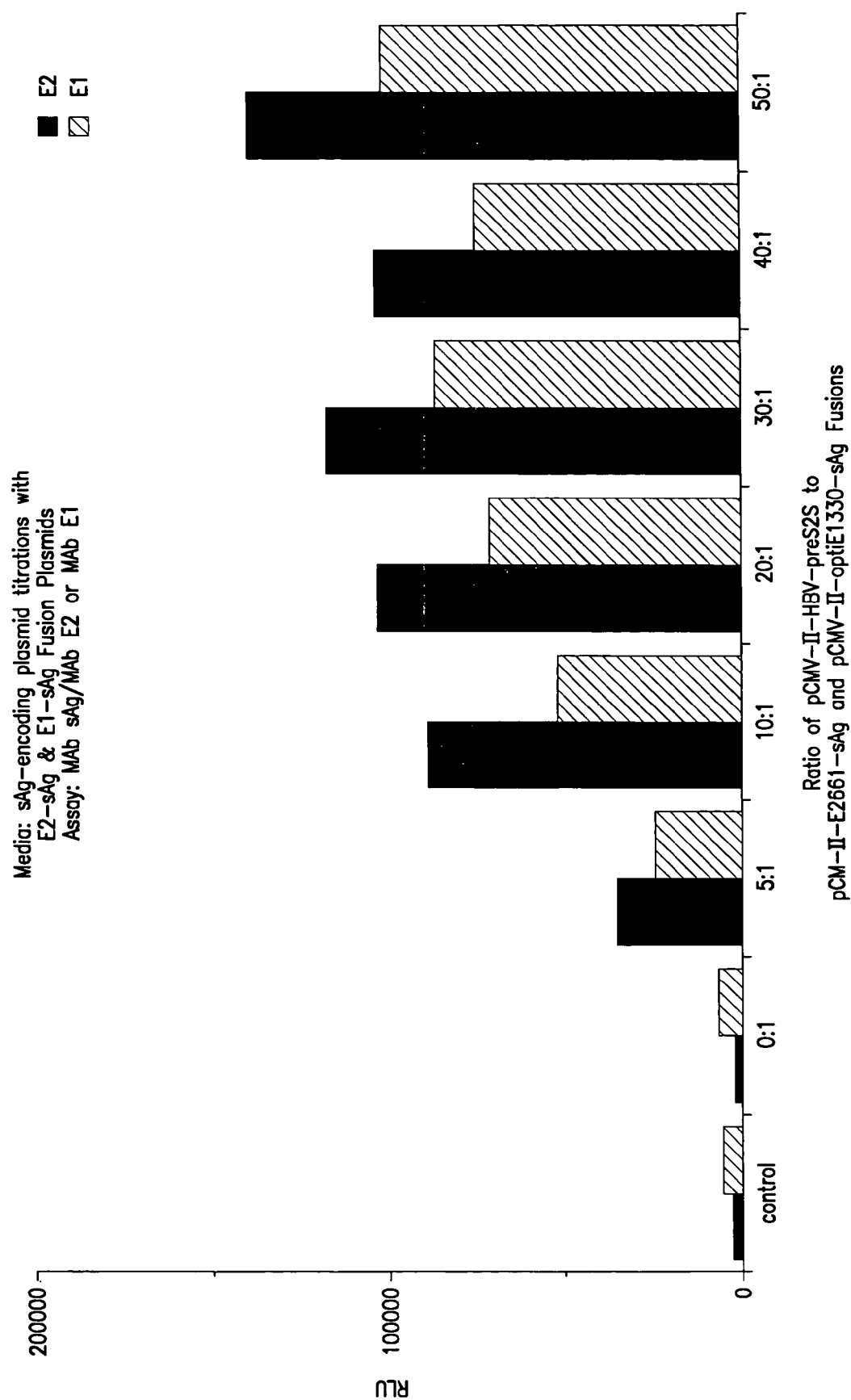
FIGS. 10A and 10B show the co-expression and secretion of E1-sAg and E2-sAg fusion proteins in COS7 cells. Increasing amounts of sAg-encoding plasmid were expressed together with constant amounts of both E1-sAg and E2-sAg fusion plasmids. The experiment is described in Example 4.
Figure 10B:
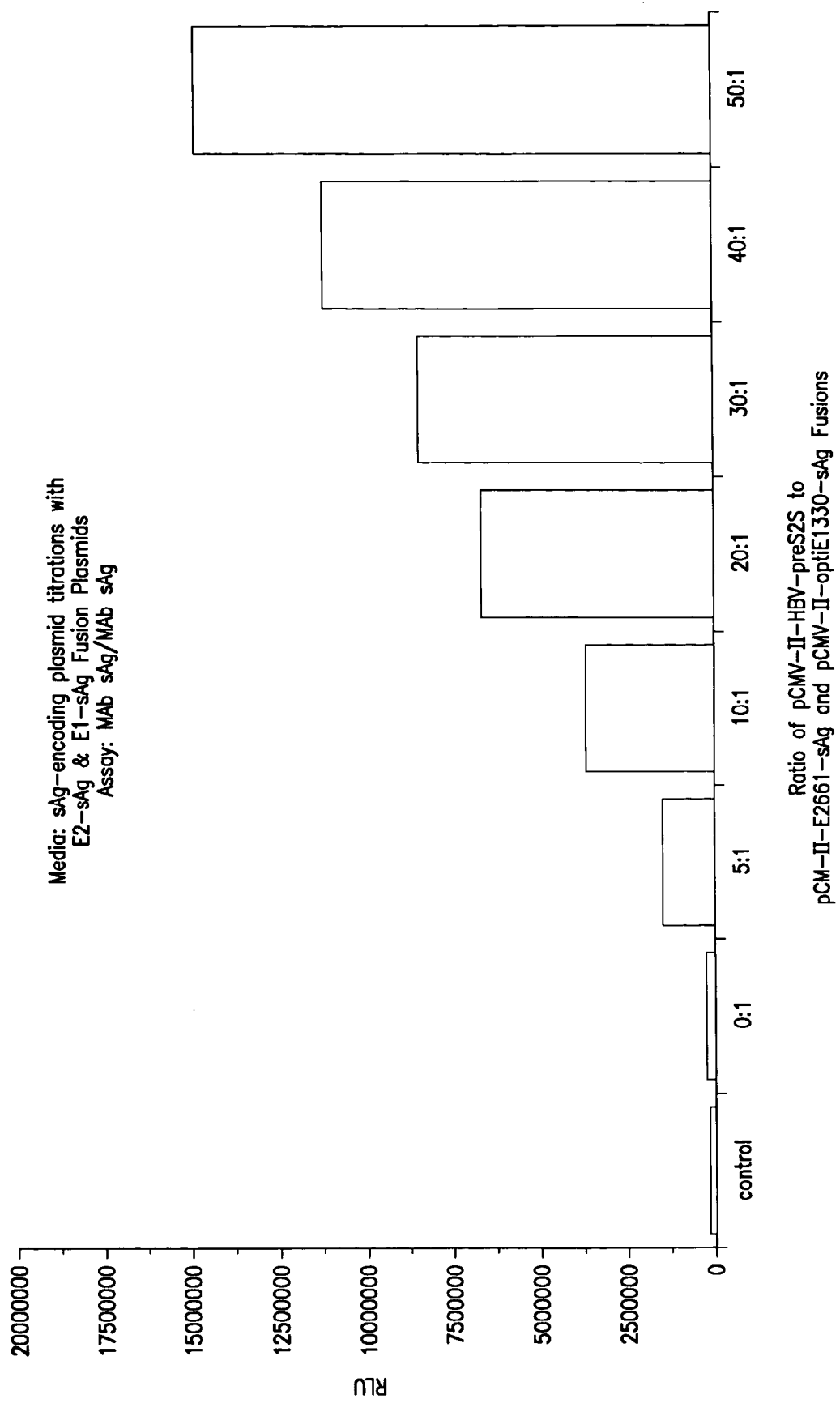

In order to characterize the virus-like particles, 1 mL of culture medium from each condition was loaded onto a 5-30% sucrose gradient. The samples were centrifuged 4 hrs at 40,000 rpm using a Beckman SW41 rotor. Eleven fractions were removed and assayed for E2 (FIG. 7A) or sAg (FIG. 7B) by the Magic Lite Assay. Both E2 and sAg were observed in highest amount in fraction 4, which is the same gradient position for the peak distribution of HBsAg-containing virus-like particles (FIG. 5).

Transfection Protocol

Cells were seeded in 6-well plates the day prior to transfection so as to achieve 50-60% confluency at the time of transfection. Opti-mem (100 μL) and LT-1 transfection reagent (12 μL) were added to a sterile polypropylene tube and incubated at room temperature for five minutes. Three μg of DNA was then added to the tube, which was incubated another five minutes at room temperature. During this incubation period, the cells were washed with Opti-mem (2 mLs per well). Two mLs Opti-mem were added to each well, followed by 100 μL of the Opti-mem/LT-1/DNA mixture. The cells were then incubated for four hours at 37° C., followed by aspiration and addition of culture medium (1.5 mL/well of DMEM+10% FBS). At 48 hours post transfection, the medium was harvested and the cell monolayers were solubilized using PBS containing 0.1% NP-40. Both the harvested medium and the solubilized cells were centrifuged to remove debris.

EXAMPLE 3

Expression of HBV/HCV Virus-Like Particles Containing Chimeric HBsAg-E1-330 Antigen in COS7 Cells Mixtures of pCMV-II-optiE1330-sAg (2.5 μg DNA) and various amounts of pCMV-II-pS2-sAg were prepared to provide ratios of sAg plasmid to E1-sAg plasmid of 0:1 (control), 1:1, 5:1, 10:1, and 20:1. Expression from pCMV-II-pS2-sAg resulted in a mixture of about 5-20% preS2-S-polypeptide, with the remainder being S-polypeptide. The total amount of DNA in each tube was normalized to 52.5 μg by the addition of pCMV-km-βgal. The mixtures were transfected into COS7 cells using the LT1 transfection reagent from Panvera. At 48 hours post-transfection, the media and soluble lysates were recovered and assayed by the Magic Lite Assay. Capture was with anti-sAg followed by detection with a conjugated anti-E1 MAb (eD5/C3) (FIG. 8A) or MAb sAg (FIG. 8B). Both E1 and sAg were increasingly secreted into the medium as the ratio of sAg:E2661-sAg was increased, with an optimum secretion at ratios in the range of 5:1 to 20:1.

In order to characterize the virus-like particles, 1 mL of culture medium from each condition was loaded onto a 5-30% sucrose gradient. The samples were centrifuged 4 hrs at 40,000 rpm using a Beckman SW41 rotor. Eleven fractions were removed and assayed for E1 (FIG. 9A) or sAg (FIG. 9B) by the Magic Lite Assay. Both E1 and sAg were observed in highest amount in fractions 4-6, which is similar to the gradient position for the peak distribution of HBsAg-containing virus-like particles (FIG. 5).

EXAMPLE 4

Expression of HBV/HCV Virus-Like Particles Containing Both HBsAg-E2-661 and HBsAg-E1-330 Chimeric Antigens in COS7 Cells A mixture of pCMVII opti 330 E1-sAg and pCMV-II-E2661-sAg (0.5 μg DNA of each plasmid) was combined with increasing amounts of pCMV-II-pS2-sAg. The total amount of DNA in each tube was normalized to 26 μg by the addition of pCMV-kM-βgal. The mixture was transfected into COS7 cells using the LT1 transfection reagent from PanVera. At 48 hours post-transfection, media and soluble lysates were recovered and assayed by the Magic Lite Assay, with capture by anti-sAg followed by detection with a conjugated anti-E2 or anti-E1 MAb (FIG. 10A) or a conjugated anti-sAg (FIG. 10B).

EXAMPLE 5

Use of HBV/HCV Virus-Like Particles to Generate an Immune Response

In order to test the ability of the subject HBV/HCV virus-like particles to generate an immune response in vivo, the following experiment was done. Four groups of 10 mice (Group 2 had 9 mice) were administered either DNA encoding HCV E2661 and pCMV-II, at a ratio of 5 times pCMV-II to E2661 (Group 1); pCMV-II-E2661-sAg (FIG. 4A) and pCMV-II, at a ratio of 5 times pCMV-II to pCMV-II-E2661-sAg (Group 2); pCMV-II-E2661-sAg and pCMV-II-pS2-sAg (FIG. 2A) at a ratio of 5 times pCMV-II-pS2-sAg to pCMV-II-E2661-sAg (Group 3); and pCMV-II and pCMV-II-pS2-sAg, at a ratio of 5 times pCMV-II-pS2-sAg to pCMV-II (Group 4).

All were immunized twice with 90 μg (45 μg/leg) per immunization, at day 0 and day 21, and blood was collected. Antibody titers were assessed by ELISA using a truncated E2 molecule, $E2_{715}$, which had been expressed in CHO cells, using the Magic Lite Assay described above. Results are shown in Table 1.

| Group # | Treatment | GM +/− SE |
|---|---|---|
| 1 | E2661 + 5x vector | 1300 +/− 85 |
| 2 | E2661-sAg + 5x vector | 1547 +/− 690 |
| 3 | E2661-sAg + 5x pS2sAg | 4175 +/− 603 |
| 4 | Vector + 5x pS2sAg | 0 |

A second experiment was run, again using 10 animals per group, except Group 5, which had 5 mice. The groups and results are shown in Table 2. Treatment protocol and antibody determination was as described above.

| Group # | Treatment | GM +/− SE |
|---|---|---|
| 1 | E2661 + 5x vector | 724 +/96 |
| 2 | E2661 + 5x pS2sAg | 222 +/90 |

-continued

| Group # | Treatment | GM +/− SE |
|---|---|---|
| 3 | E2661-sAg + 5x vector | 1018 +/305 |
| 4 | E2661-sAg + 5x pS2sAg | 1290 +/292 |
| 5 | mock | 0 |

As can be seen, titers to E2 in the $E2_{661}$-immunized mice were reduced in the presence of 5× sAg. This might have resulted from competition for docking to the endoplasmic reticulum. The E2 titers were higher when the E2 was fused to sAg. The addition of sAg in place of vector resulted in little change in titer. While this difference is small, comparison to the control with sAg is warranted. Since excess sAg caused a reduction in E2 titers in the unfused antigen, in the context of the fusion there was an apparent compensation. This presumably reflects the ability of sAg to promote secretion of the fusion.

Thus, chimeric HCV/HBV virus-like particles, as well as methods of making and using the same are disclosed. From the foregoing, it will be appreciated that, although specific embodiments of the invention have been described herein for purposes of illustration, various modifications may be made without deviating from the spirit and scope of the appended claims.

We claim:

1. A vector comprising the nucleotide sequence of SEQ ID NO:6, or a nucleotide sequence having at least about 90% sequence identity to the sequence of SEQ ID NO:6, wherein said vector is capable of expressing a fusion protein that comprises a native HCV epitope and elicits an immunological response against HCV.

2. An immunogenic composition comprising a nucleic acid molecule comprising the nucleotide sequence displayed in SEQ ID NO:6, or a nucleotide sequence having at least about 90% sequence identity to the sequence of SEQ ID NO:6, wherein said nucleic acid molecule is capable of expressing a fusion protein that comprises a native HCV epitope and elicits an immunological response against HCV.

3. A vector comprising a first nucleic acid sequence which encodes a HBsAg and a second nucleic acid sequence comprising the nucleotide sequence of SEQ ID NO:6, or a nucleotide sequence having at least about 90% sequence identity to the sequence of SEQ ID NO:6, wherein the first and the second nucleic acid sequences each comprise a substantially complete S domain, wherein said vector is capable of expressing a fusion protein that comprises a native HCV epitope and elicits an immunological response against HCV.

4. A cell line that expresses a virus-like particle comprising a first HBsAg and a chimeric antigen which comprises a second HBsAg, wherein the cell comprises the nucleotide sequence of SEQ ID NO: 6 or a sequence of at least about 90% identity thereto, and wherein the first and second HBsAg each comprise a substantially complete S domain, wherein said antigen comprises a native HCV epitope and is capable of eliciting an immunological response against HCV.

5. A method of producing the cell line of claim 4, the method comprising:
   transfecting a cell with pCMV-II-E2661-sAg (SEQ ID NO:6); and
   culturing the cell to produce a cell line that expresses the virus-like particles.

6. A method of producing a virus-like particle comprising the steps of:
   culturing a cell of the cell line of claim 4 in a culture medium and
   isolating the virus-like particle from the culture medium.

7. The method of claim 6, wherein the cell is a CHO cell or a COS cell.

* * * * *

UNITED STATES PATENT AND TRADEMARK OFFICE
CERTIFICATE OF CORRECTION

| | |
|---|---|
| PATENT NO. | : 7,439,058 B2 |
| APPLICATION NO. | : 10/715665 |
| DATED | : October 21, 2008 |
| INVENTOR(S) | : Mark Selby, Edward Glazer and Michael Houghton |

Page 1 of 1

It is certified that error appears in the above-identified patent and that said Letters Patent is hereby corrected as shown below:

Col. 58, line 50 Claim 7, should be deleted.

Signed and Sealed this

Fourth Day of August, 2009

JOHN DOLL
*Acting Director of the United States Patent and Trademark Office*

SEQUENCE LISTING

<160> NUMBER OF SEQ ID NOS: 7

<210> SEQ ID NO 1
<211> LENGTH: 4276
<212> TYPE: DNA
<213> ORGANISM: Artificial Sequence
<220> FEATURE:
<223> OTHER INFORMATION: Description of Artificial Sequence: plasmid pCMVII

<400> SEQUENCE: 1

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgaa gcttttttgca aaagcctagg cctccaaaaa agcctcctca ctacttctgg    240
aatagctcag aggccgaggc ggcctcggcc tctgcataaa taaaaaaaat tagtcagcca    300 tggggcgag aatgggcgga actgggcggg gagggaatta ttggctattg gccattgcat    360
acgttgtatc tatatcataa tatgtacatt tatattggct catgtccaat atgaccgcca    420
tgttgacatt gattattgac tagttattaa tagtaatcaa ttacggggtc attagttcat    480
agcccatata tggagttccg cgttacataa cttacggtaa atggcccgcc tggctgaccg    540
cccaacgacc cccgcccatt gacgtcaata atgacgtatg ttcccatagt aacgccaata    600
gggactttcc attgacgtca atgggtggag tatttacggt aaactgccca cttggcagta    660
catcaagtgt atcatatgcc aagtccgccc cctattgacg tcaatgacgg taaatggccc    720
gcctggcatt atgcccagta catgacctta cgggactttc ctacttggca gtacatctac    780
gtattagtca tcgctattac catggtgatg cggttttggc agtacaccaa tgggcgtgga    840
tagcggtttg actcacgggg atttccaagt ctccacccca ttgacgtcaa tgggagtttg    900
ttttggcacc aaaatcaacg ggactttcca aatgtcgta ataacccgc ccgttgacg      960 caaatgggcg taggcgtgt acggtgggag gtctatataa gcagagctcg tttagtgaac    1020
cgtcagatcg cctggagacg ccatccacgc tgttttgacc tccatagaag acaccgggac    1080
cgatccagcc tccgcggccg ggaacggtgc attggaacgc ggattcccg tgccaagagt    1140 gacgtaagta ccgcctatag actctatagg cacacccctt tggctcttat gcatgctata    1200
ctgttttggg cttggggcct atacaccccc gctccttatg ctataggtga tggtatagct    1260
tagcctatag gtgtgggtta ttgaccatta ttgaccactc ccctattggt gacgatactt    1320
tccattacta atccataaca tggctctttg ccacaactat ctctattggc tatatgccaa    1380
```

```
tactctgtcc ttcagagact gacacggact ctgtattttt acaggatggg gtccatttat    1440
tatttacaaa ttcacatata caacaacgcc gtcccccgtg cccgcagttt ttattaaaca    1500
tagcgtggga tctccgacat ctcgggtacg tgttccggac atgggctctt ctccggtagc    1560
ggcggagctt ccacatccga gccctggtcc catccgtcca gcggctcatg gtcgctcggc    1620
agctccttgc tcctaacagt ggaggccaga cttaggcaca gcacaatgcc caccaccacc    1680
agtgtgccgc acaaggccgt ggcggtaggg tatgtgtctg aaaatgagct cggagattgg    1740
gctcgcacct ggacgcagat ggaagactta aggcagcggc agaagaagat gcaggcagct    1800
gagttgttgt attctgataa gagtcagagg taactcccgt tgcggtgctg ttaacggtgg    1860
agggcagtgt agtctgagca gtactcgttg ctgccgcgcg cgccaccaga cataatagct    1920
gacagactaa cagactgttc cttccatgg gtcttttctg cagtcaccgt cgtcgaccta    1980
agaattcaga ctcgagcaag tctagaaagg cgcgccaaga tatcaaggat ccactacgcg    2040
ttagagctcg ctgatcagcc tcgactgtgc cttctagttg ccagccatct gttgtttgcc    2100 cctccccgt gccttccttg accctggaag gtgccactcc cactgtcctt tcctaataaa    2160
atgaggaaat tgcatcgcat tgtctgagta ggtgtcattc tattctgggg ggtggggtgg    2220
ggcaggacag caaggggag gattgggaag acaatagcag gcatgctggg gagctcttcc    2280
gcttcctcgc tcactgactc gctgcgctcg gtcgttcggc tgcggcgagc ggtatcagct    2340
cactcaaagg cggtaatacg gttatccaca gaatcagggg ataacgcagg aaagaacatg    2400
tgagcaaaag gccagcaaaa ggccaggaac cgtaaaaagg ccgcgttgct ggcgtttttc    2460
cataggctcc gcccccctga cgagcatcac aaaaatcgac gctcaagtca gaggtggcga    2520
aacccgacag gactataaag ataccaggcg tttccccctg gaagctccct cgtgcgctct    2580
cctgttccga ccctgccgct taccggatac ctgtccgcct ttctcccttc gggaagcgtg    2640
gcgctttctc aatgctcacg ctgtaggtat ctcagttcgg tgtaggtcgt tcgctccaag    2700
ctgggctgtg tgcacgaacc ccccgttcag cccgaccgct gcgccttatc cggtaactat    2760
cgtcttgagt ccaacccggt aagacacgac ttatcgccac tggcagcagc cactggtaac    2820
aggattagca gagcgaggta tgtaggcggt gctacagagt tcttgaagtg gtggcctaac    2880
tacggctaca ctagaaggac agtatttggt atctgcgctc tgctgaagcc agttaccttc    2940
ggaaaaagag ttggtagctc ttgatccggc aaacaaacca ccgctggtag cggtggtttt    3000
tttgtttgca agcagcagat tacgcgcaga aaaaaaggat ctcaagaaga tcctttgatc    3060
ttttctacgg ggtctgacgc tcagtggaac gaaaactcac gttaagggat tttggtcatg    3120
agattatcaa aaaggatctt cacctagatc cttttaaatt aaaaatgaag ttttaaatca    3180
atctaaagta tatatgagta aacttggtct gacagttacc aatgcttaat cagtgaggca    3240
cctatctcag cgatctgtct atttcgttca tccatagttg cctgactccc cgtcgtgtag    3300
ataactacga tacgggaggg cttaccatct ggccccagtg ctgcaatgat accgcgagac    3360
ccacgctcac cggctccaga tttatcagca ataaccagc cagccggaag ggccgagcgc    3420
agaagtggtc ctgcaacttt atccgcctcc atccagtcta ttaattgttg ccgggaagct    3480
agagtaagta gttcgccagt taatagtttg cgcaacgttg ttgccattgc tacaggcatc    3540
gtggtgtcac gctcgtcgtt tggtatggct tcattcagct ccggttccca acgatcaagg    3600
cgagttacat gatcccccat gttgtgcaaa aaagcggtta gctccttcgg tcctccgatc    3660
gttgtcagaa gtaagttggc cgcagtgtta tcactcatgg ttatggcagc actgcataat    3720
tctcttactg tcatgccatc cgtaagatgc ttttctgtga ctggtgagta ctcaaccaag    3780
```

| | |
|---|---|
| tcattctgag aatagtgtat gcggcgaccg agttgctctt gcccggcgtc aatacgggat | 3840 |
| aataccgcgc cacatagcag aactttaaaa gtgctcatca ttggaaaacg ttcttcgggg | 3900 |
| cgaaaactct caaggatctt accgctgttg agatccagtt cgatgtaacc cactcgtgca | 3960 |
| cccaactgat cttcagcatc ttttactttc accagcgttt ctgggtgagc aaaaacagga | 4020 |
| aggcaaaatg ccgcaaaaaa gggaataagg gcgacacgga aatgttgaat actcatactc | 4080 |
| ttcctttttc aatattattg aagcatttat cagggttatt gtctcatgag cggatacata | 4140 |
| tttgaatgta tttagaaaaa taaacaaata ggggttccgc gcacatttcc ccgaaaagtg | 4200 |
| ccacctgacg tctaagaaac cattattatc atgacattaa cctataaaaa taggcgtatc | 4260 |
| acgaggccct ttcgtc | 4276 |

<210> SEQ ID NO 2
<211> LENGTH: 5128
<212> TYPE: DNA
<213> ORGANISM: Artificial Sequence
<220> FEATURE:
<223> OTHER INFORMATION: Description of Artificial Sequence: plasmid
      pCMVII-pS2-SAg
<220> FEATURE:
<221> NAME/KEY: CDS
<222> LOCATION: (1988)..(2830)

<400> SEQUENCE: 2

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgaa gcttttgca aaagcctagg cctccaaaaa agcctcctca ctacttctgg | 240 |
| aatagctcag aggccgaggc ggcctcggcc tctgcataaa taaaaaaaat tagtcagcca | 300 |
| tggggcggag aatgggcgga actgggcggg agggaatta ttggctattg gccattgcat | 360 |
| acgttgtatc tatatcataa tatgtacatt tatattggct catgtccaat atgaccgcca | 420 |
| tgttgacatt gattattgac tagttattaa tagtaatcaa ttacggggtc attagttcat | 480 |
| agcccatata tggagttccg cgttacataa cttacggtaa atggcccgcc tggctgaccg | 540 |
| cccaacgacc cccgcccatt gacgtcaata atgacgtatg ttcccatagt aacgccaata | 600 |
| gggactttcc attgacgtca atgggtggag tatttacggt aaactgccca cttggcagta | 660 |
| catcaagtgt atcatatgcc aagtccgccc cctattgacg tcaatgacgg taaatggccc | 720 |
| gcctggcatt atgcccagta catgacctta cgggactttc ctacttggca gtacatctac | 780 |
| gtattagtca tcgctattac catggtgatg cggttttggc agtacaccaa tgggcgtgga | 840 |
| tagcggtttg actcacgggg atttccaagt ctccacccca ttgacgtcaa tgggagtttg | 900 |
| ttttggcacc aaaatcaacg ggactttcca aatgtcgta ataaccccgc ccgttgacg | 960 |
| caaatgggcg gtaggcgtgt acggtggag gtctatataa gcagagctcg tttagtgaac | 1020 |
| cgtcagatcg cctggagacg ccatccacgc tgttttgacc tccatagaag acaccgggac | 1080 |
| cgatccagcc tccgcggccg ggaacggtgc attggaacgc ggattcccg tgccaagagt | 1140 |
| gacgtaagta ccgcctatag actctatagg cacaccctt tggctcttat gcatgctata | 1200 |
| ctgtttttgg cttggggcct atacaccccc gctccttatg ctataggtga tggtatagct | 1260 |
| tagcctatag gtgtgggtta ttgaccatta ttgaccactc ccctattggt gacgatactt | 1320 |
| tccattacta atccataaca tggctctttg ccacaactat ctctattggc tatatgccaa | 1380 |

-continued

```
tactctgtcc ttcagagact gacacggact ctgtattttt acaggatggg gtccatttat    1440
tatttacaaa ttcacatata caacaacgcc gtcccccgtg cccgcagttt ttattaaaca    1500
tagcgtggga tctccgacat ctcgggtacg tgttccggac atgggctctt ctccggtagc    1560
ggcggagctt ccacatccga gccctggtcc catccgtcca gcggctcatg gtcgctcggc    1620
agctccttgc tcctaacagt ggaggccaga cttaggcaca gcacaatgcc caccaccacc    1680
agtgtgccgc acaaggccgt ggcggtaggg tatgtgtctg aaaatgagct cggagattgg    1740
gctcgcacct ggacgcagat ggaagactta aggcagcggc agaagaagat gcaggcagct    1800
gagttgttgt attctgataa gagtcagagg taactcccgt tgcggtgctg ttaacggtgg    1860
agggcagtgt agtctgagca gtactcgttg ctgccgcgcg cgccaccaga cataatagct    1920
gacagactaa cagactgttc ctttccatgg gtcttttctg cagtcaccgt cgtcgaccta    1980
```

| | | | | | | | | | | | | | | | |
|---|---|---|---|---|---|---|---|---|---|---|---|---|---|---|---|
| agaattc | atg | cag | tgg | aac | tcc | act | gcc | ttc | cac | caa | act | ctg | cag | gat | 2029 |
| | Met | Gln | Trp | Asn | Ser | Thr | Ala | Phe | His | Gln | Thr | Leu | Gln | Asp | |
| | 1 | | | 5 | | | | | 10 | | | | | | |

| ccc | aga | gtc | agg | ggt | ctg | tat | ctt | cct | gct | ggt | ggc | tcc | agt | tca | gga | 2077 |
|---|---|---|---|---|---|---|---|---|---|---|---|---|---|---|---|---|
| Pro | Arg | Val | Arg | Gly | Leu | Tyr | Leu | Pro | Ala | Gly | Gly | Ser | Ser | Ser | Gly | |
| 15 | | | | 20 | | | | | 25 | | | | | | 30 | |

| aca | gta | aac | cct | gct | ccg | aat | att | gcc | tct | cac | atc | tcg | tca | atc | tcc | 2125 |
|---|---|---|---|---|---|---|---|---|---|---|---|---|---|---|---|---|
| Thr | Val | Asn | Pro | Ala | Pro | Asn | Ile | Ala | Ser | His | Ile | Ser | Ser | Ile | Ser | |
| | | | | 35 | | | | | 40 | | | | | 45 | | |

| gcg | agg | act | ggg | gac | cct | gtg | acg | aac | atg | gag | aac | atc | aca | tca | gga | 2173 |
|---|---|---|---|---|---|---|---|---|---|---|---|---|---|---|---|---|
| Ala | Arg | Thr | Gly | Asp | Pro | Val | Thr | Asn | Met | Glu | Asn | Ile | Thr | Ser | Gly | |
| | | | 50 | | | | | 55 | | | | | 60 | | | |

| ttc | cta | gga | ccc | ctg | ctc | gtg | tta | cag | gcg | ggg | ttt | ttc | ttg | ttg | aca | 2221 |
|---|---|---|---|---|---|---|---|---|---|---|---|---|---|---|---|---|
| Phe | Leu | Gly | Pro | Leu | Leu | Val | Leu | Gln | Ala | Gly | Phe | Phe | Leu | Leu | Thr | |
| 65 | | | | | 70 | | | | | 75 | | | | | | |

| aga | atc | ctc | aca | ata | ccg | cag | agt | cta | gac | tcg | tgg | tgg | act | tct | ctc | 2269 |
|---|---|---|---|---|---|---|---|---|---|---|---|---|---|---|---|---|
| Arg | Ile | Leu | Thr | Ile | Pro | Gln | Ser | Leu | Asp | Ser | Trp | Trp | Thr | Ser | Leu | |
| 80 | | | | | 85 | | | | | 90 | | | | | | |

| aat | ttt | cta | ggg | gga | tct | ccc | gtg | tgt | ctt | ggc | caa | aat | tcg | cag | tcc | 2317 |
|---|---|---|---|---|---|---|---|---|---|---|---|---|---|---|---|---|
| Asn | Phe | Leu | Gly | Gly | Ser | Pro | Val | Cys | Leu | Gly | Gln | Asn | Ser | Gln | Ser | |
| 95 | | | | 100 | | | | | 105 | | | | | 110 | | |

| cca | acc | tcc | aat | cac | tca | cca | acc | tcc | tgt | cct | cca | att | tgt | cct | ggt | 2365 |
|---|---|---|---|---|---|---|---|---|---|---|---|---|---|---|---|---|
| Pro | Thr | Ser | Asn | His | Ser | Pro | Thr | Ser | Cys | Pro | Pro | Ile | Cys | Pro | Gly | |
| | | | | 115 | | | | | 120 | | | | | 125 | | |

| tat | cgc | tgg | atg | tgt | ctg | cgg | cgt | ttt | atc | ata | ttc | ctc | ttc | atc | ctg | 2413 |
|---|---|---|---|---|---|---|---|---|---|---|---|---|---|---|---|---|
| Tyr | Arg | Trp | Met | Cys | Leu | Arg | Arg | Phe | Ile | Ile | Phe | Leu | Phe | Ile | Leu | |
| | | | 130 | | | | | 135 | | | | | 140 | | | |

| ctg | cta | tgc | ctc | atc | ttc | tta | ttg | gtt | ctt | ctg | gat | tat | caa | ggt | atg | 2461 |
|---|---|---|---|---|---|---|---|---|---|---|---|---|---|---|---|---|
| Leu | Leu | Cys | Leu | Ile | Phe | Leu | Leu | Val | Leu | Leu | Asp | Tyr | Gln | Gly | Met | |
| | | 145 | | | | | 150 | | | | | 155 | | | | |

| ttg | ccc | gtt | tgt | cct | cta | att | cca | gga | tca | aca | aca | acc | agt | acg | gga | 2509 |
|---|---|---|---|---|---|---|---|---|---|---|---|---|---|---|---|---|
| Leu | Pro | Val | Cys | Pro | Leu | Ile | Pro | Gly | Ser | Thr | Thr | Thr | Ser | Thr | Gly | |
| | 160 | | | | | 165 | | | | | 170 | | | | | |

| cca | tgc | aaa | acc | tgc | acg | act | cct | gct | caa | ggc | aac | tct | atg | ttt | ccc | 2557 |
|---|---|---|---|---|---|---|---|---|---|---|---|---|---|---|---|---|
| Pro | Cys | Lys | Thr | Cys | Thr | Thr | Pro | Ala | Gln | Gly | Asn | Ser | Met | Phe | Pro | |
| 175 | | | | 180 | | | | | 185 | | | | | 190 | | |

| tca | tgt | tgc | tgt | aca | aaa | cct | acg | gat | gga | aat | tgc | acc | tgt | att | ccc | 2605 |
|---|---|---|---|---|---|---|---|---|---|---|---|---|---|---|---|---|
| Ser | Cys | Cys | Cys | Thr | Lys | Pro | Thr | Asp | Gly | Asn | Cys | Thr | Cys | Ile | Pro | |
| | | | 195 | | | | | 200 | | | | | 205 | | | |

| atc | cca | tcg | tcc | tgg | gct | ttc | gca | aaa | tac | cta | tgg | gag | tgg | gcc | tca | 2653 |
|---|---|---|---|---|---|---|---|---|---|---|---|---|---|---|---|---|
| Ile | Pro | Ser | Ser | Trp | Ala | Phe | Ala | Lys | Tyr | Leu | Trp | Glu | Trp | Ala | Ser | |
| | | 210 | | | | | 215 | | | | | 220 | | | | |

| gtc | cgt | ttc | tct | tgg | ctc | agt | tta | cta | gtg | cca | ttt | gtt | cag | tgg | ttc | 2701 |
|---|---|---|---|---|---|---|---|---|---|---|---|---|---|---|---|---|
| Val | Arg | Phe | Ser | Trp | Leu | Ser | Leu | Leu | Val | Pro | Phe | Val | Gln | Trp | Phe | |
| | 225 | | | | | 230 | | | | | 235 | | | | | |

| | | |
|---|---|---|
| gta ggg ctt tcc ccc act gtt tgg ctt tca gct ata tgg atg atg tgg | | 2749 |
| Val Gly Leu Ser Pro Thr Val Trp Leu Ser Ala Ile Trp Met Met Trp | | |
| 240 245 250 | | |
| tat tgg ggg cca agt ctg tac agc atc gtg agt ccc ttt ata ccg ctg | | 2797 |
| Tyr Trp Gly Pro Ser Leu Tyr Ser Ile Val Ser Pro Phe Ile Pro Leu | | |
| 255 260 265 270 | | |
| tta cca att ttc ttt tgt ctc tgg gta tac att taagaattca gactcgagca | | 2850 |
| Leu Pro Ile Phe Phe Cys Leu Trp Val Tyr Ile | | |
| 275 280 | | |
| agtctagaaa ggcgcgccaa gatatcaagg atccactacg cgttagagct cgctgatcag | | 2910 |
| cctcgactgt gccttctagt tgccagccat ctgttgtttg cccctccccc gtgccttcct | | 2970 |
| tgaccctgga aggtgccact cccactgtcc tttcctaata aaatgaggaa attgcatcgc | | 3030 |
| attgtctgag taggtgtcat tctattctgg gggtggggt gggcaggac agcaagggg | | 3090 |
| aggattggga agacaatagc aggcatgctg gggagctctt ccgcttcctc gctcactgac | | 3150 |
| tcgctgcgct cggtcgttcg gctgcggcga gcggtatcag ctcactcaaa ggcggtaata | | 3210 |
| cggttatcca cagaatcagg ggataacgca ggaaagaaca tgtgagcaaa aggccagcaa | | 3270 |
| aaggccagga accgtaaaaa ggccgcgttg ctggcgtttt tccataggct ccgcccccct | | 3330 |
| gacgagcatc acaaaaatcg acgctcaagt cagaggtggc gaaacccgac aggactataa | | 3390 |
| agataccagg cgtttccccc tggaagctcc ctcgtgcgct ctcctgttcc gaccctgccg | | 3450 |
| cttaccggat acctgtccgc ctttctccct tcgggaagcg tggcgctttc tcaatgctca | | 3510 |
| cgctgtaggt atctcagttc ggtgtaggtc gttcgctcca agctgggctg tgtgcacgaa | | 3570 |
| ccccccgttc agcccgaccg ctgcgcctta tccgtaact atcgtcttga gtccaacccg | | 3630 |
| gtaagacacg acttatcgcc actggcagca gccactggta acaggattag cagagcgagg | | 3690 |
| tatgtaggcg gtgctacaga gttcttgaag tggtggccta actacggcta cactagaagg | | 3750 |
| acagtatttg gtatctgcgc tctgctgaag ccagttacct tcggaaaaag agttggtagc | | 3810 |
| tcttgatccg gcaaacaaac caccgctggt agcggtggtt ttttgtttg caagcagcag | | 3870 |
| attacgcgca gaaaaaaagg atctcaagaa gatcctttga tcttttctac ggggtctgac | | 3930 |
| gctcagtgga acgaaaactc acgttaaggg attttggtca tgagattatc aaaaaggatc | | 3990 |
| ttcacctaga tccttttaaa ttaaaaatga agttttaaat caatctaaag tatatatgag | | 4050 |
| taaacttggt ctgacagtta ccaatgctta atcagtgagg cacctatctc agcgatctgt | | 4110 |
| ctatttcgtt catccatagt tgcctgactc ccgtcgtgt agataactac gatacgggag | | 4170 |
| ggcttaccat ctggccccag tgctgcaatg ataccgcgag acccacgctc accggctcca | | 4230 |
| gatttatcag caataaacca gccagccgga agggccgagc gcagaagtgg tcctgcaact | | 4290 |
| ttatccgcct ccatccagtc tattaattgt tgccgggaag ctagagtaag tagttcgcca | | 4350 |
| gttaatagtt tgcgcaacgt tgttgccatt gctacaggca tcgtggtgtc acgctcgtcg | | 4410 |
| tttggtatgg cttcattcag ctccggttcc caacgatcaa ggcgagttac atgatccccc | | 4470 |
| atgttgtgca aaaaagcggt tagctccttc ggtcctccga tcgttgtcag aagtaagttg | | 4530 |
| gccgcagtgt tatcactcat ggttatggca gcactgcata attctcttac tgtcatgcca | | 4590 |
| tccgtaagat gcttttctgt gactggtgag tactcaacca agtcattctg agaatagtgt | | 4650 |
| atgcggcgac cgagttgctc ttgcccggcg tcaatacggg ataataccgc gccacatagc | | 4710 |
| agaactttaa aagtgctcat cattggaaaa cgttcttcgg ggcgaaaact ctcaaggatc | | 4770 |
| ttaccgctgt tgagatccag ttcgatgtaa cccactcgtg cacccaactg atcttcagca | | 4830 |

-continued

```
tcttttactt tcaccagcgt ttctgggtga gcaaaaacag gaaggcaaaa tgccgcaaaa    4890
aagggaataa gggcgacacg gaaatgttga atactcatac tcttcctttt tcaatattat    4950
tgaagcattt atcagggtta ttgtctcatg agcggataca tatttgaatg tatttagaaa    5010
aataaacaaa tagggttcc gcgcacattt ccccgaaaag tgccacctga cgtctaagaa    5070
accattatta tcatgacatt aacctataaa aataggcgta tcacgaggcc ctttcgtc     5128
```

<210> SEQ ID NO 3
<211> LENGTH: 281
<212> TYPE: PRT
<213> ORGANISM: Artificial Sequence
<220> FEATURE:
<223> OTHER INFORMATION: Description of Artificial Sequence: plasmid pCMVII-pS2-SAg

<400> SEQUENCE: 3

```
Met Gln Trp Asn Ser Thr Ala Phe His Gln Thr Leu Gln Asp Pro Arg
 1               5                  10                  15

Val Arg Gly Leu Tyr Leu Pro Ala Gly Gly Ser Ser Ser Gly Thr Val
            20                  25                  30

Asn Pro Ala Pro Asn Ile Ala Ser His Ile Ser Ser Ile Ser Ala Arg
        35                  40                  45

Thr Gly Asp Pro Val Thr Asn Met Glu Asn Ile Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Ser Pro Val Cys Leu Gly Gln Asn Ser Gln Ser Pro Thr
            100                 105                 110

Ser Asn His Ser Pro Thr Ser Cys Pro Pro Ile Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Thr Thr Thr Ser Thr Gly Pro Cys
                165                 170                 175

Lys Thr Cys Thr Thr Pro Ala Gln Gly Asn Ser Met Phe Pro Ser Cys
            180                 185                 190

Cys Cys Thr Lys Pro Thr Asp Gly Asn Cys Thr Cys Ile Pro Ile Pro
        195                 200                 205

Ser Ser Trp Ala Phe Ala Lys Tyr Leu Trp Glu Trp Ala Ser Val Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Ala Ile Trp Met Met Trp Tyr Trp
                245                 250                 255

Gly Pro Ser Leu Tyr Ser Ile Val Ser Pro Phe Ile Pro Leu Leu Pro
            260                 265                 270

Ile Phe Phe Cys Leu Trp Val Tyr Ile
        275                 280
```

<210> SEQ ID NO 4
<211> LENGTH: 5459
<212> TYPE: DNA

<213> ORGANISM: Artificial Sequence
<220> FEATURE:
<223> OTHER INFORMATION: Description of Artificial Sequence: pCMVII opti
      330 E1/SAg
<220> FEATURE:
<221> NAME/KEY: CDS
<222> LOCATION: (1992)..(3161)

<400> SEQUENCE: 4

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgaa gcttttgca aaagcctagg cctccaaaaa agcctcctca ctacttctgg      240
aatagctcag aggccgaggc ggcctcggcc tctgcataaa taaaaaaaat tagtcagcca     300
tggggcggag aatgggcgga actgggcggg agggaatta ttggctattg gccattgcat      360
acgttgtatc tatatcataa tatgtacatt tatattggct catgtccaat atgaccgcca     420
tgttgacatt gattattgac tagttattaa tagtaatcaa ttacggggtc attagttcat     480
agcccatata tggagttccg cgttacataa cttacggtaa atggcccgcc tggctgaccg     540
cccaacgacc cccgcccatt gacgtcaata atgacgtatg ttcccatagt aacgccaata     600
gggactttcc attgacgtca atgggtggag tatttacggt aaactgccca cttggcagta     660
catcaagtgt atcatatgcc aagtccgccc cctattgacg tcaatgacgg taaatggccc     720
gcctggcatt atgcccagta catgacctta cgggactttc ctacttggca gtacatctac     780
gtattagtca tcgctattac catggtgatg cggttttggc agtacaccaa tgggcgtgga     840
tagcggtttg actcacgggg atttccaagt ctccacccca ttgacgtcaa tgggagtttg     900
ttttggcacc aaaatcaacg ggactttcca aatgtcgta ataaccccgc ccgttgacg      960 caaatgggcg gtaggcgtgt acggtggag gtctatataa gcagagctcg tttagtgaac    1020
cgtcagatcg cctggagacg ccatccacgc tgttttgacc tccatagaag acaccgggac    1080
cgatccagcc tccgcggccg gaacggtgc attggaacgc ggattccccg tgccaagagt     1140
gacgtaagta ccgcctatag actctatagg cacacccctt ggctcttat gcatgctata    1200 ctgtttttgg cttggggcct atacaccccc gctccttatg ctataggtga tggtatagct    1260
tagcctatag gtgtgggtta ttgaccatta ttgaccactc ccctattggt gacgatactt    1320
tccattacta atccataaca tggctctttg ccacaactat ctctattggc tatatgccaa    1380
tactctgtcc ttcagagact gacacggact ctgtattttt acaggatggg gtccatttat    1440
tatttacaaa ttcacatata caacaacgcc gtccccgtg cccgcagttt ttattaaaca     1500
tagcgtggga tctccgacat tcgggtacg tgttccggac atgggctctt ctccggtagc    1560
ggcggagctt ccacatccga gccctggtcc catccgtcca gcggctcatg gtcgctcggc    1620
agctccttgc tcctaacagt ggaggccaga cttaggcaca gcacaatgcc caccaccacc    1680
agtgtgccgc acaaggccgt ggcggtaggg tatgtgtctg aaaatgagct cggagattgg    1740
gctcgcacct ggacgcagat ggaagactta aggcagcggc agaagaagat gcaggcagct    1800
gagttgttgt attctgataa gagtcagagg taactcccgt gcggtgctg ttaacggtgg     1860 agggcagtgt agtctgagca gtactcgttg ctgccgcgcg cgccaccaga cataatagct    1920
gacagactaa cagactgttc ctttccatgg gtcttttctg cagtcaccgt cgtcgacgaa    1980
```

```
ttcaagcaat c atg gat gca atg aag aga ggg ctc tgc tgt gtg ctg ctg    2030
              Met Asp Ala Met Lys Arg Gly Leu Cys Cys Val Leu Leu
               1               5                  10
```

```
ctg tgt gga gca gtc ttc gtt tcg ccc agc gct agc tac cag gtg cgc        2078
Leu Cys Gly Ala Val Phe Val Ser Pro Ser Ala Ser Tyr Gln Val Arg
    15                  20                  25 aac agc acc ggc ctg tac cac gtg acc aac gac tgc ccc aac agc agc        2126
Asn Ser Thr Gly Leu Tyr His Val Thr Asn Asp Cys Pro Asn Ser Ser
 30                  35                  40                  45 atc gtg tac gag gcc gcc gac gcc atc ctg cac acc ccc ggc tgc gtg        2174
Ile Val Tyr Glu Ala Ala Asp Ala Ile Leu His Thr Pro Gly Cys Val
                     50                  55                  60 ccc tgc gtg cgc gag ggc aac gcc agc cgc tgc tgg gtg gcc atg acc        2222
Pro Cys Val Arg Glu Gly Asn Ala Ser Arg Cys Trp Val Ala Met Thr
                 65                  70                  75 ccc acc gtg gcc acc cgc gac ggc aag ctg ccc gcc acc cag ctg cgc        2270
Pro Thr Val Ala Thr Arg Asp Gly Lys Leu Pro Ala Thr Gln Leu Arg
             80                  85                  90 cgc cac atc gac ctg ctg gtg ggc agc gcc acc ctg tgc agc gcc ctg        2318
Arg His Ile Asp Leu Leu Val Gly Ser Ala Thr Leu Cys Ser Ala Leu
         95                  100                 105 tac gtg ggc gac ctg tgc ggc agc gtg ttc ctg gtg ggc cag ctg ttc        2366
Tyr Val Gly Asp Leu Cys Gly Ser Val Phe Leu Val Gly Gln Leu Phe
110                 115                 120                 125 acc ttc agc ccc cgc cgc cac tgg acc acc cag ggc tgc aac tgc agc        2414
Thr Phe Ser Pro Arg Arg His Trp Thr Thr Gln Gly Cys Asn Cys Ser
                130                 135                 140 atc tac ccc ggc cac atc acc ggc cac cgc atg gcc tgg gac atg atg        2462
Ile Tyr Pro Gly His Ile Thr Gly His Arg Met Ala Trp Asp Met Met
            145                 150                 155 atg aac tgg agc ccc acc acc atg gag aac atc aca tca gga ttc cta        2510
Met Asn Trp Ser Pro Thr Thr Met Glu Asn Ile Thr Ser Gly Phe Leu
        160                 165                 170 gga ccc ctg ctc gtg tta cag gcg ggg ttt ttc ttg ttg aca aga atc        2558
Gly Pro Leu Leu Val Leu Gln Ala Gly Phe Phe Leu Leu Thr Arg Ile
    175                 180                 185 ctc aca ata ccg cag agt cta gac tcg tgg tgg act tct ctc aat ttt        2606
Leu Thr Ile Pro Gln Ser Leu Asp Ser Trp Trp Thr Ser Leu Asn Phe
190                 195                 200                 205 cta ggg gga tct ccc gtg tgt ctt ggc caa aat tcg cag tcc cca acc        2654
Leu Gly Gly Ser Pro Val Cys Leu Gly Gln Asn Ser Gln Ser Pro Thr
                210                 215                 220 tcc aat cac tca cca acc tcc tgt cct cca att tgt cct ggt tat cgc        2702
Ser Asn His Ser Pro Thr Ser Cys Pro Pro Ile Cys Pro Gly Tyr Arg
            225                 230                 235 tgg atg tgt ctg cgg cgt ttt atc ata ttc ctc ttc atc ctg ctg cta        2750
Trp Met Cys Leu Arg Arg Phe Ile Ile Phe Leu Phe Ile Leu Leu Leu
        240                 245                 250 tgc ctc atc ttc tta ttg gtt ctt ctg gat tat caa ggt atg ttg ccc        2798
Cys Leu Ile Phe Leu Leu Val Leu Leu Asp Tyr Gln Gly Met Leu Pro
    255                 260                 265 gtt tgt cct cta att cca gga tca aca aca acc agt acg gga cca tgc        2846
Val Cys Pro Leu Ile Pro Gly Ser Thr Thr Thr Ser Thr Gly Pro Cys
270                 275                 280                 285 aaa acc tgc acg act cct gct caa ggc aac tct atg ttt ccc tca tgt        2894
Lys Thr Cys Thr Thr Pro Ala Gln Gly Asn Ser Met Phe Pro Ser Cys
                290                 295                 300 tgc tgt aca aaa cct acg gat gga aat tgc acc tgt att ccc atc cca        2942
Cys Cys Thr Lys Pro Thr Asp Gly Asn Cys Thr Cys Ile Pro Ile Pro
            305                 310                 315 tcg tcc tgg gct ttc gca aaa tac cta tgg gag tgg gcc tca gtc cgt        2990
Ser Ser Trp Ala Phe Ala Lys Tyr Leu Trp Glu Trp Ala Ser Val Arg
```

```
                320                 325                 330
ttc tct tgg ctc agt tta cta gtg cca ttt gtt cag tgg ttc gta ggg     3038
Phe Ser Trp Leu Ser Leu Leu Val Pro Phe Val Gln Trp Phe Val Gly
        335                 340                 345 ctt tcc ccc act gtt tgg ctt tca gct ata tgg atg atg tgg tat tgg     3086
Leu Ser Pro Thr Val Trp Leu Ser Ala Ile Trp Met Met Trp Tyr Trp
350                 355                 360                 365 ggg cca agt ctg tac agc atc gtg agt ccc ttt ata ccg ctg tta cca     3134
Gly Pro Ser Leu Tyr Ser Ile Val Ser Pro Phe Ile Pro Leu Leu Pro
                370                 375                 380 att ttc ttt tgt ctc tgg gta tac att taagaattca gactcgagca           3181
Ile Phe Phe Cys Leu Trp Val Tyr Ile
                385                 390 agtctagaaa ggcgcgccaa gatatcaagg atccactacg cgttagagct cgctgatcag   3241
cctcgactgt gccttctagt tgccagccat ctgttgtttg cccctccccc gtgccttcct   3301
tgaccctgga aggtgccact cccactgtcc tttcctaata aaatgaggaa attgcatcgc   3361
attgtctgag taggtgtcat tctattctgg ggggtggggt ggggcaggac agcaagggg    3421
aggattggga agacaatagc aggcatgctg gggagctctt ccgcttcctc gctcactgac   3481
tcgctgcgct cggtcgttcg gctgcggcga gcggtatcag ctcactcaaa ggcggtaata   3541
cggttatcca cagaatcagg ggataacgca ggaaagaaca tgtgagcaaa aggccagcaa   3601
aaggccagga accgtaaaaa ggccgcgttg ctggcgtttt tccataggct ccgcccccct   3661
gacgagcatc acaaaaatcg acgctcaagt cagaggtggc gaaacccgac aggactataa   3721
agataccagg cgtttccccc tggaagctcc ctcgtgcgct ctcctgttcc gaccctgccg   3781
cttaccggat acctgtccgc ctttctccct tcgggaagcg tggcgctttc tcaatgctca   3841
cgctgtaggt atctcagttc ggtgtaggtc gttcgctcca agctgggctg tgtgcacgaa   3901
ccccccgttc agcccgaccg ctgcgcctta tccggtaact atcgtcttga gtccaacccg   3961
gtaagacacg acttatcgcc actggcagca gccactggta acaggattag cagagcgagg   4021
tatgtaggcg gtgctacaga gttcttgaag tggtggccta actacggcta cactagaagg   4081
acagtatttg gtatctgcgc tctgctgaag ccagttacct tcggaaaaag agttggtagc   4141
tcttgatccg gcaaacaaac caccgctggt agcggtggtt tttttgtttg caagcagcag   4201
attacgcgca gaaaaaaagg atctcaagaa gatcctttga tcttttctac ggggtctgac   4261
gctcagtgga acgaaaactc acgttaaggg attttggtca tgagattatc aaaaaggatc   4321
ttcacctaga tccttttaaa ttaaaaatga agttttaaat caatctaaag tatatatgag   4381
taaacttggt ctgacagtta ccaatgctta atcagtgagg cacctatctc agcgatctgt   4441
ctatttcgtt catccatagt tgcctgactc cccgtcgtgt agataactac gatacgggag   4501
ggcttaccat ctggccccag tgctgcaatg ataccgcgag acccacgctc accggctcca   4561
gatttatcag caataaacca gccagccgga agggccgagc gcagaagtgg tcctgcaact   4621
ttatccgcct ccatccagtc tattaattgt tgccgggaag ctagagtaag tagttcgcca   4681
gttaatagtt tgcgcaacgt tgttgccatt gctacaggca tcgtggtgtc acgctcgtcg   4741
tttggtatgg cttcattcag ctccggttcc caacgatcaa ggcgagttac atgatccccc   4801
atgttgtgca aaaaagcggt tagctccttc ggtcctccga tcgttgtcag aagtaagttg   4861
gccgcagtgt tatcactcat ggttatggca gcactgcata attctcttac tgtcatgcca   4921
tccgtaagat gcttttctgt gactggtgag tactcaacca agtcattctg agaatagtgt   4981
atgcggcgac cgagttgctc ttgcccggcg tcaatacggg ataataccgc gccacatagc   5041
```

-continued

```
agaactttaa aagtgctcat cattggaaaa cgttcttcgg ggcgaaaact ctcaaggatc    5101
ttaccgctgt tgagatccag ttcgatgtaa cccactcgtg cacccaactg atcttcagca    5161
tcttttactt tcaccagcgt ttctgggtga gcaaaaacag gaaggcaaaa tgccgcaaaa    5221
aagggaataa gggcgacacg gaaatgttga atactcatac tcttcctttt tcaatattat    5281
tgaagcattt atcagggtta ttgtctcatg agcggataca tatttgaatg tatttagaaa    5341
aataaacaaa taggggttcc gcgcacattt ccccgaaaag tgccacctga cgtctaagaa    5401
accattatta tcatgacatt aacctataaa aataggcgta tcacgaggcc ctttcgtc     5459
```

<210> SEQ ID NO 5
<211> LENGTH: 390
<212> TYPE: PRT
<213> ORGANISM: Artificial Sequence
<220> FEATURE:
<223> OTHER INFORMATION: Description of Artificial Sequence: pCMVII opti 330 E1/SAg

<400> SEQUENCE: 5

```
Met Asp Ala Met Lys Arg Gly Leu Cys Cys Val Leu Leu Leu Cys Gly
  1               5                  10                  15

Ala Val Phe Val Ser Pro Ser Ala Ser Tyr Gln Val Arg Asn Ser Thr
             20                  25                  30

Gly Leu Tyr His Val Thr Asn Asp Cys Pro Asn Ser Ser Ile Val Tyr
         35                  40                  45

Glu Ala Ala Asp Ala Ile Leu His Thr Pro Gly Cys Val Pro Cys Val
     50                  55                  60

Arg Glu Gly Asn Ala Ser Arg Cys Trp Val Ala Met Thr Pro Thr Val
 65                  70                  75                  80

Ala Thr Arg Asp Gly Lys Leu Pro Ala Thr Gln Leu Arg Arg His Ile
                 85                  90                  95

Asp Leu Leu Val Gly Ser Ala Thr Leu Cys Ser Ala Leu Tyr Val Gly
            100                 105                 110

Asp Leu Cys Gly Ser Val Phe Leu Val Gly Gln Leu Phe Thr Phe Ser
        115                 120                 125

Pro Arg Arg His Trp Thr Thr Gln Gly Cys Asn Cys Ser Ile Tyr Pro
    130                 135                 140

Gly His Ile Thr Gly His Arg Met Ala Trp Asp Met Met Met Asn Trp
145                 150                 155                 160

Ser Pro Thr Thr Met Glu Asn Ile Thr Ser Gly Phe Leu Gly Pro Leu
                165                 170                 175

Leu Val Leu Gln Ala Gly Phe Phe Leu Leu Thr Arg Ile Leu Thr Ile
            180                 185                 190

Pro Gln Ser Leu Asp Ser Trp Trp Thr Ser Leu Asn Phe Leu Gly Gly
        195                 200                 205

Ser Pro Val Cys Leu Gly Gln Asn Ser Gln Ser Pro Thr Ser Asn His
    210                 215                 220

Ser Pro Thr Ser Cys Pro Pro Ile Cys Pro Gly Tyr Arg Trp Met Cys
225                 230                 235                 240

Leu Arg Arg Phe Ile Ile Phe Leu Phe Ile Leu Leu Leu Cys Leu Ile
                245                 250                 255

Phe Leu Leu Val Leu Leu Asp Tyr Gln Gly Met Leu Pro Val Cys Pro
            260                 265                 270

Leu Ile Pro Gly Ser Thr Thr Thr Ser Thr Gly Pro Cys Lys Thr Cys
        275                 280                 285
```

Thr Thr Pro Ala Gln Gly Asn Ser Met Phe Pro Ser Cys Cys Cys Thr
            290                 295                 300

Lys Pro Thr Asp Gly Asn Cys Thr Cys Ile Pro Ile Pro Ser Ser Trp
305                 310                 315                 320

Ala Phe Ala Lys Tyr Leu Trp Glu Trp Ala Ser Val Arg Phe Ser Trp
                325                 330                 335

Leu Ser Leu Leu Val Pro Phe Val Gln Trp Phe Val Gly Leu Ser Pro
            340                 345                 350

Thr Val Trp Leu Ser Ala Ile Trp Met Met Trp Tyr Trp Gly Pro Ser
            355                 360                 365

Leu Tyr Ser Ile Val Ser Pro Phe Ile Pro Leu Leu Pro Ile Phe Phe
            370                 375                 380

Cys Leu Trp Val Tyr Ile
385                 390

<210> SEQ ID NO 6
<211> LENGTH: 5882
<212> TYPE: DNA
<213> ORGANISM: Artificial Sequence
<220> FEATURE:
<223> OTHER INFORMATION: Description of Artificial Sequence: plasmid
      pCMV-II-E2661-sAg
<220> FEATURE:
<221> NAME/KEY: CDS
<222> LOCATION: (1992)..(3584)

<400> SEQUENCE: 6

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgaa gcttttttgca aaagcctagg cctccaaaaa agcctcctca ctacttctgg    240
aatagctcag aggccgaggc ggcctcggcc tctgcataaa taaaaaaaat tagtcagcca    300
tggggcggag aatgggcgga actgggcggg agggaatta ttggctattg gccattgcat    360
acgttgtatc tatatcataa tatgtacatt tatattggct catgtccaat atgaccgcca   420
tgttgacatt gattattgac tagttattaa tagtaatcaa ttacggggtc attagttcat    480
agcccatata tggagttccg cgttacataa cttacggtaa atggcccgcc tggctgaccg   540
cccaacgacc cccgcccatt gacgtcaata atgacgtatg ttcccatagt aacgccaata    600
gggactttcc attgacgtca atgggtggag tatttacggt aaactgccca cttggcagta    660
catcaagtgt atcatatgcc aagtccgccc cctattgacg tcaatgacgg taaatggccc    720
gcctggcatt atgcccagta catgaccttac ggactttc ctacttggca gtacatctac    780
gtattagtca tcgctattac catggtgatg cggttttggc agtacaccaa tgggcgtgga    840
tagcggtttg actcacgggg atttccaagt ctccacccca ttgacgtcaa tgggagtttg    900
ttttggcacc aaaatcaacg ggactttcca aatgtcgta ataaccccgc ccgttgacg     960 caaatgggcg gtaggcgtgt acggtgggag gtctatataa gcagagctcg tttagtgaac   1020
cgtcagatcg cctggagacg ccatccacgc tgttttgacc tccatagaag acaccgggac   1080
cgatccagcc tccgcggccg ggaacggtgc attggaacgc ggattcccg tgccaagagt    1140 gacgtaagta ccgcctatag actctatagg cacacccctt tggctcttat gcatgctata   1200 ctgttttttgg cttggggcct atacaccccc gctccttatg ctataggtga tgtatagct    1260 tagcctatag gtgtgggtta ttgaccatta ttgaccactc ccctattggt gacgatactt    1320
```

-continued

```
tccattacta atccataaca tggctctttg ccacaactat ctctattggc tatatgccaa   1380
tactctgtcc ttcagagact gacacggact ctgtattttt acaggatggg gtccatttat   1440
tatttacaaa ttcacatata caacaacgcc gtcccccgtg cccgcagttt ttattaaaca   1500
tagcgtggga tctccgacat tcgggtacg tgttccggac atgggctctt ctccggtagc   1560
ggcggagctt ccacatccga gccctggtcc catccgtcca gcggctcatg gtcgctcggc   1620
agctccttgc tcctaacagt ggaggccaga cttaggcaca gcacaatgcc caccaccacc   1680
agtgtgccgc acaaggccgt ggcggtaggg tatgtgtctg aaaatgagct cggagattgg   1740
gctcgcacct ggacgcagat ggaagactta aggcagcggc agaagaagat gcaggcagct   1800
gagttgttgt attctgataa gagtcagagg taactcccgt tgcggtgctg ttaacggtgg   1860
agggcagtgt agtctgagca gtactcgttg ctgccgcgcg cgccaccaga cataatagct   1920
gacagactaa cagactgttc ctttccatgg gtcttttctg cagtcaccgt cgtcgacgaa   1980
ttcaagcaat c atg gat gca atg aag aga ggg ctc tgc tgt gtg ctg ctg    2030
            Met Asp Ala Met Lys Arg Gly Leu Cys Cys Val Leu Leu
             1               5                  10 ctg tgt gga gca gtc ttc gtt tcg ccc agc gct agc gaa acc cac gtc     2078
Leu Cys Gly Ala Val Phe Val Ser Pro Ser Ala Ser Glu Thr His Val
 15                  20                  25 acc ggg gga agt gcc ggc cac act gtg tct gga ttt gtt agc ctc ctc     2126
Thr Gly Gly Ser Ala Gly His Thr Val Ser Gly Phe Val Ser Leu Leu
 30                  35                  40                  45 gca cca ggc gcc aag cag aac gtc cag ctg atc aac acc aac ggc agt     2174
Ala Pro Gly Ala Lys Gln Asn Val Gln Leu Ile Asn Thr Asn Gly Ser
                 50                  55                  60 tgg cac ctc aat agc acg gcc ctg aac tgc aat gat agc ctc aac acc     2222
Trp His Leu Asn Ser Thr Ala Leu Asn Cys Asn Asp Ser Leu Asn Thr
                 65                  70                  75 ggc tgg ttg gca ggg ctt ttc tat cac cac aag ttc aac tct tca ggc     2270
Gly Trp Leu Ala Gly Leu Phe Tyr His His Lys Phe Asn Ser Ser Gly
             80                  85                  90 tgt cct gag agg cta gcc agc tgc cga ccc ctt acc gat ttt gac cag     2318
Cys Pro Glu Arg Leu Ala Ser Cys Arg Pro Leu Thr Asp Phe Asp Gln
         95                 100                 105 ggc tgg ggc cct atc agt tat gcc aac gga agc ggc ccc gac cag cgc     2366
Gly Trp Gly Pro Ile Ser Tyr Ala Asn Gly Ser Gly Pro Asp Gln Arg
110                 115                 120                 125 ccc tac tgc tgg cac tac ccc cca aaa cct tgc ggt att gtg ccc gcg     2414
Pro Tyr Cys Trp His Tyr Pro Pro Lys Pro Cys Gly Ile Val Pro Ala
                130                 135                 140 aag agt gtg tgt ggt ccg gta tat tgc ttc act ccc agc ccc gtg gtg     2462
Lys Ser Val Cys Gly Pro Val Tyr Cys Phe Thr Pro Ser Pro Val Val
            145                 150                 155 gtg gga acg acc gac agg tcg ggc gcg ccc acc tac agc tgg ggt gaa     2510
Val Gly Thr Thr Asp Arg Ser Gly Ala Pro Thr Tyr Ser Trp Gly Glu
        160                 165                 170 aat gat acg gac gtc ttc gtc ctt aac aat acc agg cca ccg ctg ggc     2558
Asn Asp Thr Asp Val Phe Val Leu Asn Asn Thr Arg Pro Pro Leu Gly
175                 180                 185 aat tgg ttc ggt tgt acc tgg atg aac tca act gga ttc acc aaa gtg     2606
Asn Trp Phe Gly Cys Thr Trp Met Asn Ser Thr Gly Phe Thr Lys Val
190                 195                 200                 205 tgc gga gcg cct cct tgt gtc atc gga ggg gcg ggc aac aac acc ctg     2654
Cys Gly Ala Pro Pro Cys Val Ile Gly Gly Ala Gly Asn Asn Thr Leu
                210                 215                 220
```

```
cac tgc ccc act gat tgc ttc cgc aag cat ccg gac gcc aca tac tct    2702
His Cys Pro Thr Asp Cys Phe Arg Lys His Pro Asp Ala Thr Tyr Ser
            225                 230                 235 cgg tgc ggc tcc ggt ccc tgg atc aca ccc agg tgc ctg gtc gac tac    2750
Arg Cys Gly Ser Gly Pro Trp Ile Thr Pro Arg Cys Leu Val Asp Tyr
        240                 245                 250 ccg tat agg ctt tgg cat tat cct tgt acc atc aac tac acc ata ttt    2798
Pro Tyr Arg Leu Trp His Tyr Pro Cys Thr Ile Asn Tyr Thr Ile Phe
    255                 260                 265 aaa atc agg atg tac gtg gga ggg gtc gaa cac agg ctg gaa gct gcc    2846
Lys Ile Arg Met Tyr Val Gly Gly Val Glu His Arg Leu Glu Ala Ala
270                 275                 280                 285 tgc aac tgg acg cgg ggc gaa cgt tgc gat ctg gaa gat agg gac agg    2894
Cys Asn Trp Thr Arg Gly Glu Arg Cys Asp Leu Glu Asp Arg Asp Arg
                290                 295                 300 tcc gag atc gat atg gag aac atc aca tca gga ttc cta gga ccc ctg    2942
Ser Glu Ile Asp Met Glu Asn Ile Thr Ser Gly Phe Leu Gly Pro Leu
            305                 310                 315 ctc gtg tta cag gcg ggg ttt ttc ttg ttg aca aga atc ctc aca ata    2990
Leu Val Leu Gln Ala Gly Phe Phe Leu Leu Thr Arg Ile Leu Thr Ile
        320                 325                 330 ccg cag agt cta gac tcg tgg tgg act tct ctc aat ttt cta ggg gga    3038
Pro Gln Ser Leu Asp Ser Trp Trp Thr Ser Leu Asn Phe Leu Gly Gly
    335                 340                 345 tct ccc gtg tgt ctt ggc caa aat tcg cag tcc cca acc tcc aat cac    3086
Ser Pro Val Cys Leu Gly Gln Asn Ser Gln Ser Pro Thr Ser Asn His
350                 355                 360                 365 tca cca acc tcc tgt cct cca att tgt cct ggt tat cgc tgg atg tgt    3134
Ser Pro Thr Ser Cys Pro Pro Ile Cys Pro Gly Tyr Arg Trp Met Cys
                370                 375                 380 ctg cgg cgt ttt atc ata ttc ctc ttc atc ctg cta tgc ctc atc        3182
Leu Arg Arg Phe Ile Ile Phe Leu Phe Ile Leu Leu Leu Cys Leu Ile
            385                 390                 395 ttc tta ttg gtt ctt ctg gat tat caa ggt atg ttg ccc gtt tgt cct    3230
Phe Leu Leu Val Leu Leu Asp Tyr Gln Gly Met Leu Pro Val Cys Pro
        400                 405                 410 cta att cca gga tca aca aca acc agt acg gga cca tgc aaa acc tgc    3278
Leu Ile Pro Gly Ser Thr Thr Thr Ser Thr Gly Pro Cys Lys Thr Cys
    415                 420                 425 acg act cct gct caa ggc aac tct atg ttt ccc tca tgt tgc tgt aca    3326
Thr Thr Pro Ala Gln Gly Asn Ser Met Phe Pro Ser Cys Cys Cys Thr
430                 435                 440                 445 aaa cct acg gat gga aat tgc acc tgt att ccc atc cca tcg tcc tgg    3374
Lys Pro Thr Asp Gly Asn Cys Thr Cys Ile Pro Ile Pro Ser Ser Trp
                450                 455                 460 gct ttc gca aaa tac cta tgg gag tgg gcc tca gtc cgt ttc tct tgg    3422
Ala Phe Ala Lys Tyr Leu Trp Glu Trp Ala Ser Val Arg Phe Ser Trp
            465                 470                 475 ctc agt tta cta gtg cca ttt gtt cag tgg ttc gta ggg ctt tcc ccc    3470
Leu Ser Leu Leu Val Pro Phe Val Gln Trp Phe Val Gly Leu Ser Pro
        480                 485                 490 act gtt tgg ctt tca gct ata tgg atg atg tgg tat tgg ggg cca agt    3518
Thr Val Trp Leu Ser Ala Ile Trp Met Met Trp Tyr Trp Gly Pro Ser
    495                 500                 505 ctg tac agc atc gtg agt ccc ttt ata ccg ctg tta cca att ttc ttt    3566
Leu Tyr Ser Ile Val Ser Pro Phe Ile Pro Leu Leu Pro Ile Phe Phe
510                 515                 520                 525 tgt ctc tgg gta tac att taagaattca gactcgagca agtctagaaa           3614
Cys Leu Trp Val Tyr Ile
                530
```

-continued

```
ggcgcgccaa gatatcaagg atccactacg cgttagagct cgctgatcag cctcgactgt    3674
gccttctagt tgccagccat ctgttgtttg cccctccccc gtgccttcct tgaccctgga    3734
aggtgccact cccactgtcc tttcctaata aaatgaggaa attgcatcgc attgtctgag    3794
taggtgtcat tctattctgg ggggtggggt ggggcaggac agcaaggggg aggattggga    3854
agacaatagc aggcatgctg gggagctctt ccgcttcctc gctcactgac tcgctgcgct    3914
cggtcgttcg gctgcggcga gcggtatcag ctcactcaaa ggcggtaata cggttatcca    3974
cagaatcagg ggataacgca ggaaagaaca tgtgagcaaa aggccagcaa aaggccagga    4034
accgtaaaaa ggccgcgttg ctggcgtttt tccataggct ccgcccccct gacgagcatc    4094
acaaaaatcg acgctcaagt cagaggtggc gaaacccgac aggactataa agataccagg    4154
cgtttccccc tggaagctcc ctcgtgcgct ctcctgttcc gaccctgccg cttaccggat    4214
acctgtccgc ctttctccct tcgggaagcg tggcgctttc tcaatgctca cgctgtaggt    4274
atctcagttc ggtgtaggtc gttcgctcca agctgggctg tgtgcacgaa ccccccgttc    4334
agcccgaccg ctgcgcctta tccggtaact atcgtcttga gtccaacccg gtaagacacg    4394
acttatcgcc actggcagca gccactggta acaggattag cagagcgagg tatgtaggcg    4454
gtgctacaga gttcttgaag tggtggccta actacggcta cactagaagg acagtatttg    4514
gtatctgcgc tctgctgaag ccagttacct tcggaaaaag agttggtagc tcttgatccg    4574
gcaaacaaac caccgctggt agcggtggtt ttttttgtttg caagcagcag attacgcgca    4634
gaaaaaaagg atctcaagaa gatcctttga tcttttctac ggggtctgac gctcagtgga    4694
acgaaaactc acgttaaggg attttggtca tgagattatc aaaaaggatc ttcacctaga    4754
tccttttaaa ttaaaaatga agttttaaat caatctaaag tatatatgag taaacttggt    4814
ctgacagtta ccaatgctta atcagtgagg cacctatctc agcgatctgt ctatttcgtt    4874
catccatagt tgcctgactc cccgtcgtgt agataaactac gatacgggag gcttaccat    4934 ctggccccag tgctgcaatg ataccgcgag acccacgctc accggctcca gatttatcag    4994
caataaacca gccagccgga agggccgagc gcagaagtgg tcctgcaact ttatccgcct    5054
ccatccagtc tattaattgt tgccgggaag ctagagtaag tagttcgcca gttaatagtt    5114
tgcgcaacgt tgttgccatt gctacaggca tcgtggtgtc acgctcgtcg tttggtatgg    5174
cttcattcag ctccggttcc caacgatcaa ggcgagttac atgatccccc atgttgtgca    5234
aaaaagcggt tagctccttc ggtcctccga tcgttgtcag aagtaagttg gccgcagtgt    5294
tatcactcat ggttatggca gcactgcata attctcttac tgtcatgcca tccgtaagat    5354
gcttttctgt gactggtgag tactcaacca agtcattctg agaatagtgt atgcggcgac    5414
cgagttgctc ttgcccggcg tcaatacggg ataataccgc gccacatagc agaactttaa    5474
aagtgctcat cattggaaaa cgttcttcgg ggcgaaaact ctcaaggatc ttaccgctgt    5534
tgagatccag ttcgatgtaa cccactcgtg cacccaactg atcttcagca tcttttactt    5594
tcaccagcgt ttctgggtga gcaaaaacag gaaggcaaaa tgccgcaaaa aagggaataa    5654
gggcgacacg gaaatgttga atactcatac tcttcctttt tcaatattat tgaagcattt    5714
atcagggtta ttgtctcatg agcggataca tatttgaatg tatttagaaa aataaacaaa    5774
taggggttcc gcgcacattt ccccgaaaag tgccacctga cgtctaagaa accattatta    5834
tcatgacatt aacctataaa aataggcgta tcacgaggcc ctttcgtc                 5882
```

<210> SEQ ID NO 7

<211> LENGTH: 531
<212> TYPE: PRT
<213> ORGANISM: Artificial Sequence
<220> FEATURE:
<223> OTHER INFORMATION: Description of Artificial Sequence: plasmid pCMV-II-E2661-sAg

<400> SEQUENCE: 7

```
Met Asp Ala Met Lys Arg Gly Leu Cys Cys Val Leu Leu Leu Cys Gly
  1               5                  10                  15

Ala Val Phe Val Ser Pro Ser Ala Ser Glu Thr His Val Thr Gly Gly
             20                  25                  30

Ser Ala Gly His Thr Val Ser Gly Phe Val Ser Leu Leu Ala Pro Gly
         35                  40                  45

Ala Lys Gln Asn Val Gln Leu Ile Asn Thr Asn Gly Ser Trp His Leu
     50                  55                  60

Asn Ser Thr Ala Leu Asn Cys Asn Asp Ser Leu Asn Thr Gly Trp Leu
 65                  70                  75                  80

Ala Gly Leu Phe Tyr His His Lys Phe Asn Ser Ser Gly Cys Pro Glu
                 85                  90                  95

Arg Leu Ala Ser Cys Arg Pro Leu Thr Asp Phe Asp Gln Gly Trp Gly
            100                 105                 110

Pro Ile Ser Tyr Ala Asn Gly Ser Gly Pro Asp Gln Arg Pro Tyr Cys
        115                 120                 125

Trp His Tyr Pro Pro Lys Pro Cys Gly Ile Val Pro Ala Lys Ser Val
    130                 135                 140

Cys Gly Pro Val Tyr Cys Phe Thr Pro Ser Pro Val Val Val Gly Thr
145                 150                 155                 160

Thr Asp Arg Ser Gly Ala Pro Thr Tyr Ser Trp Gly Glu Asn Asp Thr
                165                 170                 175

Asp Val Phe Val Leu Asn Asn Thr Arg Pro Pro Leu Gly Asn Trp Phe
            180                 185                 190

Gly Cys Thr Trp Met Asn Ser Thr Gly Phe Thr Lys Val Cys Gly Ala
        195                 200                 205

Pro Pro Cys Val Ile Gly Gly Ala Gly Asn Asn Thr Leu His Cys Pro
    210                 215                 220

Thr Asp Cys Phe Arg Lys His Pro Asp Ala Thr Tyr Ser Arg Cys Gly
225                 230                 235                 240

Ser Gly Pro Trp Ile Thr Pro Arg Cys Leu Val Asp Tyr Pro Tyr Arg
                245                 250                 255

Leu Trp His Tyr Pro Cys Thr Ile Asn Tyr Thr Ile Phe Lys Ile Arg
            260                 265                 270

Met Tyr Val Gly Gly Val Glu His Arg Leu Glu Ala Ala Cys Asn Trp
        275                 280                 285

Thr Arg Gly Glu Arg Cys Asp Leu Glu Asp Arg Asp Arg Ser Glu Ile
    290                 295                 300

Asp Met Glu Asn Ile Thr Ser Gly Phe Leu Gly Pro Leu Leu Val Leu
305                 310                 315                 320

Gln Ala Gly Phe Phe Leu Leu Thr Arg Ile Leu Thr Ile Pro Gln Ser
                325                 330                 335

Leu Asp Ser Trp Trp Thr Ser Leu Asn Phe Leu Gly Gly Ser Pro Val
            340                 345                 350

Cys Leu Gly Gln Asn Ser Gln Ser Pro Thr Ser Asn His Ser Pro Thr
        355                 360                 365

Ser Cys Pro Pro Ile Cys Pro Gly Tyr Arg Trp Met Cys Leu Arg Arg
```

-continued

```
              370                 375                 380
Phe Ile Ile Phe Leu Phe Ile Leu Leu Leu Cys Leu Ile Phe Leu Leu
385                 390                 395                 400

Val Leu Leu Asp Tyr Gln Gly Met Leu Pro Val Cys Pro Leu Ile Pro
                405                 410                 415

Gly Ser Thr Thr Thr Ser Thr Gly Pro Cys Lys Thr Cys Thr Thr Pro
                420                 425                 430

Ala Gln Gly Asn Ser Met Phe Pro Ser Cys Cys Cys Thr Lys Pro Thr
            435                 440                 445

Asp Gly Asn Cys Thr Cys Ile Pro Ile Pro Ser Ser Trp Ala Phe Ala
        450                 455                 460

Lys Tyr Leu Trp Glu Trp Ala Ser Val Arg Phe Ser Trp Leu Ser Leu
465                 470                 475                 480

Leu Val Pro Phe Val Gln Trp Phe Val Gly Leu Ser Pro Thr Val Trp
                485                 490                 495

Leu Ser Ala Ile Trp Met Met Trp Tyr Trp Gly Pro Ser Leu Tyr Ser
                500                 505                 510

Ile Val Ser Pro Phe Ile Pro Leu Leu Pro Ile Phe Phe Cys Leu Trp
            515                 520                 525

Val Tyr Ile
        530
```